US010006063B2

(12) United States Patent
Zhang et al.

(10) Patent No.: US 10,006,063 B2
(45) Date of Patent: *Jun. 26, 2018

(54) RECOMBINANT *ESCHERICHIA COLI* FOR PRODUCING SUCCINATE ACID AND APPLICATION THEREOF

(71) Applicant: Tianjin Institute of Industrial Biotechnology, Chinese Academy of Sciences, Tianjin (CN)

(72) Inventors: Xueli Zhang, Tianjin (CN); Xinna Zhu, Tianjin (CN); Hongtao Xu, Tianjin (CN); Zaigao Tan, Tianjin (CN)

(73) Assignee: TIANJIN INSTITUTE OF INDUSTRIAL BIOTECHNOLOGY, CHINESE ACADEMY OF SCIENCES, Tianjin (CN)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/891,776

(22) PCT Filed: May 23, 2014

(86) PCT No.: PCT/CN2014/078284
§ 371 (c)(1),
(2) Date: Nov. 17, 2015

(87) PCT Pub. No.: WO2014/187357
PCT Pub. Date: Nov. 27, 2014

(65) Prior Publication Data
US 2016/0097064 A1 Apr. 7, 2016

(30) Foreign Application Priority Data
May 24, 2013 (CN) .......................... 2013 1 0198953

(51) Int. Cl.
*C12N 1/20* (2006.01)
*C12P 7/46* (2006.01)
(Continued)

(52) U.S. Cl.
CPC .................. *C12P 7/46* (2013.01); *C12N 1/20* (2013.01); *C12N 9/0051* (2013.01); *C12N 15/52* (2013.01);
(Continued)

(58) Field of Classification Search
None
See application file for complete search history.

(56) References Cited

U.S. PATENT DOCUMENTS 9,605,280 B2 * 3/2017 Zhang ..................... C12P 7/065
2006/0073577 A1 * 4/2006 Ka-Yiu ..................... C12P 7/40
435/106
(Continued)

FOREIGN PATENT DOCUMENTS

CN 101023178 A 8/2007
CN 101128577 A 2/2008
(Continued)

OTHER PUBLICATIONS

English Translation of the Written Opinion of the ISA in PCT/CN2014/078284, dated Sep. 3, 2014.*
(Continued)

*Primary Examiner* — Richard C Ekstrom
(74) *Attorney, Agent, or Firm* — Swanson & Bratschun, L.L.C.

(57) ABSTRACT

The invention relates to the field of producing succinate by *E. coli* fermentation. Specifically, the invention provides an engineered recombinant *E. coli* for producing succinate, wherein said *E. coli* contains one or more of the following modifications: a) enhanced activity of the protein(s) encoded
(Continued)

by the gene(s) involved in pentose phosphate pathway (PPP), b) enhanced activity of the protein encoded by sthA gene, and optionally c) mutant lpdA gene. The invention also relates to use of the engineered recombinant *E. coli* for producing succinate, and a method of using the engineered recombinant *E. coli* for producing succinate.

13 Claims, 11 Drawing Sheets

(51) Int. Cl.
  C12R 1/19 (2006.01)
  C12N 15/52 (2006.01)
  C12N 9/02 (2006.01)
(52) U.S. Cl.
  CPC ........ *C12R 1/19* (2013.01); *C12Y 108/01004* (2013.01)

(56) References Cited

U.S. PATENT DOCUMENTS

| | | | | |
|---|---|---|---|---|
| 2008/0305533 | A1* | 12/2008 | Yi | C12P 7/46 435/145 |
| 2012/0058530 | A1* | 3/2012 | Zhang | C12P 7/46 435/145 |
| 2012/0276603 | A1* | 11/2012 | Beck | C12N 9/0006 435/146 |
| 2013/0040297 | A1* | 2/2013 | Klaassen | C07K 14/395 435/6.11 |
| 2013/0267012 | A1* | 10/2013 | Steen | C12P 7/40 435/254.21 |
| 2014/0235815 | A1 | 8/2014 | Burgard et al. | |
| 2015/0203877 | A1* | 7/2015 | Rush | C12P 5/026 435/141 |
| 2016/0145648 | A1 | 5/2016 | Zhang et al. | |

FOREIGN PATENT DOCUMENTS

| | | |
|---|---|---|
| CN | 102174455 A | 9/2011 |
| CN | 102803470 A | 11/2012 |
| RU | 2466186 C2 | 11/2012 |
| WO | WO 2009/062190 A2 | 5/2009 |
| WO | WO 2014/187355 A1 | 11/2014 |

OTHER PUBLICATIONS

U.S. Appl. No. 61/675,788, Specification, Claims and Abstract, filed Jul. 25, 2012.*
Datsenko et al., "One-step inactivation of chromosomal genes in *Escherichia coli* K-12 using PCR products" PNAS vol. 97, No. 12, pp. 6640-6645, Jun. 6, 2000.
Hong et al., "Research Progress on Metabolic Engineering of *Escherichia coli* 1-13 Strains for Ethanol Production", Journal of Agricultural Science and Technology, No. 4, vol. 11, Aug. 15, 2009, pp. 29-33 (with Eng. Abstract).
International Search Report dated Sep. 3, 2014 in PCT/CN2014/078284.
International Search Report dated Aug. 13, 2014 in PCT/CN2014/078265.
Jantama et al., "Combining Metabolic Engineering and Metabolic Evolution to Develop Nonrecombinant Strains of *Escherichia coli* C That Produce Succinate and Malate", Biotechnology and Bioengineering vol. 99, No. 5, Apr. 1, 2008, 1140-1153.
Jantama et al., "Eliminating Side Products and Increasing Succinate Yield in in Engineered Strains of *E. coli* C", Biotechnology and Bioengineering vol. 101, No. 5, Dec. 1, 2008, 881-893.
Kim et al., "Construction of an *Escherichia coli* K-12 Mutant for Homoethanologenic Fermentation of Glucose or Xylose without Foreign Genes" Applied and Environmental Microbiology, vol. 73, No. 6, Mar. 2007, pp. 1766-1771.
Kim et al., "Dihydrolipoamide Dehydrogenase Mutation Alters the NADH Sensitivity of 1-13 Pyruvate Dehydrogenase Complex of *Escherichia coli* K-12", Journal of Bacteriology, No. 11, vol. 190, Jun. 2008, pp. 3851-3858.
Lee et al., "Metabolic Engineering of *Escherichia coli* for Enhanced Production of Succinic Acid, Based on Genome Comparison and In Silico Gene Knockout Simulation" Appl. Environ. Microbiol. 2005, 71(12):7880-7887.
Lu et al. "Combinatorial modulation of galP and glk gene expression for improved alternative glucose utilization", Appl Microbiol Biotechnol. DOI 10.1007/s00253-011-3752-y, Publication online Dec. 13, 2011.
Sanchez et al., "Novel pathway engineering design of the anaerobic central metabolic pathway in *Escherichia coli* to increase succinate yield and productivity", Metabolic Engineering (2005) 7:229-239.
Scholten et al. "Continuous cultivation approach for fermentative succinic acid production from crude glycerol by Basfia succiniciproducens DD1", Biotechnol Lett (2009) 31:1947-1951.
Tan et al., "Activating Phosphoenolpyruvate Carboxylase and Phosphoenolpyruvate Carboxykinase in Combination for Improvement of Succinate Production", Applied and Environmental Microbiology Aug. 2013 vol. 79, No. 16, p. 4838-4844.
Vemuri et al., "Effects of Growth Mode and Pyruvate Carboxylase on Succinic Acid Production by Metabolically Engineered Strains of *Escherichia coli*", Appl. Environ. Microbiol. 2002, 68(4):1715-1727.
Wilkinson et al., "NADH Inhibition and NAD Activation of *Escherichia coli* Lipoamide Dehydrogenase Catalyzing the NADH-Lipoamide Reaction*", The Journal of Biological Chemistry, No. 256, vol. 5, Mar. 10, 1981, pp. 2307-2314.
Wu et al., "Research Progress on Fiber Hydrolyzate Fermentation Production of Succinate", Food and Fermentation Industries, vol. 38, No. 9, Sep. 30, 2012 (with Eng Abstract).
Zhang et al., "Metabolic evolution of energy-conserving pathways for succinate production in *Escherichia coli*" PNAS Dec. 1, 2009. vol. 106. No. 48, p. 20180-20185.
Zhang et al., "Reengineering *Escherichia coli* for Succinate Production in Mineral Salts Medium", Applied and Environmental Microbiology, Dec. 2009, vol. 75, No. 24, p. 7807-7813.
Zhao et al., "Engineering central metabolic modules of *Escherichia coli* for improving b-carotene production" Metabolic Engineering, http://dx.doi.org/10.1016/j.ymben.2013.02.002 Feb. 2, 2013.
Zhou et al., "Engineering a native homoethanol pathway in *Escherichia coli* B for ethanol production", Biotechnol Lett (2008) 30:335-342.
Zhu et al. "Metabolic evolution of two reducing equivalent-conserving pathways for high-yield succinate production in *Escherichia coli*", Metabolic Engineering (2014) 24:87-96.
Balzer et al., "Metabolic engineering of *Escherichia coli* to minimize byproduct formate and improving succinate productivity through increasing NADH availability by heterologous expression of NAD+-dependent formate dehydrogenase", Metab. Eng. 2013, 20, 1-8.
Broun et al., "Catalytic plasticity of fatty acid modification enzymes underlying chemical diversity of plant lipids" Science, 1998, vol. 282: 1315-1317.
Chatterjee et al. "Mutation of the ptsG gene results in increased production of succinate in fermentation of glucose by *Escherichia coli*", Appl. Environ. Microbiol. Jan. 2001, 67(1), 148-154.
Chen et al., "Activating $C_4$-dicarboxylate transporters DcuB and DcuC for improving succinate production", Appl. Microbiol. Biotechnol. 2014, 98, 2197-2205.
Devos et al., "Practical limits of function prediction" Proteins: Structure, Function, and Genetics. 2000, vol. 41: 98-107.
Uniprot Acc# H64111; Fleischmann et al., "Whole-Genome Random Sequencing and Assembly of *Haemophilus influenzae* Rd", Science Jul. 1995, 269:496-512.
Lee et al., "Genome-based metabolic engineering of *Mannheimia succiniciproducens* for succinic acid production", Appl. Environ. Microbiol. Mar. 2006, 72(3), 1939-1948.

(56) References Cited

OTHER PUBLICATIONS

Samuelov et al., "Influence of $CO_2$—$HCO_3$-levels and pH on growth, succinate production, and enzyme activities of *Anaerobiospirillum succiniciproducens*" Appl. Environ. Microbiol. Oct. 1991, 57(10), 3013-3019.
Seffernick et al., "Melamine deaminase and Atrazine chlorohydrolase: 98 percent identical but functionally different" J. Bacteriol., Apr. 2001, vol. 183 (8): 2405-2410.
Singh et al., "Manipulating redox and ATP balancing for improved production of succinate in *E. coli*." Metab. Eng. 2011, 13, 76-81.
Stols et al., "Production of succinic acid through overexpression of $NAD^+$-dependent malic enzyme in an *Escherichia coli* mutant", Appl. Environ. Microbiol. Jul. 1997, 63(7), 2695-2701.
Van der Werf et al., "Environmental and physiological factors affecting the succinate product ratio during carbohydrate fermentation by *Actinobacillus* sp. 130Z", Arch. Microbiol. 1997, 167, 332-342.
Wang et al., "Succinate production from different carbon sources under anaerobic conditions by metabolic engineered *Escherichia coli* strains", Metab. Eng. 2011, 13, 328-335.
Whisstock et al., "Prediction of protein function from protein sequence and structure" Q. Rev. Biophysics., 2003, vol. 36 (3): 307-340.
Witkowski et al., "Conversion of a β-Ketoacyl Synthase to a Malonyl Decarboxylase by Replacement of the Active-Site Cysteine with Glutamine" Biochemistry 1999, 38:11643-11650.
Zhu et al., "Activation of glyoxylate pathway without the activation of its related gene in succinate-producing engineered *Escherichia coli*", Metab. Eng. 2013, 20, 9-19.

\* cited by examiner

Figure 8B

RECOMBINANT ESCHERICHIA COLI FOR PRODUCING SUCCINATE ACID AND APPLICATION THEREOF

RELATED APPLICATIONS

This application is a 35 U.S.C. § 371 national phase application of PCT/CN2014/078284 (WO 2014/187357) filed on May 23, 2014, entitled "RECOMBINANT ESCHERICHIA COLI FOR PRODUCING SUCCINIC ACID AND APPLICATION THEREOF", which application claims the benefit of Chinese Application No 201310198953.9, filed May 24, 2013, which is incorporated herein by reference in its entirety.

FIELD OF THE INVENTION

The invention relates to the field of producing succinate by fermentation of *Escherichia coli*. Specifically, the invention provides an engineered recombinant *E. coli* strain for producing succinate. The invention also relates to use of the engineered recombinant *E. coli* strain for producing succinate, and a method of using the engineered recombinant *E. coli* strain for producing succinate.

Incorporated by reference herein in its entirety is the Sequence Listing entitled "Sequence listing.txt", created Nov. 11, 2015, size of 61 kilobytes.

BACKGROUND OF THE INVENTION

Succinate, also called butanedioic acid, is an excellent platform chemical, which is extensively used in the fields of chemical industry, material, medicines, and food industry, and is considered as one of the 12 most valuable platform chemicals by U. S. Department of Energy (McKinlay et al. 2007, Appl Microbiol Biotechnol 76:727-740). Currently, succinate is mainly used in esterification solvent, deicer, engine coolant, food flavour, water treatment chemicals etc. Succinate can also be used for producing many downstream products, such as 1,4-butanediol, tetrahydrofuran, γ-butyrolactone, N-methylpyrrolidone and 2-pyrrolidone. Besides, succinate and 1,4-butanediol can be polymerized to produce PBS (poly-butylene succinate) plastics, which is a biodegradable plastics with excellent properties. It is estimated that the future market potential of succinate would exceed 2,700,000 tons per year. About 250 chemical products (produced on the basis of benzene material) can all be produced by using succinate as a raw material (McKinlay et al. 2007, Appl Microbiol Biotechnol 76:727-740).

Currently, the production of succinate is mainly based on petrochemical routes using maleic anhydride as raw material. The prices of petroleum greatly fluctuate in recent years, which seriously limit the sustainability and price stability of succinate production. On the other hand, chemical synthesis has complicated processes and usually requires high pressure and high temperature, which greatly increase the energy and material costs during the production; and additionally chemical synthesis also results in serious environmental pollution. The development of high performance bio-manufacturing technology of succinate can fundamentally solve the disadvantages of petrochemical routes, such as ensuring the stable price of succinate without being influenced by the fluctuation of petroleum prices, decreasing the manufacture cost for PBS plastics to facilitate its further applications; realizing green sustainable production, simplifying production process, saving energy and reducing emission, and decreasing environmental pollution. Further, the bio-manufacturing process of succinate can also absorb carbon dioxide, which is a good promotion for low-carbon economics. The core of succinate bio-manufacturing technology is a microbial strain that can effectively convert biomass materials into succinate.

Currently, there are mainly two categories of succinate fermentation bacteria. The first are bacteria that naturally produce succinate, including *Actinobacillus succinogens* (Guettler et al. 1996, U.S. Pat. No. 5,504,004), *Anaerobiospirillum succiniciproducens* (Glassner and Datta 1992, U.S. Pat. No. 5,143,834), *Mannheimia succiniciproducens* (Lee et al. 2002, Appl Microbiol Biotechnol 58:663-668) and *Basfia succiniciproducens* (Scholten et al. 2009, Biotechnol Lett 31:1947-1951). The other are engineered bacteria that are modified through metabolic engineering, which are mainly *E. coli*.

Although natural succinate-producing bacteria can produce succinate in high titers, they have disadvantages. During fermentation, the conversion rate of sugar to succinate is low, and a considerable portion of carbon flux flows into the synthesis of other organic acids. Further, the fermentation of natural succinate-producing bacteria requires rich medium, which increases the production cost as well as the downstream isolation-purification cost, limiting their large-scale industrial production. *E. coli* only accumulates small amount of succinate during sugar fermentation, but it has a clear physiological and genetic background and is easy to be modified. Many research institutes choose *E. coli* as starting bacteria, and modify it as engineered bacteria that can produce succinate with high yield.

Phosphoenolpyruvate (PEP) is a key precursor in succinate synthesis pathways. The carboxylation of PEP into oxaloacetic acid (OAA) is a key step in succinate synthesis pathways. Millard et al. increased the yield of succinate by 3.5 times through over-expressing *E. coli* PEP carboxylase gene ppc (Millard et al., 1996, Appl Environ Microbiol 62:1808-1810). Kim et al. discovered that overexpression of PEP carboxykinase gene pck in wild-type *E. coli* showed no influence on succinate production, but overexpression of pck gene in *E. coli* with ppc gene deletion could increase the yield of succinate by 6.5 times (Kim et al., 2004, Appl Environ Microbiol 70:1238-1241). Kwon et al. of South Korea further discovered that, when the fermentation broth contains bicarbonate ions at high concentration, overexpression of pck gene in wild-type *E. coli* could increase the yield of succinate by 2.2 times (Kwon et al., 2006, J Microbiol Biotechnol 16:1448-1452).

Chatterjee et al. constructed an engineered strain NZN111 by inactivating pyruvate formate lyase gene pflB and lactate dehydrogenase gene ldhA in *E. coli*. This strain cannot grow with glucose as carbon source, but can produce succinate, acetate and ethanol by using lactose, fructose, mannose or fructose as carbon source. On this basis, the mutant strain AFP111, which can reuse glucose as carbon source to grow during fermentation, was screened out (Chatterjee et al., 2001, Appl Environ Microbiol 67:148-154; Donnelly et al., 1998, Appl Biochem Biotechnol 70-72:187-198). Vemuri et al. further increased the yield of succinate by over-expressing *Rhizobium etli* pyruvate carboxylase gene pyc in AFP111. During dual-phase fermentation (first aerobic cultivation, and then anaerobic fermentation to produce acids), the final concentration of succinate could reach 99.2 g/L (841 mM), with a sugar-acid conversion rate of 1.1 g/g (1.68 mol/mol) (Vemuri et al., 2002, J Ind Microbiol Biotechnol 28:325-332).

Sanchez et al. constructed an engineered strain SBS550MG by inactivating alcohol dehydrogenase genes adhE and ldhA, acetate kinase gene ackA, phosphate acetyltransferase gene pta, and isocitrate lyase regulatory protein gene iciR. During dual-phase fermentation (first aerobic culture, and then anaerobic fermentation to produce acids), it could produce 40 g/L (339 mM) of succinate, with a yield of 1.06 g/g (1.61 mol/mol) (Sanchez et al., 2005, Metab Eng 7:229-239).

The recombinant *E. coli* strains constructed by Vemuri et al. and Sanchez et al. can produce succinate in high titer, but still have disadvantages. The fermentation process employed therein is dual-phase fermentation, i.e. first using an aerobic process to grow the cell culture, and then an anaerobic process to perform fermentation. The operation of such processes is complicated, and the aerobic process greatly increases the cost for device construction and operation. Such recombinant *E. coli* strains require rich medium, which greatly increases the material cost for fermentation, and results in higher calculated succinate yield.

Jantama et al. constructed a recombinant *E. coli* strain KJ073 by inactivating ldhA, adhE, formate transporter gene focA, pflB, ackA, methylglyoxal synthetase gene mgsA and pyruvate oxidase gene poxB as well as by subjecting to metabolic evolution. Using mineral salt medium, it can produce 79 g/L (668 mM) of succinate under anaerobic conditions, with a yield of 0.79 g/g (1.2 mol/mol) (Jantama et al., PCT/US2008/057439; Jantama et al., 2008a, Biotechnol Bioeng 99:1140-1153). Recombinant *E. coli* strain KJ122 was constructed by further inactivating propionate kinase gene tdcD, 2-ketone methyl butyrate lyase/pyruvate formate lyase gene tdcE, aspartate aminotransferase gene aspC and malic enzyme gene sfcA as well as by subjecting to metabolic evolution. Using mineral salt medium, it can produce 80 g/L (680 mM) of succinate under anaerobic conditions, with a yield of 0.89 g/g (1.36 mol/mol) (Jantama et al., PCT/US2008/057439; Jantama et al., 2008b, Biotechnol Bioeng 101:881-893). By metabolic evolution, these two recombinant *E. coli* strains improved the ability of producing succinate. Zhang et al. constructed a recombinant *E. coli* strain XZ721 by deleting PEP-phosphosugar transferase I genes ptsI and pflB as well as by enhancing the activity of PEP carboxykinase (PCK). Using mineral salt medium, it can produce 39 g/L (327 mM) of succinate under anaerobic conditions, with a yield of 0.82 g/g (1.25 mol/mol) (Zhang et al., PCT/US2010/029728; Zhang et al., 2009b, Appl Environ Microbiol 75:7807-7813).

In order to increase the titer and/or yield of succinate produced by *E. coli*, it is desired to further modify metabolic pathways of *E. coli*.

SUMMARY OF THE INVENTION

In one aspect, the invention provides a recombinant *E. coli* for producing succinate.

In one embodiment, the invention relates to a recombinant *E. coli*, comprising the modifications of: (1) inhibited expression of gene(s) involved in phosphoenolpyruvate:sugar phosphotransferase system (PTS), and/or inhibited activity of protein(s) encoded by gene(s) involved in phosphoenolpyruvate:sugar phosphotransferase system (PTS), (2) inhibited expression of pflB and/or adhE genes, and/or inhibited activity of protein(s) encoded by pflB and/or adhE genes, (3) inhibited expression of ldhA gene, and/or inhibited activity of the protein encoded by ldhA gene, and (4) enhanced expression of galP gene and/or exogenous glf gene, and/or enhanced activity of the protein(s) encoded by galP gene and/or exogenous glf gene; wherein said *E. coli* further comprises one or more of the following modifications: (a) enhanced expression of gene(s) involved in pentose phosphate pathway (PPP), and/or enhanced activity of protein(s) encoded by gene(s) involved in pentose phosphate pathway (PPP); and (b) enhanced expression of sthA gene, and/or enhanced activity of the protein encoded by sthA gene.

In one embodiment, the *E. coli* of the invention has inhibited expression of gene(s) involved in phosphoenolpyruvate:sugar phosphotransferase system (PTS), and/or inhibited activity of protein(s) encoded by gene(s) involved in phosphoenolpyruvate:sugar phosphotransferase system (PTS), wherein said gene(s) are one or more genes selected from the group consisting of genes ptsI encoding PTS system enzyme I, ptsH encoding PTS system enzyme Hpr, crr encoding PTS system enzyme IIA$^{Glc}$, and ptsG encoding PTS system enzyme IICB$^{Glc}$.

In another embodiment, in the *E. coli* of the invention, the expression of gene(s) involved in pentose phosphate pathway (PPP) is enhanced, and/or the activity of protein(s) encoded by gene(s) involved in pentose phosphate pathway (PPP) is enhanced, wherein said gene(s) are one or more genes selected from the group consisting of genes: tktA encoding transketolase, zwf encoding 6-phosphoglucose dehydrogenase, pgl encoding 6-phosphogluconolactonase, gnd encoding 6-phosphogluconate dehydrogenase, rpi encoding ribose-5-phosphate isomerase, rpe encoding ribulose-5-phosphate epimerase, and talB encoding transaldolase.

In a further embodiment, said gene(s) of pentose phosphate pathway (PPP), which have enhanced expression or the activity of protein(s) encoded by which is enhanced, are one or more genes selected from the group consisting of genes: tktA encoding transketolase, zwf encoding 6-phosphoglucose dehydrogenase, pgl encoding 6-phosphogluconolactonase, gnd encoding 6-phosphogluconate dehydrogenase and talB encoding transaldolase.

In one embodiment, the invention relates to a recombinant *E. coli*, wherein said *E. coli* has enhanced expression of sthA and tktA genes, and/or enhanced activities of the proteins encoded by sthA and tktA genes.

In one embodiment, the *E. coli* of the invention comprises a mutant lpdA gene, the polypeptide encoded by which comprises modifications at positions corresponding to the positions T81, P275, and A358 of the amino acid sequence shown in SEQ ID No:1, wherein the corresponding positions are determined by aligning the sequence of the polypeptide with SEQ ID No:1, optionally wherein at the position corresponding to T81, T is replaced with I, at the position corresponding to P275, P is replaced with S, and at the position corresponding to A358, A is replaced with V. In a preferred embodiment, in the *E. coli* of the invention, the expression of the mutant lpdA gene is enhanced, and/or the activity of the protein encoded by said mutant lpdA gene is enhanced.

In one embodiment, the *E. coli* of the invention comprises a mutant lpdA gene, and said mutant lpdA gene is in a plasmid or in a chromosome.

In one embodiment, the invention relates to a recombinant *E. coli*, wherein the *E. coli* comprises the modifications of: (a) enhanced expression of gene(s) involved in pentose phosphate pathway (PPP), and/or enhanced activity of protein(s) encoded by gene(s) involved in pentose phosphate pathway (PPP); (b) enhanced expression of sthA gene, and/or enhanced activity of the protein encoded by sthA gene; and (c) a mutant lpdA gene, the polypeptide encoded by which comprises modifications at positions corresponding to the positions T81, P275, and A358 of the amino acid sequence shown in SEQ ID No:1, wherein the corresponding positions are determined by aligning the sequence of the polypeptide with SEQ ID No:1, optionally wherein at the position corresponding to T81, T is replaced with I, at the position corresponding to P275, P is replaced with S, and at the position corresponding to A358, A is replaced with V. In one preferred embodiment, in the *E. coli* of the invention, the expression of the mutant lpdA gene is enhanced, and/or the activity of the protein encoded by said mutant lpdA gene is enhanced.

In one embodiment, the *E. coli* of the invention also comprises the modifications of: (5) inhibited expressions of ackA and pta genes, and/or inhibited activities of the proteins encoded by ackA and pta genes; (6) enhanced expression of aceBA gene cluster, and/or enhanced activity of the protein(s) encoded by aceBA gene cluster; (7) enhanced expression of dcuC gene, and/or enhanced activity of the protein encoded by dcuC gene; and (8) inhibited expression of mgsA gene, and/or inhibited activity of the protein encoded by mgsA gene.

In one embodiment, the *E. coli* of the invention further comprises the modifications of: (9) enhanced expression of pck gene, and/or enhanced activity of the protein encoded by pck gene.

In one embodiment, the *E. coli* of the invention further comprises the modifications of: (10) inhibited expression of adhE gene, and/or inhibited activity of the protein encoded by adhE gene; and (11) inhibited expression of tdcDE gene cluster, and/or inhibited activity of the protein(s) encoded by tdcDE gene cluster.

In one embodiment, the *E. coli* of the invention further comprises the modifications of: (12) enhanced expression of aceEF gene cluster, and/or enhanced activity of the protein(s) encoded by aceEF gene cluster.

In second aspect, the invention provides a method for producing succinate, comprising the step of culturing the *E. coli* of the invention.

In third aspect, the invention relates to use of the *E. coli* of the invention in the production of succinate.

DETAILED DESCRIPTION OF THE INVENTION

Figure 1:
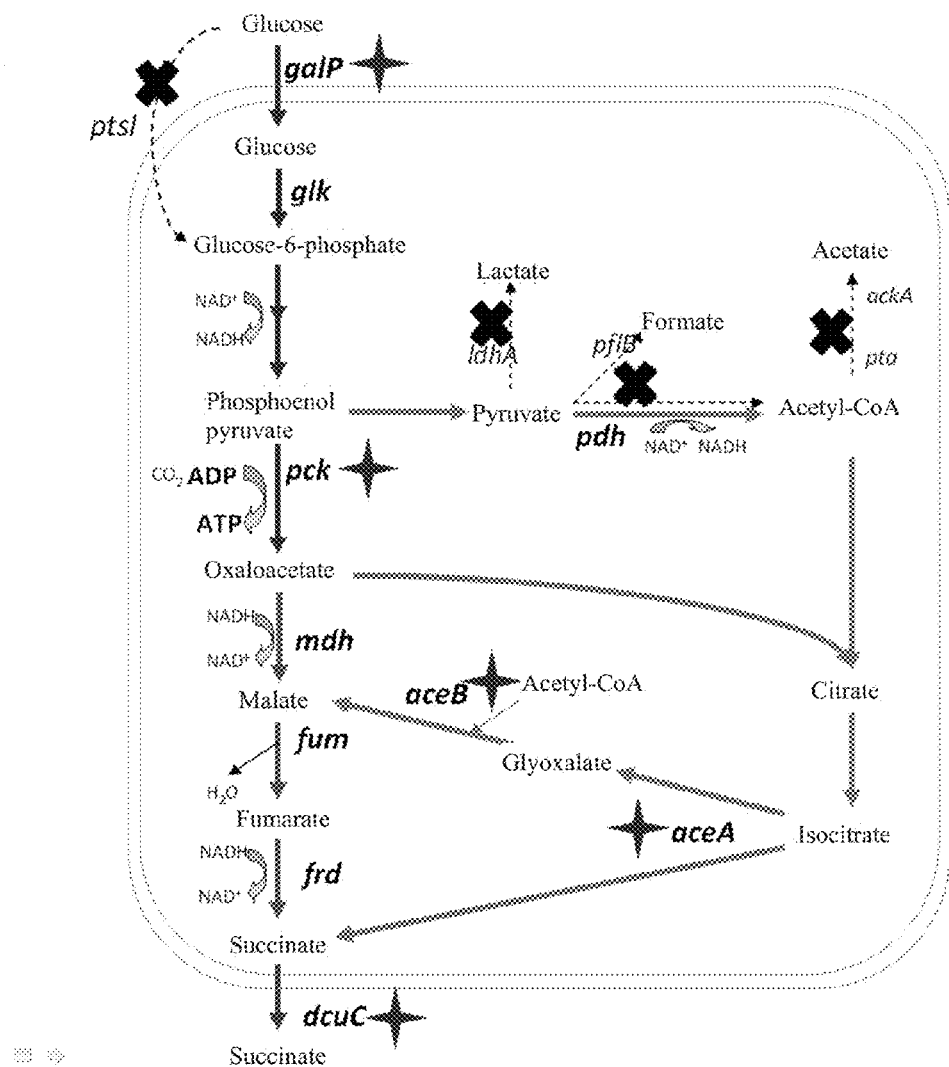
FIG. 1: schematic diagram for modifying *E. coli* to obtain the recombinant strain NZ-037. X represents deleting a gene, including ldhA, pflB, ptsI and ackA-pta genes. Four-angle star represents enhanced expression of a gene, including galP, pck, aceBA and dcuC genes.

Unless otherwise indicated, all technical and scientific terms have the common meanings known in the art. All the patents, patent applications, publications, sequences, and other published material are incorporated herein as references, unless otherwise indicated.

In one aspect, the invention provides an engineered recombinant *E. coli* for producing succinate. In the *E. coli* of the invention, the succinate yield and/or conversion rate of *E. coli* are improved by modulating the activities of some enzymes involved in metabolic pathways.

As used herein, the terms "Engineered recombinant *E. coli*", "Engineered *E. coli*" and "Recombinant *E. coli*" can be used interchangeably, and refer to a modified *E. coli*, wherein the modification can be selected from e.g., enhanced expression of a gene, inhibited expression of a gene, introduction of new gene(s), introduction of mutant gene(s), or mutation of gene(s), wherein the enhanced expression or inhibited expression of a gene can be achieved by using common techniques in the art, such as gene deletion, changed gene copy number, introduction of a plasmid, changed gene promoter (e.g. by using a strong or weak promoter) etc.

In one embodiment, the invention relates to a recombinant *E. coli*, wherein the *E. coli* comprises one or more of the following modifications: (a) enhanced expression of the gene(s) involved in pentose phosphate pathway (PPP), and/or enhanced activity of the protein(s) encoded by the gene(s) involved in pentose phosphate pathway (PPP); and (b) enhanced expression of sthA gene, and/or enhanced activity of the protein encoded by sthA gene.

As used herein, the term "pentose phosphate pathway" has the common meaning known in the art. Pentose phosphate pathway is one catabolic pathway of sugar that widely exists in animals, plants and microbes, and characterized in that glucose is directly oxidized to achieve dehydrogenation and decarboxylization, not undergoing glycolysis, and the coenzyme for dehydrogenase is NADP instead of $NAD^+$, and the generated NADPH is used as reducing equivalent for biosynthesis, rather than being delivered to $O_2$.

In some embodiments, in the *E. coli* of the invention, the expression of the gene(s) involved in pentose phosphate pathway (PPP) is enhanced, and/or the activity of the protein(s) encoded by the gene(s) involved in pentose phosphate pathway (PPP) is enhanced, wherein said gene(s) are one or more genes selected from the group consisting of genes tktA encoding transketolase, zwf encoding 6-phosphoglucose dehydrogenase, pgl encoding 6-Phosphogluconolactonase, gnd encoding 6-phosphogluconate dehydrogenase, rpi encoding ribose-5-phosphate isomerase, rpe encoding ribulose-5-phosphate-epimerase, and talB encoding transaldolase.

In the invention, the protein encoded by tktA gene (Genbank No: ACA76448.1) is transketolase (EC No: 2.2.1.1), the protein encoded by zwf gene (Genbank No: ACA77430.1) is 6-phosphoglucose dehydrogenase (EC No: 1.1.1.49), the protein encoded by pgl gene (Genbank No: ACA78522.1) is 6-Phosphogluconolactonase (EC No: 3.1.1.31), the protein encoded by gnd gene (Genbank No: ACA76645.1) is 6-phosphogluconate dehydrogenase (EC No: 1.1.1.44), the protein encoded by rpi gene (Genbank No: ACA76468.1) is ribose-5-phosphate isomerase (EC No: 5.3.1.6), the protein encoded by rpe gene (Genbank No: ACA76005.1) is ribulose-5-phosphate-epimerase (EC No: 5.1.3.1), and the protein encoded by talB gene (Genbank No: ACA79258.1) is transaldolase (EC No: 2.2.1.2).

SthA gene (Genbank No: ACA79653.1) encodes a soluble transhydrogenase (EC No: 1.6.1.1). In one embodiment, the sequence of sthA gene according to the invention is set forth in SEQ ID No:5. In one embodiment, the sequence of sthA gene according to the invention has a sequence identity of 90%, 91%, 92%, 93%, 94%, 95%, 96%, 97%, 98%, or 99% with the nucleotide sequence as set forth in SEQ ID No:5.

In one embodiment, the sequence of tktA gene according to the invention is set forth in SEQ ID No:6. In one embodiment, the sequence of tktA gene according to the invention has a sequence identity of 90%, 91%, 92%, 93%, 94%, 95%, 96%, 97%, 98%, or 99% with the nucleotide sequence as set forth in SEQ ID No:6.

As used herein, the term "enhanced expression of a gene" has the common meaning known in the art, and refers to enhanced intensity of gene expression, which results in an increased number of mRNAs generated from the gene transcription. The enhanced expression of a gene can be achieved by the way of for example, but not limited to: introducing a strong promoter in front of the gene, increasing the copy number of the gene, or enhancing the stability of mRNA etc. As used herein, the term "enhanced activity of a protein encoded by a gene" has the common meaning known in the art, and refers to increased activity of a protein from the gene transcription and translation. It can be achieved by e.g. enhancing the intensity of gene expression, increasing the amount of an enzyme in a cell, and introducing a mutation at an amino acid site. Various technical means used for "enhanced expression of a gene" and "enhanced activity of a protein encoded by a gene" are well known for a person skilled in the art.

In the invention, enhanced expression of a gene can be achieved by e.g. introducing a strong promoter. In some embodiments of the invention, e.g. the strong promoter is selected from the group consisting of Ppck* (SEQ ID No:108) (Zhang et al., 2009b, Appl Environ Microbiol 75:7807-7813), M1-37 (SEQ ID No:109), and M1-93 (SEQ ID No:110) (Lu et al., 2012, Appl Microbiol Biotechnol 93:2455-2426).

In one embodiment, the invention relates to a recombinant *E. coli*, wherein the *E. coli* comprises one or more of the following modifications: (a) enhanced expression of the gene(s) involved in pentose phosphate pathway (PPP), and/or enhanced activity of the protein(s) encoded by the gene(s) involved in pentose phosphate pathway (PPP); (b) enhanced expression of sthA gene, and/or enhanced activity of the protein encoded by sthA gene; and (c) a mutant lpdA gene, the polypeptide encoded by which comprises modification(s) at one or more positions corresponding to the positions T81, P275, and A358 of the amino acid sequence shown in SEQ ID No:1, wherein the corresponding positions are determined by aligning the sequence of the polypeptide with SEQ ID No:1, optionally wherein at the position corresponding to T81, T is replaced with I; at the position corresponding to P275, P is replaced with S; and at the position corresponding to A358, A is replaced with V. In one preferred embodiment, in the *E. coli* of the invention, the expression of the mutant lpdA gene is enhanced, and/or the activity of the protein encoded by said mutant lpdA gene is enhanced.

The terms "mutation", "mutant" and "mutated" have the common meanings known in the art, and refer to insertion, addition, deletion, or replacement of one or more nucleotides in a nucleotide sequence, or refers to insertion, addition, deletion, or replacement of one or more amino acids in a polypeptide sequence.

In one embodiment, the *E. coli* of the invention comprises a mutant lpdA gene, and said mutant lpdA gene is in a plasmid or in a chromosome.

In one embodiment, the *E. coli* of the invention comprises a mutant lpdA gene, and said mutant lpdA gene is in a chromosome.

In one embodiment, the *E. coli* of the invention comprises a mutant lpdA gene, and said mutant lpdA gene is in a plasmid.

As used herein, the term "plasmid" has a definition well known in the art, which is a non-chromosome DNA existing in a cell in episome form, and is a DNA molecule that can self-replicate. The plasmid that is useful in the invention comprises e.g. pEASY-Blunt, pACYC184, pTrc99A, pTrc99A-M, pTrc99A-M-Kan, pKD4, and pKD46 etc.

As used herein, the term "chromosome" has a definition well known in the art. In some embodiments, the modified gene according to the invention is in a chromosome. The techniques that integrate a modified gene into a chromosome are well known to a person skilled in the art, e.g. see Michael R. Green and Joseph Sambrook, "Molecular Cloning: A Laboratory Manual" (Fourth Edition).

lpdA gene (Genbank No: ACA79157.1) is a gene encoding lipoamide dehydrogenase (EC No: 1.8.1.4). In one embodiment of the invention, in the used starting *E. coli* strain, the nucleotide sequence of the wild-type lpdA gene is set forth in SEQ ID No:2, and the amino acid sequence of the polypeptide encoded by it is set forth in SEQ ID No:1. The mutant lpdA gene introduced into the *E. coli* of the invention contains one or more of the mutations C242T, C823T, and C1073T; and said polypeptide encoded by the mutant lpdA gene comprises one or more of the amino acid replacements T81I, P275S and A358V (see FIG. 8).

In one embodiment, the *E. coli* of the invention comprises a mutant lpdA gene, the polypeptide encoded by which comprises modification(s) at one or more positions corresponding to the positions T81, P275, and A358 of the amino acid sequence shown in SEQ ID No:1, wherein the corresponding positions are determined by aligning the sequence of the polypeptide with SEQ ID No:1, optionally wherein at the position corresponding to T81, T is replaced with I, at the position corresponding to P275, P is replaced with S, and at the position corresponding to A358, A is replaced with V. In one preferred embodiment, in the *E. coli* of the invention, the expression of the mutant lpdA gene is enhanced, and/or the activity of the protein encoded by said mutant lpdA gene is enhanced.

In one embodiment, the *E. coli* of the invention comprises a mutant lpdA gene, comprising modifications at one or more positions corresponding to the positions C242, C823, and C1073 of the nucleotide sequence shown in SEQ ID No:2, wherein the corresponding positions are determined by aligning the sequence of the gene with SEQ ID No:2, optionally wherein all the mutations are replacements of C with T. In one preferred embodiment, in the *E. coli* of the invention, the expression of the mutant lpdA gene is enhanced, and/or the activity of the protein encoded by said mutant lpdA gene is enhanced.

A person skilled in the art will understand that, the lpdA gene sequence of different *E. coli* strains may be not completely identical to the lpdA gene sequence as shown in SEQ ID No:2, and the polypeptide sequences encoded by lpdA genes from different *E. coli* strains may be not completely identical to the polypeptide sequence as shown in SEQ ID No:1. In some embodiments of the invention, said mutations in the mutant lpdA gene are at positions C242, 823 and/or 1073 of SEQ ID No:2. In some embodiments of the invention, the replacements in the polypeptide encoded by the mutant lpdA gene are at positions corresponding to positions 81, 275 and/or 358 of SEQ ID No:1.

In the invention, a position "corresponding to" a specific position in SEQ ID No:1 or SEQ ID No:2 can be determined by sequence alignment, e.g. using manual alignment or various available alignment programs (e.g. BLASTP) as well as other methods known to a person skilled in the art. By aligning polypeptide or nucleotide sequences, a person skilled in the art can introduce corresponding mutation(s) at proper position(s), so as to achieve the technical effects of the invention. Besides, a person skilled in the art can also replace amino acid residue(s) at corresponding position(s) with conserved or similar amino acid residue(s), or introduce synonymous mutation(s) into the lpdA gene sequence, so as to achieve the technical effects of the invention.

In one embodiment, the invention relates to a recombinant *E. coli*, in which the expressions of sthA and tktA genes are enhanced, and/or the activities of the proteins encoded by sthA and tktA genes are enhanced.

In one embodiment, the invention relates to a recombinant *E. coli*, comprising the genetic modifications of (a) enhanced expression of the gene(s) involved in pentose phosphate pathway (PPP), and/or enhanced activity of the protein(s) encoded by the gene(s) involved in pentose phosphate pathway (PPP); (b) enhanced expression of sthA gene, and/or enhanced activity of the protein encoded by sthA gene; and (c) a mutant lpdA gene, the polypeptide encoded by which comprises modification(s) at one or more positions corresponding to the positions T81, P275, and A358 of the amino acid sequence shown in SEQ ID No:1, wherein the corresponding positions are determined by aligning the sequence of the polypeptide with SEQ ID No:1, optionally wherein at the position corresponding to T81, T is replaced with I, at the position corresponding to P275, P is replaced with S, and at the position corresponding to A358, A is replaced with V. In one preferred embodiment, in the *E. coli* of the invention, the expression of the mutant lpdA gene is enhanced, and/or the activity of the protein encoded by said mutant lpdA gene is enhanced.

In another embodiment, the *E. coli* of the invention comprises a mutant lpdA gene, the polypeptide encoded by which comprises modifications at the positions corresponding to the positions T81, P275, and A358 of the amino acid sequence shown in SEQ ID No:1, wherein the corresponding positions are determined by aligning the sequence of the polypeptide with SEQ ID No:1, optionally wherein at the position corresponding to T81, T is replaced with I, at the position corresponding to P275, P is replaced with S, and at the position corresponding to A358, A is replaced with V. In one preferred embodiment, in the *E. coli* of the invention, the expression of the mutant lpdA gene is enhanced, and/or the activity of the protein encoded by said mutant lpdA gene is enhanced.

In one embodiment, in the *E. coli* of the invention, the mutant lpdA gene comprises modifications at the positions corresponding to the positions C242, C823, and C1073 of the nucleotide sequence shown in SEQ ID No:2, wherein the corresponding positions are determined by aligning the sequence of the gene with SEQ ID No:2, and optionally wherein all the mutations are the replacement of C with T. In one preferred embodiment, in the *E. coli* of the invention, the expression of the mutant lpdA gene is enhanced, and/or the activity of the protein encoded by said mutant lpdA gene is enhanced.

In one embodiment, the invention relates to a recombinant *E. coli*, comprising the following genetic modifications of (a) enhanced expression of the gene(s) involved in pentose phosphate pathway (PPP), and/or enhanced activities of the protein(s) encoded by the gene(s) involved in pentose phosphate pathway (PPP); (b) enhanced expression of sthA gene, and/or enhanced activity of the protein encoded by sthA gene; and (c) a mutant lpdA gene, the polypeptide encoded by which comprises modifications at the positions corresponding to the positions T81, P275, and A358 of the amino acid sequence shown in SEQ ID No:1, wherein the corresponding positions are determined by aligning the sequence of the polypeptide with SEQ ID No:1, optionally wherein at the position corresponding to T81, T is replaced with I, at the position corresponding to P275, P is replaced with S, and at the position corresponding to A358, A is replaced with V. In one preferred embodiment, in the *E. coli* of the invention, the expression of the mutant lpdA gene is enhanced, and/or the activity of the protein encoded by said mutant lpdA gene is enhanced.

In one embodiment, the invention relates to a recombinant *E. coli*, comprising the modifications of (a) enhanced expression of tktA gene, and/or enhanced activity of the protein encoded by tktA gene, (b) enhanced expression of sthA gene, and/or enhanced activity of the protein encoded by sthA gene, and (c) a mutant lpdA gene, comprising modifications at positions corresponding to the positions C242, C823, and C1073 of the nucleotide sequence shown in SEQ ID No:2, wherein the corresponding positions are determined by aligning the sequence of the gene with SEQ ID No:2, and optionally wherein all the modifications are the replacement of C with T. In one preferred embodiment, in the E. coli of the invention, the expression of the mutant lpdA gene is enhanced, and/or the activity of the protein encoded by said mutant lpdA gene is enhanced.

In one embodiment, the E. coli of the invention further comprises one or more of the modifications of (1) inhibited expression of the gene(s) involved in phosphoenolpyruvate:sugar phosphotransferase system (PTS), and/or inhibited activity of the protein(s) encoded by the gene(s) involved in phosphoenolpyruvate:sugar phosphotransferase system (PTS); (2) inhibited expression of pflB and/or adhE genes, and/or inhibited activities of the proteins encoded by pflB and/or adhE genes; (3) inhibited expression of ldhA gene, and/or inhibited activity of the protein encoded by ldhA gene; (4) enhanced expression of galP gene and/or exogenous glf gene, and/or enhanced activities of the proteins encoded by galP gene and/or exogenous glf gene; and (9) enhanced expression of pck gene, and/or enhanced activity of the protein encoded by pck gene.

In one embodiment, the E. coli of the invention comprises inhibited expression of the gene(s) involved in phosphoenolpyruvate:sugar phosphotransferase system (PTS), and/or inhibited activities of the protein(s) encoded by the gene(s) involved in phosphoenolpyruvate: sugar phosphotransferase system (PTS), wherein said gene is one or more genes selected from the group consisting of the genes ptsI encoding PTS system enzyme I, ptsH encoding PTS system enzyme Hpr, crr encoding PTS system enzyme IIA$^{Glc}$ and ptsG encoding PTS system enzyme IICB$^{Glc}$.

In the invention, ptsI gene (GenBank No: ACA76928.1, NC_010468.1) encodes phosphoenolpyruvate-phosphosugar transferase I (EC No: 2.7.3.9), ptsH gene (GenBank No: ACA76929.1) encodes phosphoenolpyruvate-phosphosugar transferase Hpr (EC No: 2.7.1.69), crr gene (GenBank No: ACA76927.1) encodes phosphoenolpyruvate-phosphosugar transferase IIA$^{Glc}$ (EC No: 2.7.1.69) and ptsG gene (GenBank No: ACA78131.1) encodes phosphoenolpyruvate-phosphosugar transferase IICB$^{Glc}$ (EC No: 2.7.1.69).

In one embodiment, the E. coli of the invention further comprises one or more of the modifications of (1) inhibited expression of ptsI gene, and/or inhibited activity of the protein encoded by ptsI gene; (2) inhibited expression of pflB and/or adhE genes, and/or inhibited activities of the proteins encoded by pflB and/or adhE genes; (3) inhibited expression of ldhA gene, and/or inhibited activity of the protein encoded by ldhA gene; (4) enhanced expression of galP gene and/or exogenous glf gene, and/or enhanced activities of the proteins encoded by galP gene and/or exogenous glf gene; and (9) enhanced expression of pck gene, and/or enhanced activity of the protein encoded by pck gene.

In one embodiment, the E. coli of the invention further comprises one or more of the modifications of (1) inhibited expression of ptsI gene, and/or inhibited activity of the protein encoded by ptsI gene; (2) inhibited expression of pflB and/or adhE genes, and/or inhibited activities of the proteins encoded by pflB and/or adhE genes; (3) inhibited expression of ldhA gene, and/or inhibited activity of the protein encoded by ldhA gene; (4) enhanced expression of galP gene, and/or enhanced activity of the protein encoded by galP gene; and (9) enhanced expression of pck gene, and/or enhanced activity of the protein encoded by pck gene.

In one embodiment, the E. coli of the invention further comprises one or more of the modifications of (1) inhibited expression of ptsI gene, and/or inhibited activity of the protein encoded by ptsI gene; (2) inhibited expression of pflB gene, and/or inhibited activity of the protein encoded by pflB gene; (3) inhibited expression of ldhA gene, and/or inhibited activity of the protein encoded by ldhA gene; (4) enhanced expression of galP gene, and/or enhanced activity of the protein encoded by galP gene; and (9) enhanced expression of pck gene, and/or enhanced activity of the protein encoded by pck gene.

In one embodiment, the E. coli of the invention further comprises the modifications of (1) inhibited expression of ptsI gene, and/or inhibited activity of the protein encoded by ptsI gene; (2) inhibited expression of pflB gene, and/or inhibited activity of the protein encoded by pflB gene; (3) inhibited expression of ldhA gene, and/or inhibited activity of the protein encoded by ldhA gene; (4) enhanced expression of galP gene, and/or enhanced activity of the protein encoded by galP gene; and (9) enhanced expression of pck gene, and/or enhanced activity of the protein encoded by pck gene.

In the invention, pflB gene (GenBank No: ACA78322.1) encodes pyruvate formate lyase (EC No. 2.3.1.54), adhE gene (Genbank No: ACA78022.1) encodes ethanol/acetaldehyde dehydrogenase (EC No: 1.1.1.1, EC No: 1.2.1.10), ldhA gene (GenBank No: ACA77176.1) encodes lactate dehydrogenase A (EC No: 1.1.1.28), galP gene (GenBank No: ACA76443.1) encodes galactose MFS transporter, glf gene (GenBank No: AAA27691.1) encodes glucose transporter Glf (glucose facilitator protein) and pck gene (GenBank No: ACA75988.1) encodes phosphoenolpyruvate carboxykinase, also called PCK enzyme (EC No: 4.1.1.49).

As used herein, the term "inhibited expression of a gene" has the common meanings known in the art, and refers to the decrease in the intensity of the expression of a gene, leading to the reduced amount of mRNAs from gene transcription. The inhibited expression of a gene can be achieved by the ways of, for example but not limited to: deleting a gene, reducing gene copy number, changing gene promoter (e.g. using a weak promoter) etc. As used herein, the term "inhibited activity of a protein encoded by a gene" has the common meanings known in the art, and refers to the decrease in the activity of a protein encoded by a gene. It can be achieved by, e.g. decreasing the intensity of gene expression, inserting or deleting a nucleotide in a gene, and mutating an amino acid site. Various technical means for achieving the "inhibited expression of a gene" and "inhibited activity of a protein encoded by a gene" are well known for a person skilled in the art.

In another embodiment, the E. coli of the invention further comprises the modifications of (1) inhibited expression of ptsI gene, and/or inhibited activity of the protein encoded by ptsI gene; (2) inhibited expression of pflB gene, and/or inhibited activity of the protein encoded by pflB gene; (3) inhibited expression of ldhA gene, and/or inhibited activity of the protein encoded by ldhA gene; and (4) enhanced expression of galP gene, and/or enhanced activity of the protein encoded by galP gene.

In one embodiment, the E. coli of the invention also comprises the modifications of (5) inhibited expression of ackA and pta genes, and/or inhibited activities of the proteins encoded by ackA and pta genes; (6) enhanced expression of aceBA gene cluster, and/or enhanced activity of the protein(s) encoded by aceBA gene cluster; (7) enhanced expression of dcuC gene cluster, and/or enhanced activity of the proteins encoded by dcuC gene cluster; and (8) inhibited expression of mgsA gene, and/or inhibited activity of the protein encoded by mgsA gene.

In one embodiment, the *E. coli* of the invention also comprises the modifications of (9) enhanced expression of pck gene, and/or enhanced activity of the protein encoded by pck gene. In another embodiment, pck gene in the *E. coli* of the invention is deleted.

Pta gene (GenBank No: ACA77021.1) encodes acetyl transferase (EC No: 2.3.1.8), and ackA gene (GenBank No: ACA77022.1) encodes acetokinase (EC No: 2.7.2.1). AceBA gene cluster comprises aceB gene (GenBank No: ACA79615.1) encoding malate synthetase (EC No: 2.3.3.9) and aceA gene (GenBank No: ACA79614.1) encoding isocitrate lyase (EC No: 4.1.3.1). DcuC gene (GenBank No: ACA78647.1) encodes C4 dicarboxylate transporter DcuC. MgsA gene (GenBank No: ACA78263.1) encodes methylglyoxal synthetase (EC No: 4.2.3.3).

In one embodiment, the *E. coli* of the invention further comprises the modifications of (10) inhibited expression of adhE gene, and/or inhibited activity of the protein encoded by adhE gene; and (11) inhibited expression of tdcDE gene cluster, and/or inhibited activity of the protein(s) encoded by tdcDE gene cluster.

TdcDE gene cluster comprises tdcD gene (GenBank No:ACA76259.1) and tdcE gene (GenBank No: ACA76260.1), wherein tdcD gene encodes propionate kinase (EC No: 2.7.2.15) and tdcE gene encodes 2-keto methyl butyrate lyase/methyl propionate lyase (EC No: 2.3.1.54). AdhE gene (GenBank No: ACA78022.1) encodes ethanol/acetaldehyde dehydrogenase (EC No: 1.1.1.1/EC No: 1.2.1.10).

In one embodiment, the *E. coli* of the invention further comprises one or more of the modifications of (12) enhanced expression of aceEF gene cluster, and/or enhanced activity of the protein(s) encoded by aceEF gene cluster; (13) enhanced expression of dcuB gene, and/or enhanced activity of the protein encoded by dcuB gene; (14) enhanced expression of mdh gene, and/or enhanced activity of the protein encoded by mdh gene; (15) enhanced expression of fumA gene, and/or enhanced activity of the protein encoded by fumA gene; (16) enhanced expression of fumB gene, and/or enhanced activity of the protein encoded by fumB gene; and (17) enhanced expression of frdABCD gene cluster, and/or enhanced activity of the protein(s) encoded by frdABCD gene cluster.

AceEF gene cluster encode pyruvate complex E1/E2(EC No: 1.2.4.1), including aceE gene (GenBank No: ACA79159.1) encoding pyruvate dehydrogenase complex E1 and aceF gene (GenBank No: ACA79158.1) encoding pyruvate dehydrogenase complex E2. DcuB gene (GenBank No: ACA79506.1) encodes anaerobic C4 dicarboxylate transporter DcuB. Mdh gene (GenBank No: ACA76147.1) encodes malate dehydrogenase (EC No: 1.1.1.37). FumA gene (GenBank No: ACA77662.1) encodes aerobic fumarase enzyme I (EC No: 4.2.1.2). FumB gene (GenBank No: ACA79507.1) encodes anaerobic fumarase enzyme I (EC No: 4.2.1.2). FrdABCD gene cluster encode fumarate reductase (EC No: 1.3.5.4), including frdA gene (GenBank No: ACA79460.1) encoding fumarate reductase flavoprotein subunit, frdB gene (GenBank No: ACA79461.1) encoding fumarate reductase iron-sulphur protein subunit, frdC gene (GenBank No: ACA79462.1) encoding fumarate reductase subunit C, and frdD gene (GenBank No: ACA79463.1) encoding fumarate reductase subunit D.

In one embodiment, the *E. coli* of the invention is deposited in CGMCC on Feb. 25, 2013 under the deposition No. of CGMCC 7260 (Institute of Microbiology of Chinese Academy of Sciences, NO. 1 Beichen West Road, Chaoyang District, Beijing).

In one embodiment, the *E. coli* of the invention is deposited in CGMCC on Feb. 25, 2013 under the deposition No. of CGMCC 7259 (Institute of Microbiology of Chinese Academy of Sciences, NO. 1 Beichen West Road, Chaoyang District, Beijing).

In one embodiment, the *E. coli* of the invention is deposited in CGMCC on May 3, 2013 under the deposition No. of CGMCC 7550 (Institute of Microbiology of Chinese Academy of Sciences, NO. 1 Beichen West Road, Chaoyang District, Beijing).

In second aspect, the invention provides a method for producing succinate, comprising the step of culturing the *E. coli* of the invention.

In one embodiment, the method for producing succinate of the invention comprises culturing the *E. coli* of the invention, and optionally collecting or purifying succinate.

In one embodiment, the "culturing" of the invention includes seed culture and fermentation culture.

As used herein, the term "seed culture" refers to a process of scaling up in shaking flask and seed tank, after activating a bacterial strain for fermentation on a solid medium, so as to obtain a certain amount and quality of pure seed.

As used herein, the term "fermentation culture" refers to a process of: converting the components of a medium into some specific products through particular metabolic pathway(s) by using a microbe strain under appropriate conditions.

In one embodiment, the method of the invention comprises performing anaerobic fermentation of the *E. coli* of the invention.

As used herein, the term "anaerobic fermentation" refers to a process of converting the components of a medium into some specific products through particular metabolic pathway(s) by using an anaerobic fermentation bacterial strain under an anoxic condition.

In one embodiment, the culture process in the method of the invention does not involve any aeration step.

In one embodiment, the method of the invention for culturing *E. coli* comprises the following steps:

(1) inoculating the recombinant *E. coli* of the invention into a seed medium, and culturing under conditions appropriate for *E. coli* growth for a period to obtain a seed solution;

(2) inoculating the seed solution into a fermentation medium, and culturing under an anaerobic condition.

In the method of the invention, various conventional culturing conditions for *E. coli* can be used, such as medium, culture temperature, culture time period, and whether using a shaker as well as the shaking speed etc. A person skilled in the art can choose proper conditions based one the requirements. The culturing and fermentation conditions used in the method of the invention are well known for a person skilled in the art (Zhuge jian et al., 1994, *Industrial Microbiology Experimental Techniques Manual*, China Light Industry Press).

In one embodiment, the culturing condition of the invention includes but not limited to: a temperature of 30-45° C., e.g. 30-31° C., 31-32° C., 32-33° C., 33-34° C., 34-35° C., 35-36° C., 36-37° C., 37-38° C., 38-39° C., 39-40° C., 40-41° C., 41-42° C., 42-43° C., 43-44° C., or 44-45° C.

In one embodiment, the culturing condition of the invention includes but not limited to: a time period for seed culture of 6-16 hours, e.g. 6-7 hours, 7-8 hours, 8-9 hours, 9-10 hours, 10-11 hours, 11-12 hours, 12-13 hours, 13-14 hours, 14-15 hours, or 15-16 hours.

In one embodiment, the culturing condition of the invention includes but not limited to: a time period for fermentation culture of 2-5 days, e.g. 2 days, 3 days, 4 days, or 5 days.

In one embodiment, the culturing condition of the invention includes but not limited to: inoculating the recombinant E. coli of the invention into a seed medium at an inoculation amount of 0.1-10% (V/V), e.g. 0.1%, 0.5%, 1%, 2.5%, 5%, or 10%.

In one embodiment, the culturing condition of the invention includes but not limited to: inoculating the seed solution into a fermentation medium at an inoculation amount of a final concentration of $OD_{550}$=0.05-0.5, e.g. 0.05-0.1, 0.1-0.2, 0.2-0.3, 0.3-0.4, or 0.4-0.5.

In one embodiment, any medium commonly used for E. coli can be used. The medium used for the E. coli of the invention can comprise a proper nitrogen source, e.g. organic nitrogen compounds, or inorganic nitrogen compounds, or mixtures thereof. In one embodiment, said organic nitrogen compound can be e.g. selected from one or a mixture of: soybean meal, peanut meal, beef extract, fish meal, yeast extract, peptone, and corn steep liquor; and said inorganic nitrogen compound can be e.g. selected from one or a mixture of: nitrate salt (such as sodium nitrate, potassium nitrate, calcium nitrate), ammonium salt (such as ammonium phosphate, ammonium sulfate, ammonium nitrate, ammonium chloride). In one embodiment, the medium used for the E. coli of the invention can comprise a proper carbon source, e.g. selected from one or a mixture of: glucose, starch, saccharine generated from amylohydrolysis, fructose, dextrin, lactose, galactose, xylose, sucrose, glycerol, maltose, fatty acid, acetate, pyruvate, and fumarate.

In one embodiment, the seed medium and the fermentation medium used in the method of the invention are composed of (using water as solvent):

major elements: glucose, $KH_2PO_4$, $K_2HPO_4$, $(NH_4)_2HPO_4$, $MgSO_4.7H_2O$, and betaine-KCl; and trace elements: $FeCl_3.6H_2O$, $CoCl_2.6H_2O$, $CuCl_2.2H_2O$, $ZnCl_2$, $Na_2MoO_4.2H_2O$, $MnCl_2.4H_2O_2$, and $H_3BO_3$.

In one embodiment, the medium of the invention is composed of (using water as solvent):

major elements: glucose 20-120 g/L, $KH_2PO_4$ 2-5 g/L, $K_2HPO_4$ 4-8 g/L, $(NH_4)_2HPO_4$ 3-5 g/L, $MgSO_4.7H_2O$ 0.1-0.3 g/L, and betaine-KCl 0.1-1 g/L; and trace elements: $FeCl_3.6H_2O$ 1-5 µg/L, $CoCl_2.6H_2O$ 0.05-1 µg/L, $CuCl_2.2H_2O$ 0.05-1 µg/L, $ZnCl_2$ 0.05-1 µg/L, $Na_2MoO_4.2H_2O$ 0.05-1 µg/L, $MnCl_2.4H_2O_2$ 0.1-1 µg/L, $H_3BO_3$ 0.01-0.5 µg/L.

In one embodiment, the seed medium and the fermentation medium used in the method of the invention are composed of (using water as solvent):

major elements: glucose, $NH_4H_2PO_4$, $(NH_4)_2HPO_4$, $MgSO_4.7H_2O$, and betaine-KCl; and trace elements: $FeCl_3.6H_2O$, $CoCl_2.6H_2O$, $CuCl_2.2H_2O$, $ZnCl_2$, $Na_2MoO_4.2H_2O$, $MnCl_2.4H_2O_2$, and $H_3BO_3$.

In one embodiment, the medium of the invention is composed of (using water as solvent):

major elements: glucose 20-120 g/L, $NH_4H_2PO_4$ 0.5-1.5 g/L, $(NH_4)_2HPO_4$ 2-5 g/L, $MgSO_4.7H_2O$ 0.1-0.3 g/L, and betaine-KCl 0.1-1 g/L; and trace elements: $FeCl_3.6H_2O$ 1-5 µg/L, $CoCl_2.6H_2O$ 0.05-1 µg/L, $CuCl_2.2H_2O$ 0.05-1 µg/L, $ZnCl_2$ 0.05-1 µg/L, $Na_2MoO_4.2H_2O$ 0.05-1 µg/L, $MnCl_2.4H_2O_2$ 0.1-1 µg/L, $H_3BO_3$ 0.01-0.5 µg/L.

In one embodiment, the method of the invention for culturing E. coli comprises:

a step of anaerobic fermentation of a bacterial strain, comprising:

(1) seed culture: taking ⅓-½ volume of seed medium into a triangular flask, and autoclaving for sterilization; after cooling down, inoculating the recombinant E. coli of the invention at a inoculation amount of 0.1-10% (V/V) into a seed medium, and culturing at 37° C. for 6-16 hours under shaking to obtain a seed solution for inoculating the fermentation medium;

(2) fermentation culture: taking ⅓-½ volume of the fermentation medium into an anaerobic fermentation vessel, inoculating the seed solution into the fermentation medium at an inoculation amount of a final concentration of $OD_{550}$=0.05-0.5, and culturing at 37° C. for 2-5 days, to obtain a fermentation broth.

In one embodiment, the method of the invention for producing succinate further comprises a step of isolating and/or purifying succinate from the fermentation broth.

In third aspect, the invention relates to use of the E. coli of the invention in the production of succinate.

EXAMPLES

The invention is further illustrated through the following examples, but any example or combination thereof should not be construed as limiting the scope or embodiment of the invention. The scope of the invention is defined by the attached claims, and based on the present specification and common knowledge in the art, a person skilled in the art can clearly understand the scope as defined by the claims. Without departure of the spirit and scope of the invention, a person skilled in the art can make any modifications or changes to the technical solutions of the invention, and such modifications or changes are also within the scope of the invention.

The experimental processes used in the following examples are all conventional processes, unless otherwise indicated. The material, reagents etc. used in the following examples are all commercially available, unless otherwise indicated.

The invention specifically comprises the following examples.

Example 1: Construction of Recombinant E. coli NZ-037 Strain

The construction of recombinant E. coli NZ-037 (Table 1) included the following eight steps:

(1) Deletion of lactate dehydrogenase gene ldhA (1-1) Plasmid pXZ-CS was firstly constructed for gene deletion, modulation and integration.

Four steps were applied to construct plasmid pXZ-CS: First step, a chloramphenicol resistance gene was amplified by using the plasmid pACYC184 DNA (Mok et al., 1991. Nucleic acids Res 19:2321-2323) as template with primer set 184-cat-up (SEQ ID No:7) and 184-cat-down (SEQ ID No:8). The resulting PCR product with 994 bp was designated as fragment I, containing the chloramphenicol gene promoter sequence.

PCR system: 10 µl of New England Biolabs Phusion 5× buffer, 1 µl of dNTP (each dNTP, 10 mM), 20 ng of DNA template, and primer set (each of 10 μM), 0.5 μl of Phusion High-Fidelity DNA polymerase (2.5 U/μL), 33.5 μl of distilled water, in 50 μl of total volume.

PCR cycles: 1 cycle of 98° C. for 2 minutes (pre-denaturing); 30 cycles of 98° C. for 10 seconds (denaturing), 56° C. for 10 seconds (annealing), and 72° C. for 30 seconds (extension); 1 cycle of 72° C. for 5 minutes (extension).

Second step, a levansucrase gene (sacB) was amplified by using the chromosome DNA from *Bacillus subtilis* sp *subtilis* 168 (China General microbiological culture collection center, China. CGMCC No. 1.1390) as template with primer set Bs-sacB-up (SEQ ID No:9) and Bs-sacB-down (SEQ ID No:10). The resulting PCR product with 1618 bp was designated as fragment II, containing sacB gene promoter sequence. The PCR system and cycles were referred to the first step described above.

Third step, fragment I obtained in the first step and fragment II obtained in the second step were digested with restriction endonuclease SacI (NEB) at 37° C. for 30 minutes. The digested products were cleaned using Purification Kit Cleaning Gel/PCR Extraction kit (BioMIGA Biotechnology Company). Each 20 ng of fragments I and fragment II were added with 1 μl of 10× T4-DNA ligase buffer solution (NEB) and 1 μl of T4-DNA ligase (NEB), supplemented with distilled water to a total volume of 10 μl and reacted at 25° C. for 5 minutes. Taking 1 μl of ligation product as template, fragment III containing cat-sacB cassette was amplified with a primer set 184-cat-up/Bs-sacB-down. The PCR system and Cycles was referred to the first step described above.

Fourth step, 1 μl of fragment III obtained from PCR was added into 1 μl of pEASY-blunt simple vector (Beijing TransGen Biotech, China) and allowed for reaction at 25° C. for 15 min. CaCl₂ transformation: adding 50 μl of Trans10 Competent Cells (Beijing TransGen Biotech, China) and in ice-bath for 30 min; heat shocking at 42° C. for 30 seconds, and immediately transferring on ice for 2 minutes. Adding 250 μl of LB medium and incubating at 37° C., 200 rpm for 1 hour. 200 μl of transformed competent cells were plated onto a LB plate containing ampicillin (final concentration of 100 μg/mL) and chloramphenicol (final concentration of 34 μg/mL), and grown overnight. 5 positive colonies were verified by colony PCR with primer set M13-F (SEQ ID No:11)/M13-R (SEQ ID No:12) and sequencing. The plasmid from the correct one was designated as pXZ-CS (Table 3).

(1-2): Deletion of ldhA gene from *E. coli* ATCC 8739 (Gunsalus et al., 1941, J Biol Chem 141:853-858) by dual-phase homologous recombination to obtain *E. coli* Suc-T102, including the following six steps.

First step, taking genomic DNA of *E. coli* ATCC 8739 as template, a PCR product of 1753 bp was amplified with a primer set XZ-ldhA-up (SEQ ID No:13)/XZ-ldhA-down (SEQ ID No:14). The PCR product with 1753 bp contained lactate dehydrogenase gene ldhA (GenBank accession No: ACA77176.1) of *E. coli* ATCC 8739 and its upstream and downstream sequences of about 400 bp. The PCR system and cycles were referred to first step in section (1-1) of Example 1 as described above.

The amplified PCR product of 1753 bp was cloned into the pEASY-Blunt cloning vector (Beijing TransGen Biotech). The cloning system and calcium chloride transformation were referred to the fourth step in the above section (1-1) for the construction of plasmid pXZ-CS. 200 μl of transformed competent cells were plated onto a LB plate containing kanamycin (final concentration of 15 μg/ml), and grown for overnight. 5 positive colonies were verified by colony PCR with a primer set M13-F/M13-R and sequenced, and the plasmid from the correct one was designated as pXZ-001.

Second step, PCR amplification was carried out by using the DNA of the plasmid pXZ001 as template with primer set XZ-ldhA-1 (SEQ ID No:15) and XZ-ldhA-2 (SEQ ID No:16), and the PCR product of 4758 bp was obtained containing pEASY-Blunt vector as well as each of the upstream and downstream sequences of ldhA gene of about 400 bp. The PCR system and cycles were referred to the first step in the above section (1-1).

Third step, the DNA fragment cat-sacB containing chloramphenicol gene (cat) and levansucrase gene (sacB) was ligated into the PCR amplified product of the second step. The details were as follows:

Taking pXZ-CS as template, a PCR product of 2618 bp was amplified with a primer set cat-sacB-up (SEQ ID No:17)/cat-sacB-down (SEQ ID No:18), containing chloramphenicol gene (cat) and levansucrase gene (sacB).

Ligation System: 10 ng of the 4758 bp PCR product obtained in the second step, 30 ng of the cat-sacB cassette DNA fragment and 2 μl of 10× T4 DNA ligation buffer (NEB), 1 μl of T4 ligase (NEB, 400,000 cohesive end units/mL), and distilled water were added to a final total volume of 20 μl. The ligation was at room temperature for 2 hours. 10 μl of ligation reaction was transformed into Trans10 by CaCl₂ transformation method, referring to the fourth step described in the above section (1-1) for construction of plasmid pXZ-CS. 200 μl of the transformed competent cells were plated onto a LB plate containing chloramphenicol (final concentration of 17 μg/mL), and grown for overnight. 5 positive single colonies were picked up and cultured in liquid medium, and the plasmid (cat-sacB DNA fragment was cloned into the plasmid pXZ001) was validated by sequencing. The sequencing results showed that cat-sacB DNA fragment was ligated to the PCR product in the above second step, demonstrating correct construction of the plasmid and the resulting recombinant plasmid was designated as pXZ002C.

Fourth step, taking plasmid pXZ002C as template, a PCR fragment I (3447 bp) was amplified with a primer set XZ-ldhA-up/XZ-ldhA-down. The PCR system and cycles were referred to the first step in section (1-1) as described above for construction of plasmid pXZ-CS. The DNA fragment I contained 400 bp upstream of lactate dehydrogenase gene ldhA, cat-sacB cassette, and 400 bp downstream of lactate dehydrogenase gene ldhA.

The DNA fragment I was used for the first homologous recombination. Plasmid pKD46 (Wanner and Datsenko 2000, Proc Natl Acad SCI USA 97:6640-6645; plasmid was purchased from Yale University CGSC *E. coli* Depositary Center) was firstly transformed into *E. coli* ATCC 8739 by CaCl₂ transformation, and then the DNA fragment I was electroporated into *E. coli* ATCC 8739 harboring the pKD46.

Electroporation Program: first, electroporation competent cells of *E. coli* ATCC 8739 harboring the pKD46 were prepared by the method described by Dower (Dower et al., 1988. Nucleic Acids Res 16:6127-6145). 50 μl of electroporation competent cells were placed on ice, added with 50 ng of the DNA fragment I, and then placed on ice for 2 minutes. The mixture of the DNA and the cells were transferred into a 0.2 cm MicroPulser Electroporation Cuvette (Bio-Rad). The electric voltage was 2.5 KV by the MicroPulser (Bio-Rad) electroporation apparatus. After shock, 1 mL of LB medium were quickly added into the electroporation cuvette and transferred into a tube after pipetting five times. The culture was incubated at 30° C. with shaking at 75 rpm for two hours. 200 μl of culture was spread onto a LB plate containing chloramphenicol (final concentration of 17 μg/mL), and incubated at 37° C. overnight. 5 colonies were verified by PCR with a primer set XZ-ldhA-up/XZ-ldhA-down. A correct colony was designated as Suc-T101.

Fifth step, the 4758 bp PCR product obtained in the second step was phosphorylated, and the self-ligated plasmid was used for the second homologous recombination. Specifically, the 4758 bp PCR product was cleaned up with Gel/PCR purification Kit (Gel/PCR Extraction Kit, BioMIGA). 20 μl of reaction volume included 30 ng of the purified PCR product, 2 μl of 10× T4 ligation buffer (NEB), 1 μl of T4 polynucleotide kinase (NEB), and remaining distilled water were reacted at 37° C. for 30 minutes. 1 μl of T4 ligase (NEB, 400,000 cohesive end units/ml) was added and reacted at room temperature for 2 hours to obtain ligation product. 10 μl of the ligation product was transformed into Trans10, referring to the fourth step described in the above section (1-1) for construction of plasmid pXZ-CS. 200 μl of transformed competent cells were spread onto a LB plate containing kanamycin (final concentration of 15 μg/mL) and grown overnight. 5 positive colonies were picked up and cultured in liquid medium, and the plasmid was extracted for sequencing. The sequencing results showed the PCR product in the second step was self-ligated, showing correct construction of the plasmid. The correct one was designated as pXZ003.

Sixth step, an 829 bp DNA fragment II was amplified by using the plasmid pXZ003 as template with primer set XZ-ldhA-up/XZ-ldhA-down for second homologous recombination. The DNA fragment II was electroporated into the strain Suc-T101.

Electroporation Program: first, electroporation competent cells of Suc-T101 harboring plasmid pKD46 were prepared by the method described by Dower (Dower et al., 1988). 50 μl of competent cells were placed on ice, added with 50 ng of the DNA fragment II, and then placed on ice for 2 minutes. The mixture of the DNA and cells were transferred into a 0.2 cm MicroPulser Electroporation Cuvette (Bio-Rad). The electric voltage was 2.5 KV applied by the MicroPulser (Bio-Rad) electroporation apparatus. After shock, 1 mL of LB medium was quickly added into the electroporation cuvette and transferred into a tube after pipetting five times. The culture was incubated at 30° C. with shaking at 75 rpm for four hours to remove the plasmid pKD46. The culture was then transferred to LB medium with 10% sucrose but without sodium chloride (50 mL medium in 250 mL flask), cultured for 24 hours and then streaked on LB solid medium with 6% sucrose but without sodium chloride and incubated. The correct colony amplification product was a fragment of 763 bp via PCR with a primer set XZ-ldhA-up/XZ-ldhA-down. A correct colony was designated as Suc-T102 (Table 1).

The plasmids constructed for deleting ldhA gene are listed in Table 3, and the primers used are listed in Table 2.

(2) Deletion of pyruvate formate lyase gene pflB

The pflB gene (GenBank No: ACA78322.1) of the recombinant E. coli Suc-T102 was deleted using the method as described in the above section (1). The resulting strain was designated as Suc-T104. The constructed plasmids are listed in Table 3, and the primers used are listed in Table 2. The primers were named in same manner as those used for deleting the ldhA gene, while only ldhA was replaced by pflB.

(3) Deletion of phosphoenolpyruvate: sugar phosphotransferase I gene ptsI

The ptsI gene (GenBank No: ACA76928.1) of the recombinant E. coli Suc-T104 was deleted using the method as described in the above section (1). The resulting strain was Suc-T106. The constructed plasmids are listed in Table 3, and the primers used are listed in Table 2. The primers were named in same manner as those used for deleting the ldhA gene, while only ldhA was replaced by ptsI.

(4) Activation of galactose MFS transporter GalP

The native promoter of galP gene (GenBank No: ACA76443.1) of the recombinant E. coli Suc-T106 was replaced by the regulatory part Ppck* (SEQ ID No. 108). The resulting strain was designated as Suc-T108. In the invention, Ppck* represented mutated pck promoter of E. coli, G to A transition at position −64 relative to the ATG start codon (Zhang et al., 2009b, Appl Environ Microbiol 75:7807-7813).

Six steps were applied for the processes.

First step, taking genomic DNA of E. coli ATCC 8739 as template, an amplification product of 841 bp was amplified with a primer set XZ-galP-P-up (SEQ ID No:27)/XZ-galP-P-down (SEQ ID No:28), containing galP gene's promoter and its upstream and downstream sequences of about 400 bp. The amplification product was cloned into pEASY-Blunt vector. The plasmid of the positive colonies was extracted for sequencing. The sequencing results showed that the promoter of galactose transporter gene galP and its upstream and downstream sequences of about 400 bp were inserted into the plasmid pEASY-Blunt, showing correct construction of the plasmid. The resulting recombinant plasmid was designated as pXZ011.

Second step, taking DNA of plasmid pXZ011 as template, an amplification product of 4614 bp was amplified with a primer set XZ-galP-P-1 (SEQ ID No:29)/XZ-galP-P-2 (SEQ ID No:30). The resulting amplification product contained the sequence of pEASY-Blunt vector, the promoter of galP gene and its upstream and downstream sequences of approximate 400 bp.

Third step, taking plasmid pXZ-CS as template, a PCR product of 2618 bp was amplified with a primer cat-sacB-up/cat-sacB-down, containing chloramphenicol gene (cat) and levansucrase gene (sacB).

The DNA fragment containing chloramphenicol gene (cat) and levansucrase gene (sacB) was ligated into the PCR product of 4614 bp obtained in the second step. The ligation product was transformed into Trans1-T1 Competent Cells. 200 μl of transformed competent cells were plated onto a LB plate containing chloramphenicol (final concentration of 17 μg/mL), and grown for overnight. 5 positive colonies were picked up and cultured in liquid medium, and the plasmid (in which the cat-sacB DNA fragment was cloned into pXZ010) was extracted for sequencing. The results showed that the PCR product in the second step was ligated with the cat-sacB DNA fragment, showing correct construction of the plasmid. The obtained recombinant plasmid was designated as pXZ012C.

Fourth step, taking plasmid pXZ012C as template, DNA fragment I (3303 bp) was amplified with a primer set XZ-galP-P-up/XZ-galP-P-down, containing 400 bp upstream of galP's promoter, cat-sacB cassette, 400 bp downstream of galP's promoter.

DNA fragment I was used for the first homologous recombination. The plasmid pKD46 was transformed to strain Suc-T106 by CaCl$_2$ transformation, and then the DNA fragment I was electroporated to the strain Suc-T106 harboring pKD46.

The electroporation program was referred to the fourth step in the above section (1-2) for deleting ldhA gene. 200 μl of transformed competent cells were plated onto a LB plate containing chloramphenicol (final concentration of 17 μg/mL), and grown at 37° C. for overnight. 5 colonies were verified by PCR using a primer set XZ-galP-P-up/XZ-galP-P-down. The correct one was designated as Suc-T107.

Fifth step, taking genomic DNA of E. coli ATCC 8739 as template, the promoter of pck gene of E. coli ATCC 8739 was amplified with a primer set P-pck*-up-SpeI (SEQ ID No:31)/P-pck*-down-KpnI (SEQ ID No:32). The primers are listed in Table 2. The PCR product was cleaved with SpeI (NEB) and KpnI (NEB), and cloned into the expression vector pTrc99A (Amann et al., 1998, Gene 69:301-15) cleaved with the same enzymes. The resulting plasmid was designated as pXZ602. Taking plasmid pXZ602 as template, the amplification was carried out with a primer set pck*-F (ID No. SEQ: 33)/pck*-R (ID No. SEQ: 34). The primers are listed in Table 2. The amplified product was phosphorylated by T4 polynucleotide kinase (NEB), and then self-ligated, to obtain a positive plasmid for sequencing. The correct one was designated as pXZ603.

Taking pXZ603 as template, a mutated Ppck* of 378 bp was amplified with a primer set P-pck*-up-SpeI/P-pck*-down-KpnI, and ligated into the 4614 bp fragment prepared in the second step, resulting in plasmid pXZ013.

DNA fragment II was amplified from plasmid pXZ013 using a primer set XZ-galP-P-up/XZ-galP-P-down.

Sixth step, DNA fragment II was used in the second homologous recombination. DNA fragment II was electroporated into Suc-T107. The electroporation program was referred to the sixth step as described in the above section (1-2) for deleting ldhA gene. Via PCR with a primer set XZ-galP-P-up/XZ-galP-P-down and sequencing, the correct colonies from which a product of 1051 bp was amplified were obtained which were designated as Suc-T108 (Table 1).

The plasmids used for replacing the promoter of galP by Ppck* are listed in Table 3, and the primers used are listed in Table 2.

(5) Activation of phosphoenolpyruvate carboxykinase PCK

The native promoter of pck gene (GenBank No: ACA75988.1) of Suc-T108 was replaced by the regulatory part Ppck*, resulting in recombinant E. coli Suc-T110 (Table 1), Particularly:

The first homologous recombination: Taking plasmid pXZ-CS as template, DNA fragment I (2717 bp) for the first homologous recombination was amplified with a primer set pck-cat-sacB-up SEQ (ID No:35)/pck-cat-sacB-down (ID No. SEQ: 36). The primers used are listed in Table 2. The DNA fragment I was electroporated into Suc-T108 harboring pKD46. The colonies with ampicillin- and chloramphenicol-resistance were screened out to obtain intermediate recombination bacteria.

The second homologous recombination: taking plasmid pXZ603 as template, the artificial regulatory part Ppck* of 378 bp was amplified with a primer set P-pck*-up-SpeI/P-pck*-down-KpnI (primers are listed in Table 2), and electroporated into the intermediate recombination strain to obtain recombinant bacteria I. A primer set pck-YZ-up (SEQ ID No:37)/pck-YZ-down (SEQ ID No:38) was used for PCR verification of the recombinant bacterium I. The correct colony from which a fragment of 676 bp was amplified and sequenced correctly was designated as Suc-T110.

(6) Deletion of phosphate acetyltransferase gene pta and acetate kinase gene ackA The pta gene (GenBank No: ACA77021.1) and ackA gene (GenBank No: ACA77022.1) were deleted from the recombinant E. coli Suc-T110, using the method as described in section (1) above. The resulting strain was designated as NZ-035 (Table 1). The plasmids constructed are listed in Table 3, and the primers used are listed in Table 2. The primers were named in same manner as those used for deleting the ldhA gene, while only ldhA was replaced by pta or ackA, respectively.

(7) Activation of malate synthase AceA and isocitrate lyase AceB

The native promoter of aceBA gene cluster (aceB GenBank No: ACA79615.1, aceA GenBank No: ACA79614.1) of the recombinant E. coli NZ-035 was replaced by the promoter Ppck*, using the method as described in section (4) above. The resulting strain was designated as NZ-036 (Table 1). The plasmids constructed are listed in Table 3, and the primers used are listed in Table 2. The primers were named in same manner as those used for activating the galP gene, and only galP was replaced by aceB.

(8) Activation of bicarboxylate Dcu transporter DcuC

The native promoter of dcuC gene (GenBank No: ACA78647.1) of the recombinant E. coli NZ-036 was replaced by Ppck*, using the method as described in section (4) above. The resulting strain was designated as NZ-037 (Table 1). The plasmids constructed are listed in Table 3, and the primers used are listed in Table 2. The primers were named in same manner as those used for activating the galP gene, while only galP was replaced by dcuC.

TABLE 1

Recombinant E. coli for producing succinate

| Strain | Relevant characteristics |
|---|---|
| ATCC 8739 | Wild type |
| Suc-T102 | ATCC 8739, ΔldhA |
| Suc-T104 | ATCC 8739, ΔldhA, ΔpflB |
| Suc-T106 | ATCC 8739, ΔldhA, ΔpflB, ΔptsI |
| Suc-T108 | ATCC 8739, ΔldhA, ΔpflB, ΔptsI, Ppck*-galP |
| Suc-T110 | ATCC 8739, ΔldhA, ΔpflB, ΔptsI, Ppck*-galP, Ppck*-pck |
| Suc-T112 | ATCC 8739, ΔldhA, ΔpflB, ΔptsI, Ppck*-pck |
| NZ-035 | ATCC 8739, ΔptsI, ΔldhA, ΔpflB, Ppck*-pck, Ppck*-galP, ΔackA-pta |
| NZ-036 | ATCC 8739, ΔptsI, ΔldhA, ΔpflB, Ppck*-pck, Ppck*-galP, ΔackA-pta, Ppck*-aceBA |
| NZ-037 | ATCC 8739, ΔptsI, ΔldhA, ΔpflB, Ppck*-pck, Ppck*-galP, ΔackA-pta, Ppck*-aceBA, Ppck*-dcuC |
| HX021 | Metabolic evolution of NZ-037 for 1080 generations |
| HX023 | HX021, ΔmgsA |
| HX024 | Metabolic evolution of HX-023 for 360 generations. Deposited in CGMCC with CGMCC 7259 |
| HX026 | HX024, ΔadhE |
| HX027 | HX024, ΔadhE, ΔtdcDE |
| HX028 | Metabolic evolution of HX027 for 650 generations, Deposited in CGMCC with CGMCC 7550 |
| HX041 | HX024, Δpck, Deposited in CGMCC with CGMCC 7260 |
| HX042 | HX024, ΔmaeA |
| HX043 | HX024, ΔmaeB |
| HX044 | HX024, Δppc |
| ZT-251 | Suc-T110, M1-37-tktA |
| ZT-252 | Suc-T110, M1-37-sthA |
| ZT-253 | Suc-T110, M1-37-tktA, M1-37-sthA |
| ZT-273 | ZT-253, M1-93-aceEF, ackA::M1-93-lpdA* |
| NZ-511 | ATCC 8739, ΔldhA, ΔpflB, ΔptsI, Ppck*-galP, Ppck*-pck, ΔadhE |
| NZ-512 | ATCC 8739, ΔldhA, ΔptsI, Ppck*-galP, Ppck*-pck, ΔadhE |
| NZ-513 | ATCC8739, ΔldhA, ΔptsI, Ppck*-galP, Ppck*-pck, ΔadhE, M1-37-tktA |
| NZ-517 | ATCC8739, ΔldhA, ΔptsI, Ppck*-galP, Ppck*-pck, ΔadhE, M1-37-sthA |

TABLE 1-continued

Recombinant *E. coli* for producing succinate

| Strain | Relevant characteristics |
|---|---|
| NZ-514 | ATCC8739, ΔldhA, ΔptsI, Ppck*-galP, Ppck*-pck, ΔadhE, M1-37-tktA, M1-37-sthA |
| ZT-311 | Suc-T110, RBSL1-zwf |
| ZT-312 | Suc-T110, RBSL2-zwf |
| ZT-313 | Suc-T110, RBSL3-zwf |
| ZT-314 | Suc-T110, RBSL4-zwf |
| ZT-321 | Suc-T110, RBSL1-pgl |
| ZT-322 | Suc-T110, RBSL2-pgl |
| ZT-323 | Suc-T110, RBSL3-pgl |
| ZT-324 | Suc-T110, RBSL4-pgl |
| ZT-331 | Suc-T110, RBSL1-gnd |
| ZT-332 | Suc-T110, RBSL2-gnd |
| ZT-333 | Suc-T110, RBSL3-gnd |
| ZT-334 | Suc-T110, RBSL4-gnd |
| ZT-361 | Suc-T110, RBSL1-tktA |
| ZT-362 | Suc-T110, RBSL2-tktA |
| ZT-363 | Suc-T110, RBSL3-tktA |
| ZT-251 | Suc-T110, M1-37-tktA |
| ZT-371 | Suc-T110, RBSL1-talB |
| ZT-372 | Suc-T110, RBSL2-talB |
| ZT-373 | Suc-T110, RBSL3-talB |
| ZT-374 | Suc-T110, RBSL4-talB |

TABLE 2

Primers used in the invention

| Name | Sequences |
|---|---|
| Construction of pXZ-CS | |
| 184-cat-up | GCTAGGTACCTGTGACGGAAGATCACTTCG (SEQ ID No.: 7) |
| 184-cat-down | GCTAGAGCTCGCGGCTATTTAACGACCCT (SacI) (SEQ ID No.: 8) |
| Bs-sacB-up | GCTAGAGCTCAAGTAAATCGCGCGGGTTT (SacI) (SEQ ID No.: 9) |
| Bs-sacB-down | GCTAGGATCCTTATTTGTTAACTGTTAATTGTC (SEQ ID No.: 10) |
| M13-F | GTAAAACGACGGCCAGT (SEQ ID No.: 11) |
| M13-R | CAGGAAACAGCTATGAC (SEQ ID No.: 12) |
| ldhA gene deletion | |
| XZ-ldhA-up | GATAACGGAGATCGGGAATG (SEQ ID No.: 13) |
| XZ-ldhA-down | CTTTGGCTGTCAGTTCACCA (SEQ ID No.: 14) |
| XZ-ldhA-1 | TCTGGAAAAAGGCGAAACCT (SEQ ID No.: 15) |
| XZ-ldhA-2 | TTTGTGCTATAAACGGCGAGT (SEQ ID No.: 16) |
| cat-sacB-up | TGTGACGGAAGATCACTTCGCA (SEQ ID No.: 17) |
| cat-sacB-down | TTATTTGTTAACTGTTAATTGTCCT (SEQ ID No.: 18) |
| pflB gene deletion | |
| XZ-pflB-up | TGTCCGAGCTTAATGAAAAGTT (SEQ ID No.: 19) |
| XZ-pflB-down | CGAGTAATAACGTCCTGCTGCT (SEQ ID No.: 20) |
| XZ-pflB-1 | AAACGGGTAACACCCCAGAC (SEQ ID No.: 21) |
| XZ-pflB-2 | CGGAGTGTAAACGTCGAACA (SEQ ID No.: 22) |
| ptsI gene deletion | |
| XZ-ptsI-up | CGCATTATGTTCCCGATGAT (SEQ ID No.: 23) |
| XZ-ptsI-down | GCCTTTCAGTTCAACGGTGT (SEQ ID No.: 24) |
| XZ-ptsI-1 | CGGCCCAATTTACTGCTTAG (SEQ ID No.: 25) |
| XZ-ptsI-2 | ATCCCCAGCAACAGAAGTGT (SEQ ID No.: 26) |
| Replacing galP promoter with Ppck* | |
| XZ-galP-P-up | ATCTGCTGCACCCGATCTAC (SEQ ID No.: 27) |
| XZ-galP-P-down | GAACCGGCAACAAACAAAT (SEQ ID No.: 28) |
| XZ-galP-P-1 | ATGCCTGACGCTAAAAAACAGGG (SEQ ID No.: 29) |
| XZ-galP-P-2 | GATTAAACGCTGTTATCTGCAA (SEQ ID No.: 30) |
| P-pck*-up-SpeI | GCATACTAGTGTTGGTTATCCAGAATCAAA (SEQ ID No.: 31) |
| P-pck*-down-KpnI | GCATGGTACCAGCCAATATGTATTGCCTGAATAG (SEQ ID No.: 32) |
| pck*-F | ACGGTTAACACCCCCAAAAG (SEQ ID No.: 33) |
| pck*-R | GACAAGGCTCATAGATTTACGTATC (SEQ ID No.: 34) |
| Replacing pck promoter with Ppck* | |
| pck-cat-sacB-up | CGCCATATAAACCAAGATTTAACCTTTTGAGAACATTTTCCACACCTA AGTGTGACGGAAGATCACTTCGCA (SEQ ID No.: 35) |

TABLE 2-continued

Primers used in the invention

| Name | Sequences |
|---|---|
| pck-cat-sacB-down | ATACCATAAGCCTCGAGTTCTTGCGGGGTCAAACCATTGTTAACGCG CATTTATTTGTTAACTGTTAATTGTCCT(SEQ ID No.: 36) |
| pck-YZ-up | ACGCCATAAACAATCCAA (SEQ ID No.: 37) |
| pck-YZ-down | CGCATTTCACTGCTCCTT (SEQ ID No.: 38) | ackA-pta gene deletion and integration and modulation of lpdA*

| XZ-ackA-up | CGGGACAACGTTCAAAACAT (SEQ ID No.: 39) |
| XZ-pta-down | ATTGCCCATCTTCTTGTTGG (SEQ ID No.: 40) |
| XZ-ackA-2 | AACTACCGCAGTTCAGAACCA (SEQ ID No.: 41) |
| XZ-pta-2 | TCTGAACACCGGTAACACCA (SEQ ID No.: 42) |

Replacing aceBA promoter with Ppck*

| XZ-aceB-P-up | ATTCTGGCAGAGACGGAAGA (SEQ ID No.: 43) |
| XZ-aceB-P-down | TCGAAATCGGCCATAAAGAC (SEQ ID No.: 44) |
| XZ-aceB-P-2B | TTAATCCAGC GTTGGATTCA (SEQ ID No.: 45) |
| XZ-aceB-P-3 | ATGACTGAACAGGCAACAAC (SEQ ID No.: 46) |

Replacing dcuC promoter with Ppck*

| XZ-dcuC-P-up | TTTTCTGCGATGGGAATAGT (SEQ ID No.: 47) |
| XZ-dcuC-P-down | AAGCCTGGCTGGACGGTAAC (SEQ ID No.: 48) |
| XZ-dcuC-P-1 | ATGCTGACATTCATTGAGCTCCTTA (SEQ ID No.: 49) |
| XZ-dcuC-P-2 | AATTTTTCCTGTCTCCAGGCCCCAA (SEQ ID No.: 50) | mgsA gene deletion

| XZ-mgsA-up | CAGCTCATCAACCAGGTCAA (SEQ ID No.: 51) |
| XZ-mgsA-down | AAAAGCCGTCACGTTATTGG (SEQ ID No.: 52) |
| XZ-mgsA-1 | AGCGTTATCTCGCGGACCGT (SEQ ID No.: 53) |
| XZ-mgsA-2 | AAGTGCGAGTCGTCAGTTCC (SEQ ID No.: 54) | adhE gene deletion

| XZ-adhE-up | CAGCTCATCAACCAGGTCAA (SEQ ID No.: 55) |
| XZ-adhE-down | AAAAGCCGTCACGTTATTGG (SEQ ID No.: 56) |
| XZ-adhE-1 | AGCGTTATCTCGCGGACCGT (SEQ ID No.: 57) |
| XZ-adhE-2 | AAGTGCGAGTCGTCAGTTCC (SEQ ID No.: 58) | tdcDE gene deletion

| XZ-tdcDE-up | CAGCTCATCAACCAGGTCAA (SEQ ID No.: 59) |
| XZ-tdcDE-down | AAAAGCCGTCACGTTATTGG (SEQ ID No.: 60) |
| XZ-tdcDE-1 | AGCGTTATCTCGCGGACCGT (SEQ ID No.: 61) |
| XZ-tdcDE-2 | AAGTGCGAGTCGTCAGTTCC (SEQ ID No.: 62) | pck gene deletion

| XZ-pck-up | TCCGGGCAGTAGTATTTTGC (SEQ ID No.: 63) |
| XZ-pck-down | ATGGCTGGATCAAAGTCAGC (SEQ ID No.: 64) |
| XZ-pck-1 | CCTGGCGAAACTGTTTATCG (SEQ ID No.: 65) |
| XZ-pck-2 | TTGTTAACGCGCATTTCACT (SEQ ID No.: 66) | maeA gene deletion

| XZ-maeA-up | AGCGTTTCGTTACCACTG (SEQ ID No.: 67) |
| XZ-maeA-down | TACGGCGATGTTGTCCTT (SEQ ID No.: 68) |
| XZ-maeA-1 | ATTGACGATAATTTCTGGCA (SEQ ID No.: 69) |
| XZ-maeA-2 | ACGCTGTTTTTTTGTTTTTG (SEQ ID No.: 70) | maeB gene deletion

| XZ-maeB-up | TTAGCGTCATAATGCCAATT (SEQ ID No.: 71) |
| XZ-maeB-down | CGACCACCTGTTGTTCCTG (SEQ ID No.: 72) |

TABLE 2-continued

Primers used in the invention

| Name | Sequences |
|---|---|
| XZ-maeB-1 | ATCGGTGCGTCGTATCGT (SEQ ID No.: 73) |
| XZ-maeB-2 | AACCTGGATTTTCCCTGG (SEQ ID No.: 74) | ppc gene deletion

| Name | Sequences |
|---|---|
| XZ-ppc-up | GCGCATCTTATCCGACCTAC (SEQ ID No.: 75) |
| XZ-ppc-down | GCCTGGACTTCTGTGGAATG (SEQ ID No.: 76) |
| XZ-ppc-1 | GTCACTATTG CCGGGATTGC (SEQ ID No.: 77) |
| XZ-ppc-2 | CAATGCGGAA TATTGTTCGT (SEQ ID No.: 78) |

Modulation of tktA gene

| Name | Sequences |
|---|---|
| tktA-cat-sacB-up | AAATGCGCCGTTTGCAGGTGAATCGACGCTCAGTCTCAGTATAAGGAATGTGACGGAAGATCACTTCGCA (SEQ ID No.: 79) |
| tktA-cat-sacB-down | TCCATGCTCAGCGCACGAATAGCATTGGCAAGCTCTTTACGTGAGGACATTTATTTGTTAACTGTTAATTGTCCT (SEQ ID No.: 80) |
| tktA-P-up | AAATGCGCCGTTTGCAGGTGAATCGACGCTCAGTCTCAGTATAAGGAATTATCTCTGGCGGTGTTGAC (SEQ ID No.: 81) |
| tktA-RBS-down | TCCATGCTCAGCGCACGAATAGCATTGGCAAGCTCTTTACGTGAGGACATAGCTGTTTCCTGGTT (SEQ ID No.: 82) |
| tktA-YZ-up | TCAGGAAATCACGCCACA (SEQ ID No.: 83) |
| tktA-YZ-down | ATCCGTCATCATATCCATCA (SEQ ID No.: 84) |

Modulation of sthA gene

| Name | Sequences |
|---|---|
| sthA-cat-sacB-up | TTACCCGCGATAAAATGTTACCATTCTGTTGCTTTTATGTATAAGAACAGTGTGACGGAAGATCACTTCGCA (SEQ ID No.: 85) |
| sthA-cat-sacB-down | CCGGGGCCGGAACCTATTACTATGGCATCGTAATCGTAGGAATGTGGCATTTATTTGTTAACTGTTAATTGTCCT (SEQ ID No.: 86) |
| sthA-P-up | TTACCCGCGATAAAATGTTACCATTCTGTTGCTTTTATGTATAAGAACAGTTATCTCTGGCGGTGTTGAC (SEQ ID No.: 87) |
| sthA-RBS-down | CCGGGGCCGGAACCTATTACTATGGCATCGTAATCGTAGGAATGTGGCATAGCTGTTTCCTGGTT (SEQ ID No.: 88) |
| sthA-YZ-up | TTTTCAGCGGTTAGTGTTT (SEQ ID No.: 89) |
| sthA-YZ-down | AACTCAGGCTGGCGAAGC (SEQ ID No.: 90) |

Modulation of aceEF gene

| Name | Sequences |
|---|---|
| aceEF-cat-sacB-up | AGACTTCCGTCAGATCAAGAATAATGGTATGCGGCAGCGAATGCACCCGCTTTATGCATGTGTGACGGAAGATCACTTCGCA (SEQ ID No.: 91) |
| aceEF-cat-sacB-down | CCTGGAGCCAGTCGCGAGTTTCGATCGGATCCACGTCATTTGGGAAACGTTCTGACATTTATTTGTTAACTGTTAATTGTCCT (SEQ ID No.: 92) |
| aceEF-P-up | AGACTTCCGTCAGATCAAGAATAATGGTATGCGGCAGCGAATGCACCCGCTTTATGCATGTTATCTCTGGCGGTGTTGAC (SEQ ID No.: 93) |
| aceEF-RBS-down | CCTGGAGCCAGTCGCGAGTTTCGATCGGATCCACGTCATTTGGGAAACGTTCTGACATAGCTGTTTCCTG (SEQ ID No.: 94) |
| AP1-up | TTATCTCTGGCGGTGTTGAC (SEQ ID No.: 95) |
| aceEF-1 | ACGGAAGAAGTGGTTAAAGCACAC (SEQ ID No.: 96) |

Integration of lpdA* gene

| Name | Sequences |
|---|---|
| Kan-up-PacI | GCATTTAATTAAGTGTAGGCTGGAGCTGCT (SEQ ID No.: 97) |
| Kan-down-EcoRI | GCATGAATTCCAGAATCGAAATCTC (SEQ ID No.: 98) |
| Kan-F | CCGTGATATTGCTGAAGAG (SEQ ID No.: 99) |
| pTrc99A-R | CTGCGTTCTGATTTAATCTG (SEQ ID No.: 100) |
| lpdA-R-170 | AGCAGTGCTTTAGAAGGGATAC (SEQ ID No.: 101) |
| ackA-PRT-up | TCATCATGCGCTACGCTCTATGGCTCCCTGACGTTTTTTTAGCCACGTATCAATTATAGGTACTTCCGTGTAGGCTGGAGCTGCTTC (SEQ ID No.: 102) |
| pta-rrnB-down | GTTAAGCAAGATAATCAGAAAGGATTAATGCAGATTAAGAGAATAAAAAACCGGAAATAGTGAAAAAGGCCATCCGTCAGGAT (SEQ ID No.: 103) |

Modulation of lpdA*

| Name | Sequences |
|---|---|
| ackA-cat-sacB-up | TCATCATGCGCTACGCTCTATGGCTCCCTGACGTTTTTTTAGCCACGTATCAATTATAGGTACTTCCTGTGACGGAAGATCACTTCGCA (SEQ ID No.: 104) |
| lpdA-cat-sacB-down | CGGAAGGCAGCGGAGTAACCTGCGGGGCCTGCCCCAAGTACCACGACCTGAGTTTTGATTTCAGTACTCATCATTTATTTGTTAACTGTTAATTGTCCT (SEQ ID No.: 105) |
| ackA-P-up | TCATCATGCGCTACGCTCTATGGCTCCCTGACGTTTTTTTAGCCACGTATCAATTATAGGTACTTCCTTATCTCTGGCGGTGTTGAC (SEQ ID No.: 106) |

TABLE 2-continued

Primers used in the invention

| Name | Sequences |
|---|---|
| lpdA-RBS-down | CGGAAGGCAGCGGAGTAACCTGCGGGGCCTGCCCCAAGTACCACGA<br>CCTGAGTTTTGATTTCAGTACTCATCATAGCTGTTTCCTGGTT<br>(SEQ ID No.: 107) |

Modulation of zwf gene

| Name | Sequences |
|---|---|
| zwf-cat-sacB-up | ATCAGTTTTGCCGCACTTTGCGCGCTTTTCCCGTAATCGCACGGGTGG<br>ATAAGTGTGACGGAAGATCACTTCGCA (SEQ ID No.: 112) |
| zwf-cat-sacB-down | CCAGGGTATACTTGTAATTTTCTTACGGTGCACTGTACTGCTTTTACGA<br>GCTTGTTATTTGTTAACTGTTAATTGTCCT (SEQ ID No.: 113) |
| zwf-P-up | ATCAGTTTTGCCGCACTTTGCGCGCTTTTCCCGTAATCGCACGGGTGG<br>ATAAGTTATCTCTGGCGGTGTTGAC (SEQ ID No.: 114) |
| zwf-RBSL-down | GCGCCGAAAATGACCAGGTCACAGGCCTGGGCTGTTTGCGTTACCGC<br>CATNNNNNNYCTCCTGGTTTAAACGTACATG (SEQ ID No.: 115) |
| zwf-YZ-up | CATGGCAAAGTAGTTAATGG (SEQ ID No.: 116) |
| zwf-YZ-down | GACTCACGGGTAATGACGAT (SEQ ID No.: 117) |

Modulation of pgl gene

| Name | Sequences |
|---|---|
| pgl-cat-sacB-up | TTCAGCATTCACCGCCAAAAGCGACTAATTTTAGCTGTTACAGTCAGT<br>TGGCGTTGGCCGATTCATTA (SEQ ID No.: 118) |
| pgl-cat-sacB-down | ACGTGAATTTGCTGGCTCTCAGGGCTGGCGATATAAACTGTTTGCTTC<br>ATGGAGAAAATACCGCATCAGG (SEQ ID No.: 119) |
| pgl-P-up | TTCAGCATTCACCGCCAAAAGCGACTAATTTTAGCTGTTACAGTCAGT<br>TGTTATCTCTGGCGGTGTTGAC (SEQ ID No.: 120) |
| pgl-RBSL-down | ACGTGAATTTGCTGGCTCTCAGGGCTGGCGATATAAACTGTTTGCTTC<br>ATNNNNNNYCTCCTGGTTTAAACGTACATG (SEQ ID No.: 121) |
| pgl-YZ-up | GTGATGGCGACCTGTGACGA (SEQ ID No.: 122) |
| pgl-YZ-down | GGGCGAACACCAACATAGAG (SEQ ID No.: 123) |

Modulation of gnd gene

| Name | Sequences |
|---|---|
| gnd-cat-sacB-up | CTTACTAATTTAATGAATAGAACTCAATTGTATGTCCATTTGATTCAGTC<br>GCGTTGGCCGATTCATTA (SEQ ID No.: 124) |
| gnd-cat-sacB-down | TTGCGCCCCATCACTGCCATACCGACTACGCCGATCTGTTGCTTTGACA<br>TGGAGAAAATACCGCATCAGG (SEQ ID No.: 125) |
| gnd-P-up | CTTACTAATTTAATGAATAGAACTCAATTGTATGTCCATTTGATTCAGTC<br>TTATCTCTGGCGGTGTTGAC (SEQ ID No.: 126) |
| gnd-RBSL-down | TTGCGTCCCATCACTGCCATACCGACTACGCCGATCTGTTGCTTGGACA<br>TNNNNNNYCTCCTGGTTTAAACGTACATG (SEQ ID No.: 127) |
| gnd-YZ-up | GGTCCTTGCTATAAGAGTGA (SEQ ID No.: 128) |
| gnd-YZ-down | ACGGTTACGACGGATGGTGT (SEQ ID No.: 129) |

Modulation of tktA gene

| Name | Sequences |
|---|---|
| tktA-cat-sacB-up | AAATGCGCCGTTTGCAGGTGAATCGACGCTCAGTCTCAGTATAAGGAA<br>TGTGACGGAAGATCACTTCGCA (SEQ ID No.: 130) |
| tktA-cat-sacB-down | TCCATGCTCAGCGCACGAATAGCATTGGCAAGCTCTTTACGTGAGGAC<br>ATTTATTTGTTAACTGTTAATTGTCCT (SEQ ID No.: 131) |
| tktA-P-up | AAATGCGCCGTTTGCAGGTGAATCGACGCTCAGTCTCAGTATAAGGAA<br>TTATCTCTGGCGGTGTTGAC (SEQ ID No.: 132) |
| tktA-RBSL-down | TCCATGCTCAGCGCACGAATAGCATTGGCAAGCTCTTTACGTGAGGAC<br>ATNNNNNNYCTCCTGGTTTAAACGTACATG (SEQ ID No.: 133) |
| tktA-YZ-up | TCAGGAAATCACGCCACA (SEQ ID No.: 134) |
| tktA-YZ-down | ATCCGTCATCATATCCATCA (SEQ ID No.: 135) |

Modulation of talB gene

| Name | Sequences |
|---|---|
| talB-cat-sacB-up | AGTCTCGCCTGGCGATAACCGTCTTGTCGGCGGTTGCGCTGACGTTG<br>CGTCGTGTGTGACGGAAGATCACTTCGCA (SEQ ID No.: 136) |
| talB-cat-sacB-down | TCATGATAGTATTTCTCTTTAAACAGCTTGTTAGGGGGATGTAACCGGT<br>CTGCTTATTTGTTAACTGTTAATTGTCCT (SEQ ID No.: 137) |
| talB-P-up | AGTCTCGCCTGGCGATAACCGTCTTGTCGGCGGTTGCGCTGACGTTGC<br>GTCGTGTTATCTCTGGCGGTGTTGAC (SEQ ID No.: 138) |
| talB-RBSL-down | TCGGCCACTACGGTGGTGTACTGACGAAGGGAGGTCAATTTGTCCGT<br>CATNNNNNNYCTCCTGGTTTAAACGTACATG (SEQ ID No.: 139) |
| talB-YZ-up | CCGAAGAGCAGGTAAATCAT (SEQ ID No.: 140) |
| talB-YZ-down | TACCAGCATCGTTGTAGAGT (SEQ ID No.: 141) |

TABLE 3

Plasmids constructed in the invention

| Plasmid | Relevant characteristics |
|---|---|
| | Plasmid with cat-sacB cassette |
| pXZ-CS | cat gene of the plasmid pACYC184 and sacB gene from *Bacillus subtilis* were ligated and cloned into the plasmid pEASY-Blunt simple |
| | ldhA gene deletion |
| pXZ001 | ldhA gene was amplified by PCR by using *E. coli* ATCC 8739 genome as template with XZ-ldhA-up/XZ-ldhA-down and cloned into pEASY-Blunt vector |
| pXZ002C | cat-sacB cassette was amplified by PCR by using pXZ-CS as template with cat-sacB-up/cat-sacB-down and cloned the DNA fragment amplified by using the plasmid pXZ001 as template with primer set XZ-ldhA-1/XZ-ldhA-2 |
| pXZ003 | PCR fragment was amplified by using the plasmid pXZ001 as template with primer set XZ-ldhA-1/XZ-ldhA-2, phosphorylated and self-ligated |
| | pflB gene deletion |
| pXZ014 | pflB gene was amplified by PCR by using *E. coli* ATCC8739 genome as template with XZ-pflB-up/XZ-pflB-down and cloned into pEASY-Blunt vector |
| pXZ015C | cat-sacB cassette was amplified by PCR by using pXZ-CS as template with cat-sacB-up/cat-sacB-down and cloned into the DNA fragment amplified by using the plasmid pXZ014 as template with primer set XZ-pflB-1/XZ-pflB-2 |
| pXZ016 | DNA fragment was amplified by using the plasmid pXZ014 as template with primer set XZ-pflB-1/XZ-pflB-2, phosphorylated and self-ligated |
| | ptsI gene deletion |
| pXZ008 | ptsI gene was amplified by PCR by using *E. coli* ATCC 8739 genome as template with XZ-ptsI-up/XZ-ptsI-down and cloned into pEASY-Blunt vector |
| pXZ009C | cat-sacB cassette was amplified by PCR using pXZ-CS as template with cat-sacB-up/cat-sacB-down and cloned into the DNA fragment amplified by using the plasmid pXZ008 as template with primer set XZ-ptsI-1/XZ-ptsI-2 |
| pXZ010 | DNA fragment was amplified by using the plasmid pXZ008 as template with primer set XZ-ptsI-1/XZ-ptsI-2, phosphorylated and self-ligated |
| | Replacing galP promoter with Ppck* |
| pXZ602 | the regulatory part Ppck of pck gene was amplified by PCR using *E. coli* ATCC 8739 genome as template with P-pck*-up-SpeI/P-pck*-down-KpnI and cloned into pTrc99A vector |
| pXZ603 | DNA fragment was amplified by PCR using the plasmid pXZ602 as template with primer set pck*-F/pck*-R, phosphorylated and self-ligated |
| pXZ011 | galP gene was amplified by PCR using *E. coli* ATCC 8739 genome as template with XZ-galP-P-up/XZ-galP-P-down and cloned into pEASY-Blunt vector |
| pXZ012C | cat-sacB cassette was amplified by PCR using pXZ-CS as template with cat-sacB-up/cat-sacB-down and cloned into the DNA fragment amplified by using the plasmid pXZ011 as template with primer set XZ-galP-P-1/XZ-galP-P-2 |
| pXZ013 | the regulatory part Ppck* (using the plasmid pXZ603 as template with primer set P-pck*-up-SpeI/P-pck*-down-KpnI) was cloned into the DNA fragment amplified by using the plasmid pXZ011 as template with primer set XZ-galP-P-1/XZ-galP-P-2 |
| | ackA-pta gene deletion and integration and modulation of lpdA* gene |
| pXZ023 | ackA-pta gene was amplified by PCR using *E. coli* ATCC 8739 genome as template with XZ-ackA-up/XZ-pta-down and cloned into pEASY-Blunt vector |
| pXZ024C | cat-sacB cassette was amplified by PCR using pXZ-CS as template with cat-sacB-up/cat-sacB-down and cloned into the DNA fragment amplified by the plasmid pXZ023 as template with primer set XZ-pta-2/XZ-ackA-2 |
| pXZ025 | the DNA fragment was amplified by using the plasmid pXZ023 as template with primer set XZ-pta-2/XZ-ackA-2, phosphorylated and self-ligated |
| | Replacing aceBA promoter with Ppck* |
| pXZ026 | aceBA gene was amplified by PCR using *E. coli* ATCC 8739 genome as template with XZ-aceB-P-up/XZ-aceB-P-up and cloned into pEASY-Blunt vector |
| pXZ027C | cat-sacB cassette was amplified by PCR using pXZ-CS as template with cat-sacB-up/cat-sacB-down and cloned into the DNA fragment amplified by using the plasmid pXZ026 as template with primer set XZ-aceB-P-2B/XZ-aceB-P-3 |
| pXZ028 | Ppck* promoter (using the plasmid pXZ603 as template with primer set P-pck*-up-SpeI/P-pck*-down-KpnI) was cloned into the DNA fragment amplified by using the plasmid pXZ026 as template with primer set XZ-aceB-P-2B/XZ-aceB-P-3 |
| | Replacing dcuC promoter with Ppck* |
| pXZ065 | dcuC gene was amplified by PCR using *E. coli* ATCC 8739 genome as template with XZ-dcuC-P-up/XZ-dcuC-P-down and cloned into pEASY-Blunt vector |
| pXZ066C | cat-sacB cassette was amplified by PCR using pXZ-CS as template with cat-sacB-up/cat-sacB-down and cloned into the DNA fragment amplified by using the plasmid pXZ065 as template with primer set XZ-dcuC-P-1/XZ-dcuC-P-2 |

TABLE 3-continued

Plasmids constructed in the invention

| Plasmid | Relevant characteristics |
|---|---|
| pXZ067 | pck* promoter (using the plasmid pXZ603 as template with primer set P-pck*-up-SpeI/P-pck*-down-KpnI) was cloned into the DNA fragment amplified by using the plasmid pXZ065 as template with primer set XZ-dcuC-P-1/XZ-dcuC-P-2 | mgsA gene deletion

| Plasmid | Relevant characteristics |
|---|---|
| pXZ071 | mgsA gene was amplified by PCR using *E. coli* ATCC 8739 genome as template with XZ-mgsA-up/XZ-mgsA-down and cloned into pEASY-Blunt vector |
| pXZ072C | cat-sacB cassette was amplified by PCR using pXZ-CS as template with cat-sacB-up/cat-sacB-down and cloned into the DNA fragment amplified by using the plasmid pXZ071 as template with primer set XZ-mgsA-1/XZ-mgsA-2 |
| pXZ073 | the DNA fragment was amplified by using the plasmid pXZ071 as template with XZ-mgsA-1/XZ-mgsA-2, phosphorylated and self-ligated | adhE gene deletion

| Plasmid | Relevant characteristics |
|---|---|
| pXZ020 | adhE gene was amplified by PCR using *E. coli* ATCC 8739 genome as template with XZ-adhE-up/XZ-adhE-down and cloned into pEASY-Blunt vector |
| pXZ021C | cat-sacB cassette was amplified by PCR using pXZ-CS as template with cat-sacB-up/cat-sacB-down and cloned into the DNA fragment amplified by using the plasmid pXZ020 as template with primer set XZ-adhE-1/XZ-adhE-2 |
| pXZ022 | the DNA fragment was amplified by using the plasmid pXZ020 as template with primer set XZ-adhE-1/XZ-adhE-2, phosphorylated and self-ligated | tdcDE gene cluster deletion

| Plasmid | Relevant characteristics |
|---|---|
| pXZ641 | tdcDE gene cluster was amplified by PCR using *E. coli* ATCC 8739 genome as template with XZ-tdcDE-up/XZ-tdcDE-down and cloned into pEASY-Blunt vector |
| pXZ642C | cat-sacB cassette was amplified by PCR using pXZ-CS as template with cat-sacB-up/cat-sacB-down and cloned into the DNA fragment amplified by using the plasmid pXZ641 as template with primer set XZ-tdcDE-1/XZ-tdcDE-2 |
| pXZ643 | the DNA fragment was amplified by using the plasmid pXZ641 as template with primer set XZ-tdcDE-1/XZ-tdcDE-2, phosphorylated and self-ligated | pck gene deletion

| Plasmid | Relevant characteristics |
|---|---|
| pXZ701 | pck gene was amplified by PCR using *E. coli* ATCC 8739 genome as template with XZ-pck-up/XZ-pck-down and cloned into pEASY-Blunt vector |
| pXZ702C | cat-sacB cassette was amplified by PCR using pXZ-CS as template with cat-sacB-up/cat-sacB-down and cloned into the DNA fragment amplified by using the plasmid pXZ701 as template with primer set XZ-pck-1/XZ-pck-2 |
| pXZ703 | the DNA fragment was amplified by using the plasmid pXZ701 as template with primer set XZ-pck-1/XZ-pck-2, phosphorylated and self-ligated | maeB gene deletion

| Plasmid | Relevant characteristics |
|---|---|
| pXZ704 | maeB gene was amplified by PCR using *E. coli* ATCC 8739 genome as template with XZ-maeB-up/XZ-maeB-down and cloned into pEASY-Blunt vector |
| pXZ705C | cat-sacB cassette was amplified by PCR using pXZ-CS as template with cat-sacB-up/cat-sacB-down and cloned into the DNA fragment amplified by using the plasmid pXZ704 as template with primer set XZ-maeB-1/XZ-maeB-2 |
| pXZ706 | the DNA fragment was amplified by using the plasmid pXZ704 as template with primer set XZ-maeB-1/XZ-maeB-2, phosphorylated and self-ligated | ppc gene deletion

| Plasmid | Relevant characteristics |
|---|---|
| pXZ707 | ppc gene was amplified by PCR using *E. coli* ATCC 8739 genome as template with XZ-ppc-up/XZ-ppc-down and cloned into pEASY-Blunt vector |
| pXZ708C | cat-sacB cassette was amplified by PCR using pXZ-CS as template with cat-sacB-up/cat-sacB-down and cloned into the DNA fragment amplified by using the plasmid pXZ707 as template with primer set XZ-ppc-1/XZ-ppc-2 |
| pXZ709 | the DNA fragment was amplified by using the plasmid pXZ707 as template with primer set XZ-ppc-1/XZ-ppc-2, phosphorylated and self-ligated | maeA gene deletion

| Plasmid | Relevant characteristics |
|---|---|
| pXZ710 | maeA gene was amplified by PCR using *E. coli* ATCC 8739 genome as template with XZ-maeA-up/XZ-maeA-down) and cloned into pEASY-Blunt vector |

TABLE 3-continued

Plasmids constructed in the invention

| Plasmid | Relevant characteristics |
|---|---|
| pXZ711C | cat-sacB cassette was amplified by PCR using pXZ-CS as template with cat-sacB-up/cat-sacB-down and cloned into the DNA fragment amplified by using the plasmid pXZ710 as template with primer set XZ-maeA-1/XZ-maeA-2 |
| pXZ712 | the DNA fragment was amplified by using the plasmid pXZ710 as template with primer set XZ-maeA-1/XZ-maeA-2, phosphorylated and self-ligated |
| | Integration of lpdA* |
| pTrc99A-M-Kan | FRT-Kan fragment was amplified from pKD4 (Kan-up-PacI/Kan-down-EcoRI) and cloned into pTrc99A-M vector |
| pXZ174 | lpdA* was amplified by PCR using HX-024 genome as template with 8739-lpdA-up-SacI/8739-lpdA-down-PstI and cloned into pTrc99A-M vector |
| pXZ177 | lpdA* (T82I P275S and A358V) fragment was obtained by enzymatically cleaving the plasmid pXZ174 and ligated into pTrc99A-M-Kan |

Example 2: Production of Succinate by Recombinant Strains Suc-T110, NZ-035, NZ-036 and NZ-037

The seed medium consists of ($H_2O$ as solvent):

Major elements: glucose 20 g/L, $KH_2PO_4$ 3.5 g/L, $K_2HPO_4$ 6.55 g/L, $(NH_4)_2HPO_4$ 3.5 g/L, $MgSO_4.7H_2O$ 0.12 g/L and betaine-KCl 0.15 g/L, and Trace elements: $FeCl_3.6H_2O$ 1.5 µg/L, $CoCl_2.6H_2O$ 0.1 µg/L, $CuCl_2.2H_2O$ 0.1 µg/L, $ZnCl_2$ 0.1 µg/L, $Na_2MoO_4.2H_2O$ 0.1 µg/L, $MnCl_2.4H_2O$ 0.2 µg/L, $H_3BO_3$ 0.05 µg/L.

Fermentation medium was the same as the seed medium, except for containing 50 g/L glucose and 100 mM $KHCO_3$ unless stated otherwise.

The anaerobic fermentation of the strains Suc-T110, NZ-035, NZ-036 and NZ-037 was carried out under the conditions as following:

(1) Seed culture: 100 ml of seed medium in a 250 ml flask was sterilized at 115° C. for 15 min. Suc-T110, NZ-035, NZ-036 and NZ-037 were grown by transferring pre-inocula (an inoculum of 1% (v/v)) into the seed medium, at 37° C. with shaking at 100 rpm for 12 h to obtain the seed culture.

(2) Fermentation: the seed cultures were diluted into a 500-ml fermentation vessel containing 250 ml of fermentation medium with a final concentration of $OD_{550}$=0.1, and grown at 37° C., 150 rpm for 4 days to obtain the fermentation broth. The neutralizer was 2.4 M potassium carbonate and 1.2 M potassium hydroxide. The fermentation broth comprises all the substance in the vessel. No air was sparged in whole processes for fermentation.

Analysis: the components in the fermentation broth were assayed on day 4 by using the High-Performance Liquid Chromatograph (Agilent-1200). The concentrations of glucose and organic acids in the fermentation broth were measured by the column of Aminex HPX-87H (Bio-rad).

The results were shown in Table 4. After 96 h fermentation, the strain Suc-T110 produced succinate of 280 mM, with a yield of 1.12 mol/mol; after 96 h fermentation, the strain NZ-035 produced succinate of 286 mM, with a yield of 1.16 mol/mol; after 96 h fermentation, the strain NZ-036 produced succinate of 298 mM, with a yield of 1.19 mol/mol; and after 96 h fermentation, the strain NZ-037 produced succinate of 357 mM, with a yield of 1.28 mol/mol.

TABLE 4

Fermentative production of succinate by recombinant E. coli Suc-T110, NZ035, NZ036 and NZ037

| Strain[a] | Genetic modification | Cell mass (g/L) | Succinate yield (g/g) | Succinate yield (mol/mol) | Fermentation product (mM) succinate | acetate |
|---|---|---|---|---|---|---|
| Suc-T110 | Suc-T108, Ppck*-pck | 1.53 | 0.73 ± 0.02 | 1.12 ± 0.03 | 280 ± 10 | 96 ± 10 |
| NZ-035 | Suc-T110, ΔackA-pta | 1.51 | 0.76 ± 0.02 | 1.16 ± 0.03 | 286 ± 7 | 44 ± 6 |
| NZ-036 | NZ-035, Ppck*-aceBA | 1.48 | 0.78 ± 0.02 | 1.19 ± 0.03 | 298 ± 6 | 27 ± 4 |
| NZ-037 | NZ-036, Ppck*-dcuC | 1.50 | 0.84 ± 0.02 | 1.28 ± 0.03 | 357 ± 7 | 25 ± 3 |

[a]500-ml fermentation vessel, 250 ml fermentation medium. The fermentation medium contains 100 mM $KHCO_3$. The neutralizer is 2.4M $K_2CO_3$ and 1.2M KOH.

Example 3: Production of Succinate by Fermentation of Recombinant E. coli NZ-037 Using Sodium Salts The components of the seed medium consisted of ($H_2O$ as solvent):

Major elements: glucose 20 g/L, $NH_4H_2PO_4$ 0.87 g/L, $(NH_4)_2HPO_4$ 2.63 g/L, $MgSO_4.7H_2O$ 0.18 g/L, Betaine-KCl 0.15 g/L, and Trace elements: $FeCl_3.6H_2O$ 2.4 µg/L, $CoCl_2.6H_2O$ 0.3 µg/L, $CuCl_2.2H_2O$ 0.15 µg/L, $ZnCl_2$ 0.3 µg/L, $Na_2MoO_4.2H_2O$ 0.3 µg/L, $MnCl_2.4H_2O$ 0.5 µg/L, $H_3BO_3$ 0.072 µg/L.

The fermentation medium is the same as the seed medium, except for containing 100 g/L glucose and 35 mM sodium bicarbonate. The neutralizer was 2.4 M sodium carbonate and 1.2 M sodium hydroxide.

Seed cultures, fermentations and analysis were the same as described in Example 2.

Results: after 96 h fermentation, the titer of succinate was 226 mM, with a yield of 1.27 mol/mol.

Example 4: Construction of Recombinant E. coli HX021

In order to improve cell growth and succinate productivity, metabolic evolution of NZ-037 was carried out.
The fermentation medium for metabolic evolution consisted of ($H_2O$ as solvent):
Major elements: glucose 100-200 g/L, $NH_4H_2PO_4$ 0.87 g/L, $(NH_4)_2HPO_4$ 2.63 g/L, $MgSO_4 \cdot 7H_2O$ 0.18 g/L, Betaine-KCl 0.15 g/L, 35 mM $NaHCO_3$, and
Trace elements: $FeCl_3 \cdot 6H_2O$ 2.4 μg/L, $CoCl_2 \cdot 6H_2O$ 0.3 μg/L, $CuCl_2 \cdot 2H_2O$ 0.15 μg/L, $ZnCl_2$ 0.3 μg/L, $Na_2MoO_4 \cdot 2H_2O$ 0.3 μg/L, $MnCl_2 \cdot 4H_2O$ 0.5 μg/L, $H_3BO_3$ 0.07214/L.

The metabolic evolution was carried out in a 500-ml fermentation vessel containing 250 ml of the fermentation medium. 2.4 M sodium carbonate and 1.2 M sodium hydroxide were used as neutralizer.

For 1-80 generations, the fermentation medium contained 100 g/L glucose (10%). Every 48 hours, the fermentation broth was transferred to a new fermentation vessel, with an initial OD550 of 0.05.

For 81-780 generations, the fermentation medium contained 100 g/L glucose. Every 24 hours, the fermentation broth was transferred to a new fermentation vessel, with an initial OD550 of 0.05.

For 781-1080 generations, the fermentation medium contained 120 g/L glucose (12%). Every 24 hours, the fermentation broth was transferred to a new fermentation vessel, with an initial OD550 of 0.05.

Figure 2:
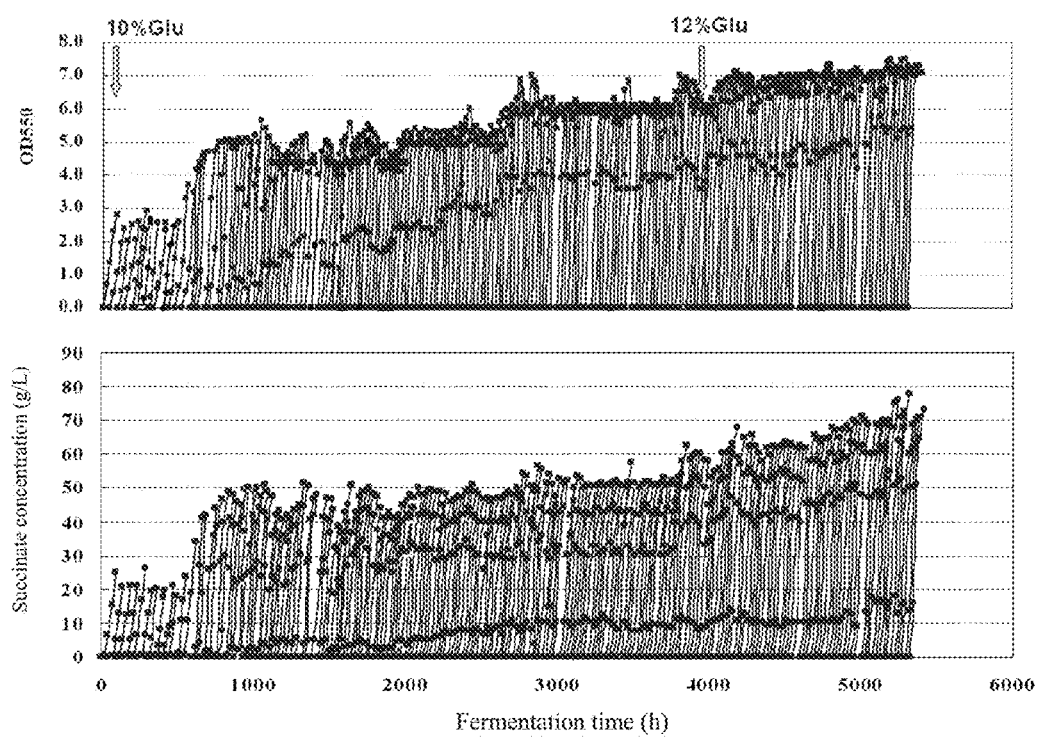
FIG. 2: Metabolic evolution of strain NZ-037 for 1080 generations to obtain strain HX021.

Metabolic evolution for 1080 generations, the resulting strain HX021 was obtained (FIG. 2).

Example 5: Construction of Recombinant E. coli HX023

The mgsA gene (GenBank No: ACA78263.1) was deleted from the recombinant E. coli HX021 using the method as described for deleting ldhA in section (1) of Example 1. The resulting strain was designated as HX023. The plasmids constructed are listed in Table 3, and the primers used are listed in Table 2. The primers were named in same manner as those used for deleting ldhA gene, while only ldhA was replaced by mgsA.

Example 6: Construction of Recombinant E. coli HX024

In order to improve cell growth and succinate productivity, metabolic evolution of HX023 was carried out.

Fermentation and metabolic evolution were the same as described in Example 4.

For 1-360 generations, the fermentation medium contained 120 g/L glucose (12%). Every 24 hours, the fermentation broth was transferred to a new fermentation vessel, with an initial OD550 of 0.05.

Figure 3:
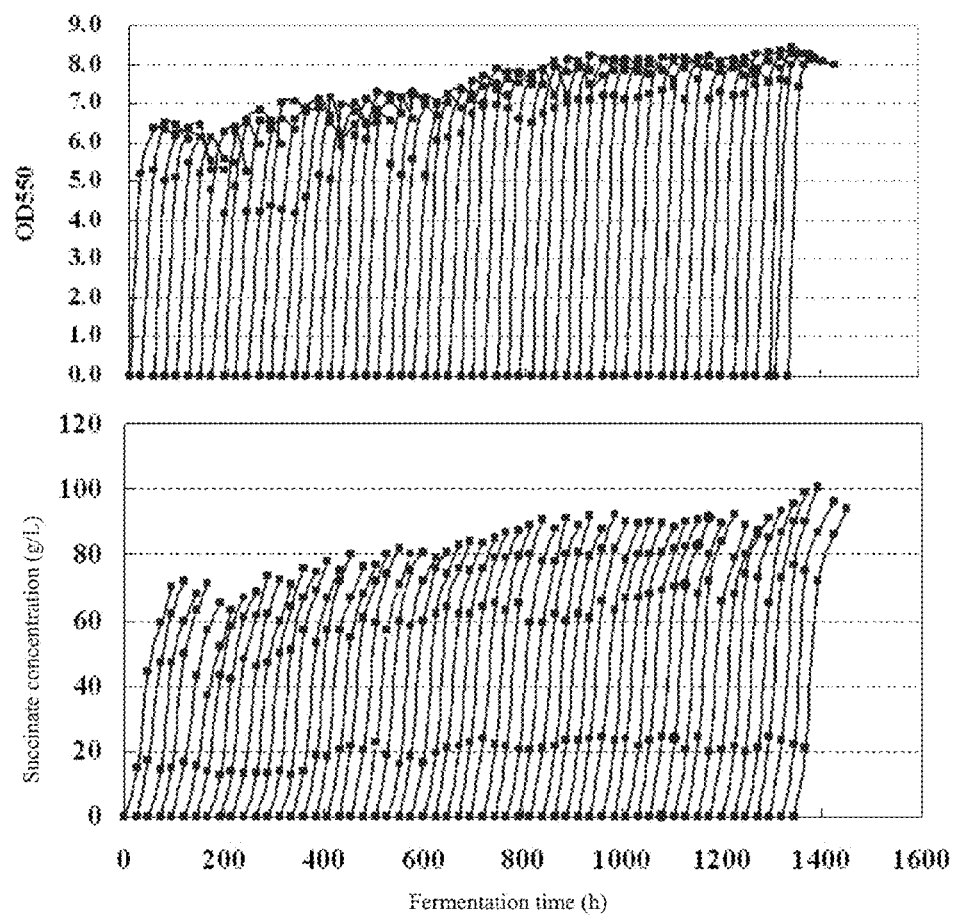
FIG. 3: Metabolic evolution of strain HX023 for 360 generations to obtain strain HX024.

Metabolic evolution for 360 generations, the resulting strain HX024 was obtained (FIG. 3).

Example 7: The Effects of Bicarbonate Ion Supply of Various Concentrations on the Fermentation of Recombinant E. coli HX024

The various concentrations of bicarbonate ion were supplied in the fermentation of the recombinant E. coli HX024.

The seed medium is the same as that described in Example 3.

A 500-ml fermentation vessel containing 250 ml fermentation medium was used. The fermentation medium was the same as the seed medium, supplemented with 120 g/L glucose and 35 mM sodium bicarbonate. The neutralizers used had five different ratios of 6 M sodium hydroxide and 3 M sodium carbonate, i.e. 1:4, 1:2, 1:1, 3:2 and 2:1.

For strain HX024, anaerobic fermentation in 500-ml fermentation vessel, was carried out as following:

(1) Seed culture: 100 ml of seed medium in a 250 ml flask was sterilized at 115° C. for 15 min. HX024 was grown by transferring pre-inocula (an inoculum of 1% (v/v)) into the seed medium, at 37° C. with shaking at 100 rpm for 12 h to obtain the seed culture.

(2) Fermentation: 250 ml fermentation medium in a 500-ml fermentation vessel was sterilized at 115° C. for 25 min. The seed culture was diluted into the fermentation medium with a final concentration of $OD_{550}=0.1$, and grown at 37° C., 150 rpm under anaerobic condition for 4 days to obtain the fermentation broth. The fermentation broth comprises all the substance in the vessel. No air was sparged in whole processes for fermentation.

The results of fermentation were shown in Table 5. When the molar ratio of $CO_2$ in the basic solution was less than 33.3%, succinate yield was decreased significantly among the different ratios of sodium hydroxide and sodium carbonate. However, no significantly difference was seen when the molar ratio of $CO_2$ in the basic solution was higher than 33.3%.

TABLE 5

The effects of different bicarbonate ion supply on the fermentation of the recombinant E. coli HX024

| $NaOH:Na_2CO_3$ [a] | $CO_2$ (% mol) [b] | Base consumption (ml) | $CO_2$ consumption (mM) | Succinate (mM) | Succinate yield (mol/mol) |
|---|---|---|---|---|---|
| 1:4 | 67% | 88 ± 3 | 880 ± 29 | 813 ± 28 | 1.36 ± 0.04 |
| 1:2 | 50% | 78 ± 4 | 659 ± 32 | 785 ± 40 | 1.30 ± 0.01 |
| 1:1 | 33.3% | 72 ± 2 | 467 ± 12 | 798 ± 21 | 1.33 ± 0.02 |
| 3:2 | 25% | 67 ± 1 | 357 ± 5 | 781 ± 12 | 1.15 ± 0.03 |
| 2:1 | 20% | 63 ± 2 | 287 ± 8 | 739 ± 23 | 1.08 ± 0.03 |

[a] 500-ml fermentation vessel, 250 ml fermentation medium. The fermentation medium contains 35 mM $NaHCO_3$. The pH was maintained at 7.0 by addition of a base consisting of NaOH (6M) and $Na_2CO_3$ (3M) of various ratios.
[b] $CO_2$ (% mol) represents the molar ratio of $CO_2$ in the base.

Example 8: Fermentation of Recombinant E. coli HX021, HX021 and HX024 in a 500-ml Fermentation Vessel The seed medium is the same as that described in Example 3.

A 500-ml fermentation vessel containing 250 ml of the fermentation medium was used. The fermentation medium was the same as the seed medium, supplemented with 120 g/L glucose and 35 mM sodium bicarbonate. The neutralizer used was 1.5 M sodium carbonate and 3 M sodium hydroxide.

Results: after 96 h fermentation, the titer of succinate produced by strain HX021 was 618 mM, with a yield of 1.24 mol/mol; after 96 h fermentation, the titer of succinate produced by strain HX023 was 594 mM, with a yield of 1.25 mol/mol; and after 96 h fermentation, the titer of succinate produced by strain HX024 was 798 mM, with a yield of 1.33 mol/mol. (Table 6)

TABLE 6

Fermentative succinate production by recombinant E. coli HX021, HX023 and HX024

| Strain | medium[a] | Cell mass (g/L) | Succinate yield (g/g) | Succinate yield (mol/mol) | Fermentation product (mM)[b] | |
|---|---|---|---|---|---|---|
| | | | | | succinate | acetate |
| HX021 | 12%, AM1 | 2.4 | 0.81 ± 0.01 | 1.24 ± 0.02 | 618 ± 3 | 18 ± 3 |
| HX023 | 12%, AM1 | 2.1 | 0.82 ± 0.01 | 1.25 ± 0.01 | 594 ± 33 | 16 ± 1 |
| HX024 | 12%, AM1 | 2.72 | 0.87 ± 0.01 | 1.33 ± 0.02 | 798 ± 21 | 23 ± 2 |

[a]500-ml fermentation vessel, 250 ml fermentation medium. The fermentation medium contains 35 mM NaHCO$_3$. The used neutralizer was 1.5M Na$_2$CO$_3$ and 3M NaOH.

Example 9: Fermentation of Recombinant Strain HX024 in 5 L Fermentation Vessel The seed medium, the fermentation medium and the analysis were the same as described in Example 8.

The anaerobic fermentation of HX024 in a 5 L fermentation vessel (Shanghai BaoXing, BIOTECH-5BG) was carried out as follows:

(1) Seed culture: 150 ml of seed medium in a 500 ml flask was sterilized at 115° C. for 15 min. HX024 was grown by transferring pre-inocula (an inoculum of 1% (v/v)) into the seed medium, at 37° C. with shaking at 100 rpm for 12 h to obtain the seed culture.

(2) Fermentation: 3 L of fermentation medium in a 5-L fermentation vessel was sterilized at 115° C. for 25 min. The seed culture was diluted into the fermentation medium with a final concentration of OD$_{550}$=0.2, and grown at 37° C., 200 rpm under anaerobic condition for 4 days to obtain the fermentation broth. The fermentation broth comprises all the substance in the vessel. No air was sparged in whole processes for fermentation.

Figure 4:
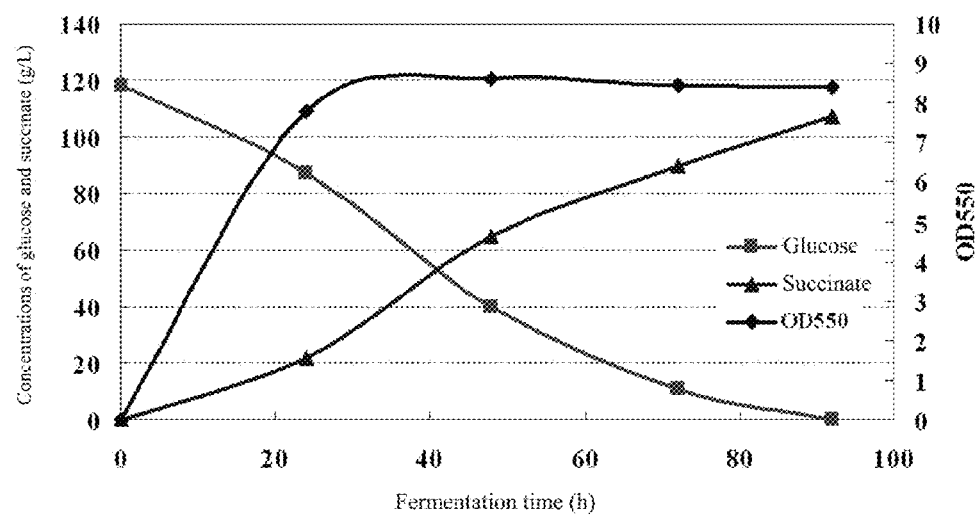
FIG. 4: Fermentaion of strain HX024 to produce succinate in a 5 L fermentation vessel.

Results: after 96 h fermentation, the titer of succinate was 915 mM (108 g/L) with a yield of 1.37 mol/mol (0.9 g/g). (FIG. 4)

Example 10: Construction and Fermentation of Recombinant E. coli HX041-HX044

(1) Construction of the Recombinant E. coli HX041-HX044

From the recombinant E. coli HX024, the pck gene (GenBank No: ACA75988.1), maeA gene (GenBank No: ACA77817.1), maeB (GenBank No: ACA76880.1), and ppc gene (GenBank No:ACA79659.1) were deleted individually, resulting in strains HX041-HX044 (Table 1), respectively, using the method described in the section (1-2) of Example 1. The plasmids constructed are listed in Table 3, and the primers used are listed in Table 2. The primers were named in same manner as those used for deleting ldhA gene, while only ldhA was replaced by pck, maeA, maeB or ppc, respectively.

(2) Fermentation of Recombinant E. coli HX041-HX044

The fermentative succinate production by the recombinant E. coli HX041-HX044 was carried out using the same method as described in Example 8.

The results of fermentation were shown in Table 7. The strain HX041, with pck gene deleted, still produced a large amount of succinate, indicating that E. coli strain could produce succinate without PCK involved PEP carboxylation. After deleting maeB gene from HX-024, the succinate titer of the strains were decreased by 29%, indicating that MaeB plays a role in the strain HX024 and some of carbon metabolic flux went through MaeB to contribute succinate production. After deleting maeA gene in HX024, the succinate titer was decreased by 49%, indicating that MaeA plays a role in the strain HX024 and some of carbon metabolic flux went through MaeA to contribute succinate production In addition, after deleting ppc gene from HX024, the seed culture of the strain cannot be grown in mineral salts medium. After seed culture was grown in a LB medium and then fermentated in mineral salts medium, the succinate titer was decreased by 70%, indicating that PPC could play an important role on succinate production for its excellent enzyme catalytic kinetic characteristics.

TABLE 7

Fermentation of recombinant E. coli HX041-HX044 to produce succinate

| Strain[a] | Genetic modification | Cell mass (g/L) | Succinate yield (g/g) | Succinate yield (mol/mol) | Fermentation product (mM) | |
|---|---|---|---|---|---|---|
| | | | | | succinate | acetate |
| HX024 | | 2.72 | 0.87 ± 0.01 | 1.33 ± 0.02 | 798 ± 21 | 23 ± 2 |
| HX041 | HX024, Δpck | 2.00 | 0.86 ± 0.02 | 1.31 ± 0.03 | 492 ± 18 | 22 ± 2 |
| HX042 | HX024, ΔmaeA | 1.92 | 0.86 ± 0.01 | 1.31 ± 0.02 | 405 ± 44 | 25 ± 3 |
| HX043 | HX024, ΔmaeB | 2.18 | 0.87 ± 0.01 | 1.33 ± 0.01 | 566 ± 31 | 20 ± 1 |
| HX044 | HX024, Δppc | — | — | — | — | — |
| HX044[b] | HX024, Δppc | 1.49 | 0.79 ± 0.03 | 1.21 ± 0.04 | 241 ± 19 | 10 ± 1 |

[a]500-ml fermentation vessel, 250 ml fermentation medium. The fermentation medium contains 35 mM NaHCO$_3$. The used neutralizer was 1.5M Na$_2$CO$_3$ and 3M NaOH.
[b]The seed culture of HX044 was prepared by LB medium, and then fermentated in mineral salts medium. The mineral salts medium plus 2% glucose was used as the seed medium for the other strains.

Example 11: Construction and Fermentation of Recombinant E. coli HX027 and HX028

(1) Construction of Recombinant E. coli HX027

The adhE gene (Genbank No: ACA78022.1) from the strain HX024 was deleted to obtain recombinant strain HX026, and then the tdcDE gene cluster (tdcD gene: GenBank No:ACA76259.1; tdcE gene GenBank No: ACA76260.1) was further deleted to obtain recombinant strain HX027 (Table 1), using the method as described in the section (1) of Example 1. The plasmids constructed are listed in Table 3, and the primers used are listed in Table 2. The primers were named in same manner as those used for deleting ldhA gene, while only ldhA was replaced by adhE or tdcDE, respectively.

(2) Construction of Recombinant Strain HX028

In order to improve cell growth and succinate productivity, metabolic evolution of HX027 was carried out.

The fermentation medium and metabolic evolution were the same as described in Example 4.

Figure 5:
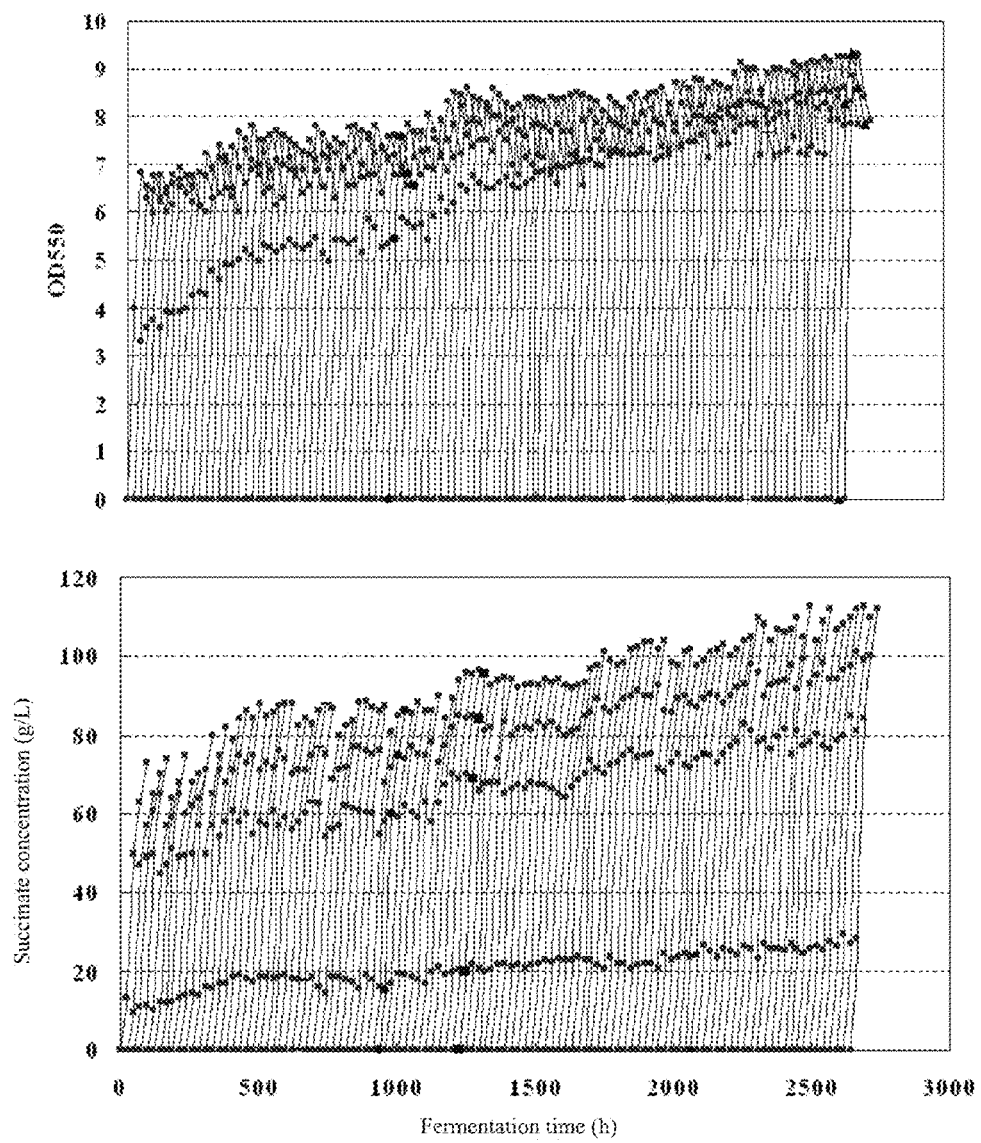
FIG. 5: Metabolic evolution of strain HX027 for 650 generations to obtain strain HX028.

For 1-650 generations, the fermentation medium contained 120 g/L glucose (12%). Every 24 hours, the fermentation broth was transferred to a new fermentation vessel, with an initial OD550 of 0.05 (FIG. 5).

After evolution of 650 generations, the strain HX028 (FIG. 5) was obtained.

(3) Fermentation of the Recombinant Strain HX028

Following the method of Example 9, the fermentation of the recombinant E. coli HX028 was carried out in a 5 L fermentation vessel.

Figure 6:
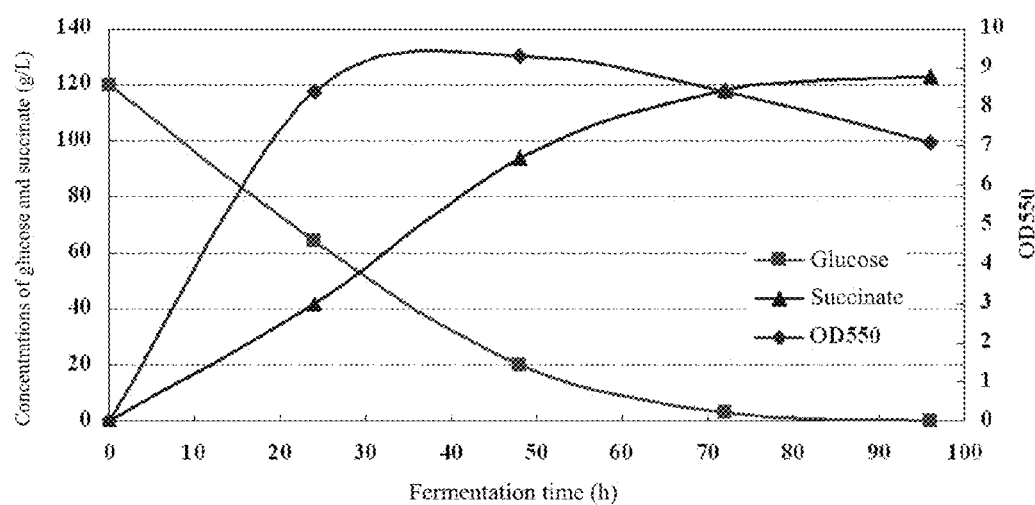
FIG. 6: Fermentaion of strain HX028 to produce succinate in a 5 L fermentation vessel.

The results of fermentation were shown in FIG. 6. After 96 h fermentation, the succinate titer was 1042 mM (equivalent to 123 g/L) with a yield of 1.02 g/g (equivalent to 1.56 mol/mol).

Example 12: Transcriptome Analysis of the Recombinant E. coli HX024

The transcriptome analysis of the recombinant E. coli HX024 was carried out as follows:

(1) Fermentation

The seed culture and fermentation of the strain HX024 were the same as described in Example 8. Three parallel anaerobic fermentations were performed.

The seed culture and fermentation of the wild-type ATCC 8739 were the same as described in Example 5, except that the concentration of glucose was 50 g/L.

(2) RNA Extraction

Three parallel fermentation samples of HX024 cells were collected at OD550=3.9, mixed and extracted for RNA.

Three parallel fermentation samples of the wild type ATCC 8739 cells were collected at OD550=2.5, mixed and extracted for RNA.

RNA was extracted by using RNeasy Mini kit (Qiagen). DNase treatment was performed by The RNase-Free DNase Set kit (Qiagen).

(3) Transcriptome Sequencing

Transcriptome sequencing was performed by BGI (Beijing, China). 1 Gb clean data were generated from each sample. The reference sequence was the genome sequence of ATCC 8739 (http://www.ncbi.nlm.nih.gov/nuccore/NC_010468.1).

Figure 7:
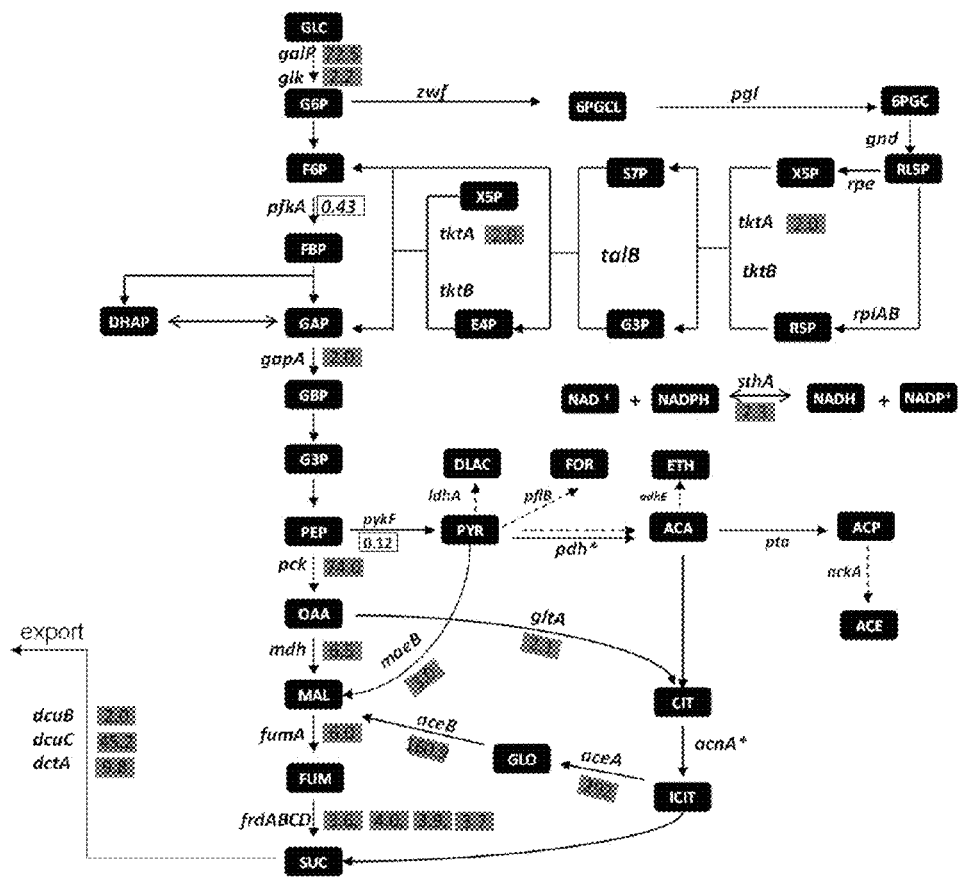
FIG. 7: Results of comparative transcriptome analysis of HX024. The shaded and boxed numbers are the ratios of the expression levels of genes in HX024 vs. wild type *E. coli* ATCC 8739. Abbreviations: GLC: glucose; G6P: glucose-6-phosphate; F6P: fructose-6-phosphate; FBP: fructose-1,6-biphosphate; GAP: glyceraldehyde-3-phosphate; DHAP: dihydroxyacetone phosphate; GBP: 1,3-bisphosphoglycerate; G3P: 3-phosphoglycerate; PEP: phosphoenolpyruvate; OAA: oxaloacetate; MAL: malate; FUM: fumarate; SUC: succinate; 6PGCL: gluconolactone-6-phosphate; 6PGC: 6-phosphogluconate; RL5P: ribulose-5-phosphate; X5P: xylose-5-phosphate; RSP: ribose-5-phosphate; S7P: sedoheptulose-7-phosphate; E4P: erythrose-4-phosphate; PYR: pyruvate; ACA: acetyl-CoA; ACP: acetylphosphate; ACE: acetate; CIT: citrate; ICIT: isocitrate; GLO: glyoxalate; DLAC: D-lactate; FOR: formate; ETH: ethanol; $NAD^+$: oxidized nicotinamide adenine dinucleotide; NADPH: reduced nicotinamide adenine dinucleotide phosphate; NADH: reduced nicotinamide adenine dinucleotide; $NADP^+$: oxidized nicotinamide adenine dinucleotide phosphate. galP: galactose permease gene; glk: glucokinase kinase gene; gapA: glycerol-3-phosphate dehydrogenase gene; pfkA: fructose-6-phosphate kinase gene; pck: phosphoenolpyruvate carboxylase gene; mdh: malate dehydrogenase gene; fumA: fumarate hydratase enzyme I gene; frdABCD: fumarate reductase gene; zwf: 6-phosphoglucose dehydrogenase gene; pgl: 6-phosogluconolactonase gene; gild: 6-phosphogluconate dehydrogenase gene; rpe: ribulose-5-phosphate epimerase gene; rpiAB: ribose-5-phosphate epimerase gene; tktA: transketolase gene; tktB: transketolase gene; talB: transaldolase gene; pykF: pyruvate kinase gene; pdh: pyruvate dehydrogenase gene; pta: phosphate acetyltransferase gene; ackA: acetokinase gene; gltA: citrate synthetase gene; acn: aconitase gene; aceB: malate synthetase gene; aceA: isocitrate lyase gene; sthA: pyrimidine nucleotide transhydrogenase gene; maeB: NADPH dependent malic enzyme gene; dcuB: anaerobic C4 dicarboxylate transporter gene; dcuC: C4 dicarboxylate transporter gene; dctA: aerobic C4 dicarboxylate transporter gene.

Expression levels of genes related with succinate production in HX024 were shown in Table 8 and FIG. 7.

TABLE 8

Transcriptome analysis of the recombinant E. coli HX024

| Gene | Protein | Relative expression level [a] |
|---|---|---|
| Module 1: glucose utilization | | |
| galP | galactose permease | 72.5 |
| glk | glucokinase | 2.2 |
| Module 2: carboxylation | | |
| pck | phosphoenolpyruvate carboxykinase | 74.0 |
| maeB | NADPH-dependent malic enzyme | 3.0 |
| Module 3: Reductive TCA | | |
| mdh | malate dehydrogenase | 6.5 |
| fumA | fumarate hydratase, class I | 6.0 |
| frdA | fumarate reductase flavoprotein subunit | 3.6 |
| frdB | fumarate reductase iron-sulfur protein | 4.0 |
| frdC | fumarate reductase subunit C | 3.9 |
| frdD | fumarate reductase subunit D | 3.7 |
| Module 4: TCA | | |
| gltA | Citrate synthase | 2.1 |
| Module 5: glyoxylate bypass | | |
| aceB | malate synthase | 160.9 |
| aceA | isocitrate lyase | 292.0 |
| Module 6: pentose phoasphate pathway | | |
| tktA | transketolase | 2.0 |
| Module 7: glycolysis | | |
| pfkA | 6-phosphofructokinase | 0.43 |
| pykF | pyruvate kinase | 0.12 |
| gapA | glyceraldehyde 3-phosphate dehydrogenase | 2.0 |
| Module 8: transhydrogenase | | |
| sthA | pyridine nucleotide transhydrogenase | 2.3 |
| Module 9: succinate export | | |
| dcuB | anaerobic C$_4$-dicarboxylate transporter DcuB | 2.0 |
| dcuC | C$_4$-dicarboxylate transporter DcuC | 45.3 |
| dctA | aerobic C$_4$-dicarboxylate transport protein | 9.8 |

[a] Relative expression level represented gene expression strength of strain HX024 compared to wild type E. coli ATCC 8739.

According transcriptome analysis, expression levels of genes related with succinate production had increased significantly.

(1) The expression level of tktA gene from Pentose phosphate pathway was increased, and that of pfkA gene from Glycolysis pathway (EMP) was decreased, indicating that more carbon flux went through PPP pathway to generate more reducing equivalent in the form of NADPH relative to EMP. On other hand, The expression of maeB gene was enhanced, indicating that the capability of the cells for carboxylating via MaeB was enhanced. The cells produced more NADPH, favoring the carboxylation via MaeB.

(2) The expression level of transhydrogenase gene sthA was increased, indicating the ability of the cells of converting NADPH into NADH was enhanced. The cells produced more NADPH which was in turn converted into NADH for providing reducing equivalent for succinate production.

Example 13: Sequencing Analysis of lpdA Gene of the Recombinant E. coli HX024

Figure 8A:
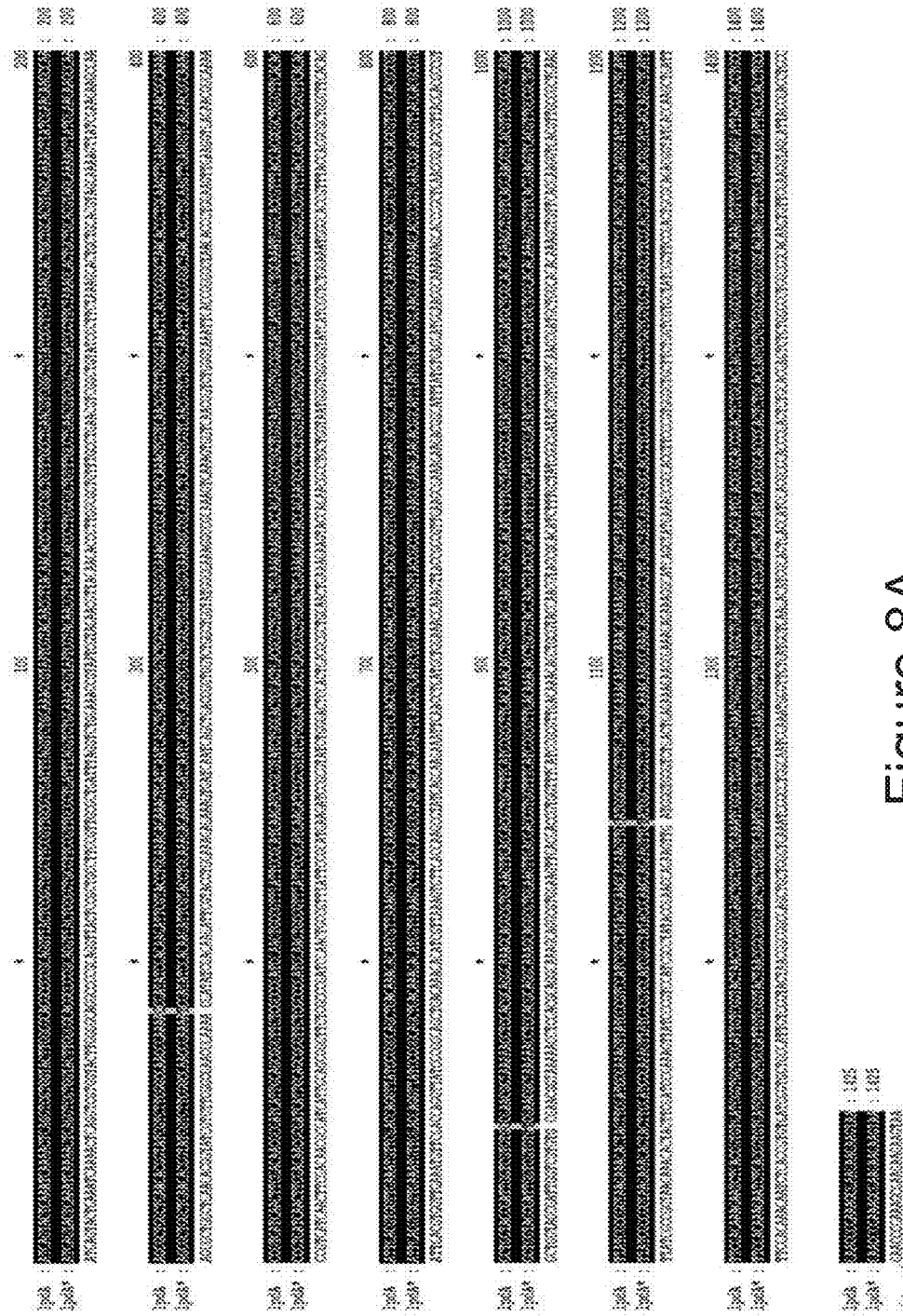
FIG. 8: (A) Nucleotide sequence alignment between wild-type lpdA gene and mutant lpdA gene (lpdA*); (B) Amino acid sequence alignment between polypeptides encoded by wild-type lpdA gene and mutant lpdA gene (lpdA*).
Figure 8B:
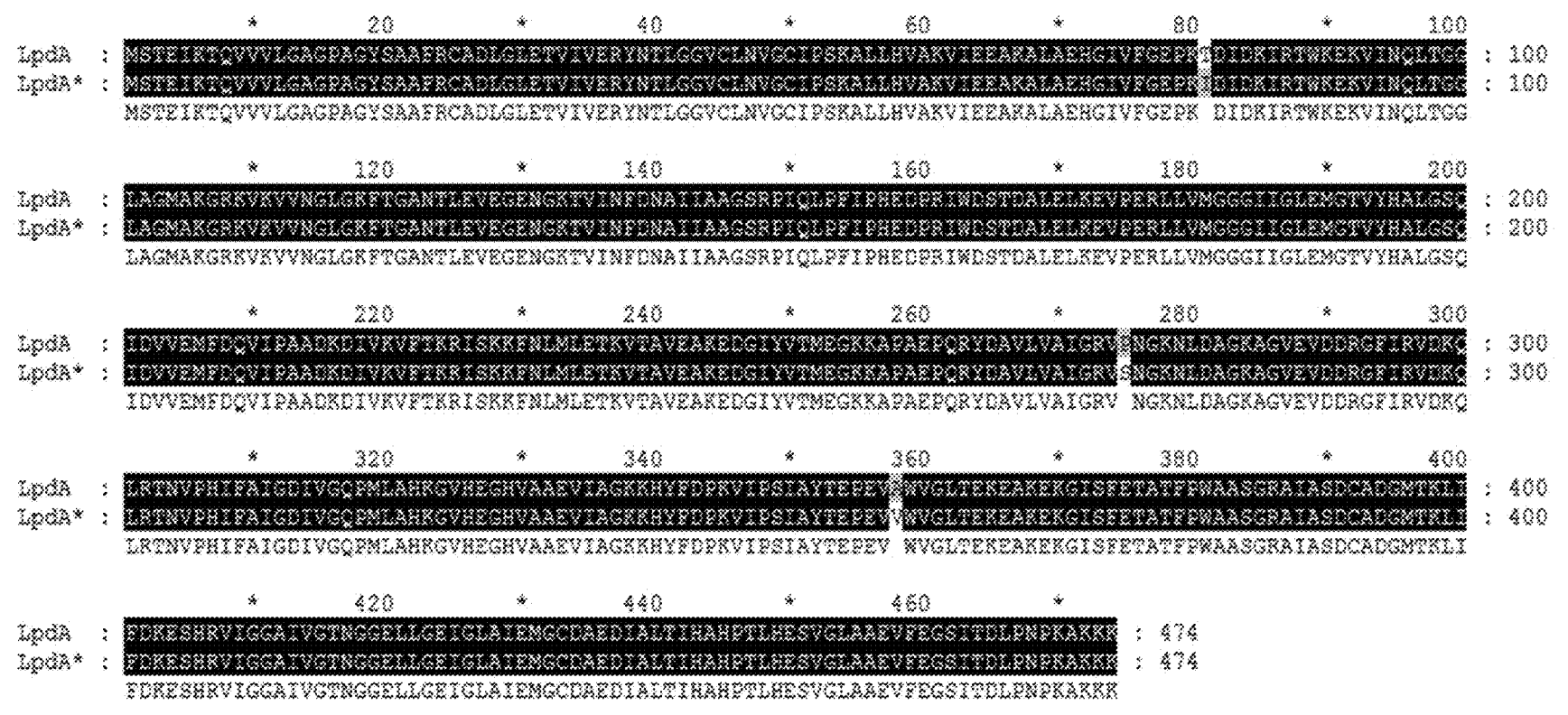

Genome sequencing of the recombinant E. coli HX024 was performed by BGI (Beijing, China). The results showed that three nucleotide mutations (C242T, C823T and C1073T) were found in the coding region of lpdA gene (GenBank No: ACA79157.1), leading to three changed amino acids (T81I, P275S and A358V) (FIG. 8)

Example 14: Activation of TtkA and SthA Improves Succinate Production (1) Construction of Recombinant E. coli ZT-251, ZT-252 and ZT-253

The native promoter of tktA gene (GenBank No: ACA76448.1) from the strain Suc-T110 was replaced by the artificial regulatory part M1-37 (SEQ ID No:109) to obtain the strain ZT-251.

The recombinant strain ZT-251 was constructed as follows:

First homologous recombination: taking plasmid pXZ-CS as template, the DNA fragment I of 2717 bp for the first homologous recombination was amplified with a primer set tktA-cat-sacB-up (SEQ ID No:79) and tktA-cat-sacB-down (SEQ ID No:80). The primer set are listed in Table 2. The obtained DNA fragment I was electroporated into the strain Suc-T110 harboring the plasmid pKD46. The ampicillin- and chloramphenicol-resistant colonies were screened out to obtain intermediate recombinant strains.

Second homologous recombination: taking the genome DNA of E. coli M1-37 (Lu et al., 2012, Appl Microbiol Biotechnol. 93:2455-2462; SEQ ID No:109) as template, PCR was performed with a primer set tktA-P-up (SEQ ID No:81) and tktA-RBS-down (SEQ ID No:82) to obtain DNA fragment tktA-M1-37 (193 bp) containing flanking homologous arms of tktA promoter and the artificial regulatory part M1-37. The primers used are listed in Table 2.

The fragment tktA-M1-37 of 193 bp was electroporated into the intermediate recombinant strains to obtain recombinant bacteria. The methods of electroporation and clone screening were the same as described in the sixth step of the section (1-2) of Example 1 for deleting ldhA gene.

The recombinant bacteria were verified by PCR with a primer set tktA-YZ-up (SEQ ID No:83)/tktA-YZ-down (SEQ ID No:84) and sequenced, and the positive colony verified by sequencing was designated as ZT-251.

Using the same method, the native promoter of the gene sthA (GenBank No: ACA79653.1) in the strain Suc-T110 was replaced with the artificial regulatory part M1-37 to obtain the strain ZT-252. The primers used are listed in Table 2. The primers were named in same manner as those used for replacing promoter of the gene tktA, while only tktA was replaced by sthA.

Using the same method, the native promoters of the sthA and tktA genes in the strain Suc-T110 were replaced with the artificial regulatory part M1-37 (SEQ ID No:109) to obtain the strain ZT-253. The primers used are listed in Table 2.

(2) Fermentation of Recombinant E. coli ZT-251, ZT-252 and ZT-253

Fermentation of recombinant strains ZT-251, ZT-252 and ZT-253 were carried out as described in Example 2. The results of fermentation were shown in Table 9. When improving the expression of tktA gene from PPP in strain Suc-T110, the succinate titer and yield were increased by 4% and 13%, respectively. The enhanced expression of tktA gene could enhance the carbon flux through PPP, increasing the reducing equivalent for succinate production.

When improving the expression of sthA gene, the succinate titer and yield were increased by 5% and 13%, respectively. The enhanced expression of sthA gene could catalyze part of NADPH in cells to be converted to NADH for succinate production.

When improving the expression of tktA and sthA genes at the same time, the succinate titer and yield were increased by 10% and 19%, respectively. NADPH generated by PPP was converted to NADH for succinate production. In NBS medium with higher 7% glucose, the succinate higher-producing strain ZT-253 could produce 506 mM of succinate with a yield of 1.36 mol/mol.

TABLE 9

Effect of SthA and TktA on the succinate production

| Strain[a] | Genetic modification | Cell mass (g/L) | Succinate yield (g/g) | Succinate yield (mol/mol) | Fermentation products (mM) succinate | Fermentation products (mM) acetate |
|---|---|---|---|---|---|---|
| Suc-T110[b] | | 1.53 | 0.73 ± 0.02 | 1.12 ± 0.03 | 280 ± 10 | 96 ± 10 |
| ZT-251[b] | Suc-T110, M1-37-tktA | 1.36 | 0.83 ± 0.01 | 1.26 ± 0.02 | 290 ± 11 | 74 ± 6 |
| ZT-252[b] | Suc-T110, M1-37-sthA | 1.24 | 0.83 ± 0.01 | 1.27 ± 0.02 | 293 ± 13 | 64 ± 2 |
| ZT-253[b] | Suc-T110, M1-37-tktA, M1-37-sthA | 1.22 | 0.87 ± 0.01 | 1.33 ± 0.01 | 307 ± 4 | 56 ± 7 |
| ZT-253[c] | Suc-T110, M1-37-tktA, M1-37-sthA | 1.24 | 0.89 ± 0.01 | 1.36 ± 0.02 | 506 ± 8 | 85 ± 10 |

[a]500-ml fermentation vessel, 250 ml fermentation medium. The fermentation medium contains 100 mM KHCO$_3$. The used neutralizer was 2.4M K$_2$CO$_3$ and 1.2M KOH.
[b]The initial glucose concentrate was 5%.
[c]The initial glucose concentrate was 7%.

Example 15: Activation of TktA, SthA and Pyruvate Dehydrogenase for Improving Succinate Production (1) Construction of Recombination E. coli ZT-273

Using the same method described in (1) of Example 14, the native promoter of aceEF gene in the strain ZT-253 was replaced with the artificial regulatory part M1-93. The primers were named in same manner as those used for replacing promoter of the gene tktA, and only tktA was replaced by aceEF (Table 2). The obtained intermediate recombinant strain ZT273A was verified with a primer set AP1-up (SEQ ID No:95)/aceEF-1(SEQ ID No:96).

The lpdA* was integrated into ackA site of the intermediate recombinant strain ZT-273A to obtain the intermediate recombinant strain ZT-273B. The detail processes were as follows.

First step: construction of the integration vector pTrc99A-M-Kan.

Specifically, taking plasmid pKD4 (Datsenko and Wanner 2000, Proc Natl Acad Sci USA 97:6640-6645; pKD4 was purchased from CGSC E. coli culture collection center of Yale University) as template, a FRT-km fragment was amplified with a primer set Kan-up-PacI (SEQ ID No:97)/Kan-down-EcoRI (SEQ ID No:98). The PCR system and cycles were referred to the first step in section (1-1) of Example 1 for construction of pXZ-CS. The FRT-km fragment was digested with restriction endonuclease PacI/EcoRI (NEB) at 37° C. for 30 minutes, and pTrc99A-M (Zhao et al 2013, Met Eng 17:42-50, constructed by our lab, having the sequence of SEQ ID NO: 111) was digested using the same enzymes under same conditions. The digested products were cleaned using Purification Kit Cleaning Gel/PCR Extraction kit (BioMIGA Biotechnology Company). 50 ng of the purified FRT-Km fragment and 30 ng of the purified pTrc99A-M vector fragment were added with 2 μl of 10× T4 ligation buffer (NEB), 1 μl of T4 polynucleotide kinase (NEB), supplemented with distilled water to a final volume of 20 μl, and reacted at 37° C. for 30 minutes. 1 μl of T4 ligase (NEB, 400,000 cohesive end units/ml) was added and reacted at room temperature for 2 hours to obtain ligation product. 10 μl of the ligation product was transformed into Trans10 by CaCl$_2$-transformation, as described in the fourth step in section (1-1) of Example 1 for construction of plasmid pXZ-CS. 200 μl of the transformed cells were plated onto a LB plate containing kanamycin (final concentration of 50 μg/mL) and ampicillin (final concentration of 50 μg/mL), and grown for overnight. 2-3 clones were selected and verified by PCR with a primer set Kan-F (SEQ ID No:99)/pTrc99A-R (SEQ ID No:100). The correct plasmid was designated as pTrc99A-M-Kan.

Second step, lpdA* gene was cloned into the integration vector pTrc99A-M-Kan to obtain plasmid pXZ177

Specifically, the plasmid pXZ174 was digested with SacI/HindIII (NEB) at 37° C. for 30 minutes and the 1455 bp fragment was recovered from gel. pTrc99AM-Kan was digested with the same enzymes. The digested products were cleaned using Purification Kit Cleaning Gel/PCR Extraction kit (BioMIGA Biotechnology Company). 50 ng of the recovered fragment and 20 ng of pTrc99AM-Kan vector fragment were added with 2 μl of 10× T4 ligation buffer (NEB), 1 μl of T4 polynucleotide kinase (NEB), supplemented with distilled water to a final volume of 20 μl, and reacted at 37° C. for 30 minutes. 1 μl of T4 ligase (NEB, 400,000 cohesive end units/ml) was added and reacted at room temperature for 2 hours to obtain ligation product. 5 μl of the ligation product was transformed into Trans1-T1 competent cells (Beijing TransGen Biotech), and 200 μl of the transformed cells were plated onto a LB plate containing kanamycin (final concentration of 50 μg/mL) and ampicillin (final concentration of 100 μg/mL), and grown for overnight. 5 positive colonies were picked and validated by colony PCR with a primer set Kan-F/lpdA-R-170 (SEQ ID No:101). The sequencing results showed correct construction of the plasmid which was designated as pXZ177.

Third step, the lpdA* fragment was integrated into ackA site of strain ZT-273A.

Preparation of the fragment for one-step recombination: taking pXZ177 as template, the fragment for one-step recombination was amplified with a primer set ackA-FRT-up (SEQ ID No:102)/pta-rrnB-down (SEQ ID No:103), containing 50 bp left homologous arm of ackA, FRT-km-lpdA* sequence and 50 bp right homologous arm of ackA.

One-step recombination: plasmid pKD46 was transformed into strain ZT-273A by CaCl$_2$-transformation, and then the fragment for one-step recombination was electroporated into ZT-273 strain harboring pKD46. The electroporation program was the same as described in the fourth step of section (1-2) of Example 1 for deleting ldhA gene. 200 μl of transformed competent cells were plated onto a LB plate containing chloramphenicol (final concentration of 17 μg/mL) and grown at 37° C. for overnight. 5 colonies were verified by colony PCR with a primer set XZ-ackA-up (SEQ ID No:39)/lpdA-R-170 (SEQ ID No:101). The correct one was designated as ZT-273B.

Using the method as described in section (1) of Example 14, the artificial regulatory part M1-93 was inserted in front of the lpdA*gene in ZT-273B. The primers were named in the same manner as those for modulating tktA gene, and only tktA was replaced by ackA or lpdA (Table 2). The obtained strain was designated as ZT-273.

(2) Fermentation of Recombinant E. coli ZT-273

Following the method of Example 2, the fermentation of the strain was carried out.

The results of fermentation were shown in Table 10. When the expression of both tktA and sthA genes were enhanced in the strain Suc-T110, the succinate titer and yield were increased by 10% and 19%, respectively. On this basis, further activation of pyruvate dehydrogenase produced extra reducing equivalent to succinate production. Compared with Suc-T110, the succinate titer and yield by the recombinant E. coli ZT-273 were increased by 24% and 34%, respectively, with a yield of up to 1.5 mol/mol. In addition, the succinate high-producing strain ZT-273 produced succinate with a titer of 566 mM and a yield of 1.48 mol/mol in the fermentation medium containing higher concentration of sugar (7% glucose).

TABLE 10

The effects of SthA, TktA and Pyruvate Dehydrogenase activities on succinate production

| Strain[a] | Genetic modification | Cell mass (g/L) | Succinate yield (g/g) | succinate yield (mol/mol) | Fermentation products (mM)[d] succinate | acetate |
|---|---|---|---|---|---|---|
| Suc-T110[b] | | 1.53 | 0.73 ± 0.02 | 1.12 ± 0.03 | 280 ± 10 | 96 ± 10 |
| ZT-253[b] | Suc-T110, M1-37-tktA, M1-37-sthA | 1.22 | 0.87 ± 0.01 | 1.33 ± 0.01 | 307 ± 4 | 56 ± 7 |
| ZT-273[b] | ZT-253, M1-93-aceEF, ackA::M1-93-lpdA* | 1.52 | 0.98 ± 0.01 | 1.50 ± 0.02 | 346 ± 10 | 18 ± 2 |
| ZT-273[c] | ZT-253, M1-93-aceEF, ackA::M1-93-lpdA* | 1.65 | 0.97 ± 0.01 | 1.48 ± 0.02 | 566 ± 12 | 29 ± 5 |

[a]500-ml fermentation vessel, 250 ml fermentation medium. The fermentation medium contains 100 mM KHCO$_3$. The used neutralizer was 2.4M K$_2$CO$_3$ and 1.2M KOH.
[b]The initial glucose concentration was 5%.
[c]The initial glucose concentration was 7%.

The recombinant E. coli obtained in this invention was compared with the recombinant E. coli by others (Table 11), and the following conclusion can be obtained.

(1) Among these strains, the strain HX028 of the invention has the highest titer and yield of succinate under the same fermentation conditions. Compared with the strains KJ073 and KJ122 cultured with potassium salts, the fermentation of the strain of the invention was used with sodium salts and thus has much lower cost. In addition, as the activated pentose phosphate pathway is capable of generating $CO_2$, the fermentation of the strains HX024 and HX028 of the invention would demand less bicarbonate ions. The neutralizer consists of 1.5M $Na_2CO_3$+3M NaOH instead of 2.4M $Na_2CO_3$+1.2M NaOH, and the succinate titer and yield were substantially the same, which decrease the amount of sodium carbonate and the cost of production.

2) The strains AFP111 and SBS550MG produced succinate with yields of 1.68 and 1.61 mol/mol, respectively. However, they require rich medium for fermentation, increasing the cost of production and leading to high yield due to the carbon source contained in the medium. For example, the strain AFP111 produced 99.2 g/L of succinate with a yield of 1.68 mol/mol (1.1 g/g), 10 g/L of acetate and 5 g/L of ethanol (Vemuri et al., 2002, J. Ind. Microbiol Biotechnol 28: 325-332). It can be deduced that the consumption of glucose was 90.2 g/L. However, 88.6 g/L of glucose was consumed for producing 99.2 g/L succinate (1 g glucose converted into 1.12 g succinate); 15 g/L glucose for 10 g/L acetate (1 mol glucose converted to 2 mol acetate); and 9.2 g/L glucose for 5 g/L ethanol (1 mol glucose converted to 2 mol ethanol), respectively. The theoretically total consumed glucose was 88.6+15+9.2=112.8 g/L, which was more than the actual consumed glucose by 112.8−90.2=22.6 g/L, because the fermentation medium was added with 10 g/L yeast extract and 20 g/L peptone. If glucose was the only carbon source in the fermentation medium, the yield of succinate can be decreased dramatically. It can be calculated that at the most only 88.6/112.8=78.5% of glucose was used for succinate synthesis, and 21.5% of glucose was used for acetate and ethanol synthesis. The yield of succinate was only 78.5%× 1.71=1.34 mol/mol.

In addition, both AFP111 and SBS550MG strains were fermented by the aerobic-anaerobic two-step fermentation. Air needs to be aerated during aerobic fermentation, increasing energy consumption, reducing the utilization rate of the fermentation vessel and increasing the cost of production.

3) The strain KJ073 produced succinate mainly by the PCK carboxylation. The succinate titer was decreased by 88% when pck gene deleted alone. The other three carboxylases contributed little to succinate production, and the succinate titers were decreased by 4%, 7% and 7%, respectively, when ppc, maeA and maeB genes were deleted separately (Zhang et al., 2009a, Proc Natl Acad SCI USA 106:20180-20185).

In the succinate high-producing strain HX024 of the invention, four carboxylases contributed to succinate production to certain extent, among which PPC makes the most contribution. If only ppc gene was deleted, the seed culture cannot grow on mineral salts medium. Using LB medium to prepare the seed culture and then fermentated in mineral salts medium, the succinate titer was decreased by 70%. The succinate titers were decreased by 38%, 49% and 29% respectively when pck, maeA or maeB gene was deleted separately.

4) The strain XZ721 (Zhang et al., AEM, 2009b, 75:7807-7813) has a similar background with Suc-T110 derivations and they have not subjected to metabolic evolution.

Compared with Suc-T110, the strain ZT-253 obtained by modifying both tktA and sthA genes increased the succinate titer and yield by 10% and 19%, respectively. Compared with Suc-T110, the strain ZT-273 obtained by modifying tktA, sthA and pyruvate dehydrogenase increased the succinate titer and yield by 24% and 34%, respectively.

The recombinant strain ZT-273 of the invention produces 40.8 g/L (346 mM) succinate with a yield of 0.98 g/g (1.50 mol/mol) by fermentation with 50 g/L glucose, has better production of succinate than XZ721. The recombinant strain ZT-273 produced 66.8 g/L (566 mM) succinate with a yield of 0.97 g/g (1.48 mol/mol) by fermentation with 70 g/L glucose.

TABLE 11

Comparison of succinate productivity of different recombinant *E-coli*

| Strain | Modification | Fermentation condition | Succinate titer (mM) | Succinate yield (mol/mol) | References |
|---|---|---|---|---|---|
| *Comparison of high producing strains* | | | | | |
| HX024 | ATCC 8739, ΔldhA, ΔpflB, ΔptsI, Ppck*-galP, pck*, ΔackA-pta, Ppck*-aceBA, Ppck*-dcuC, ΔmgsA metabolic evolution in medium with sodium | Mineral salts medium, Batch fermentation in anaerobic, 12% glucose | 915 | 1.37 | This invention |
| HX028 | ATCC 8739, ΔldhA, ΔpflB, ΔptsI, Ppck*-galP, pck*, ΔackA-pta, Ppck*-aceBA, Ppck*-dcuC, ΔmgsA, ΔadhE,, ΔtdcDE metabolic evolution in medium with sodium | Mineral salts medium, Batch fermentation in anaerobic, 12% glucose | 1042 | 1.56 | This invention |
| KJ073 | ΔldhA, ΔadhE, ΔfocA-pflB, ΔackA, ΔmgsA, ΔpoxB, metabolic evolution in medium with sodium salts | Mineral salts medium, Batch fermentation in anaerobic, 10% glucose | 668 | 1.2 | Jantama et al., 2008a |
| KJ122 | ΔldhA, ΔadhE, ΔfocA-pflB, ΔackA, ΔmgsA, ΔpoxB, ΔtdcDE, ΔaspC, ΔsfcA | Mineral salts medium, Batch fermentation in anaerobic, | 680 | 1.36 | Jantama et al., 2008b |

TABLE 11-continued

Comparison of succinate productivity of different recombinant E-coli

| Strain | Modification | Fermentation condition | Succinate titer (mM) | Succinate yield (mol/mol) | References |
|---|---|---|---|---|---|
| | metabolic evolution in medium with potassium salts | 10% glucose | | | |
| AFP111 | ΔpflAB, ΔldhA, ΔptsG, over-expressed pyc gene of Rhizobium etli | Rich medium, Aerobic-anaerobic two-step fermentation | 841 | 1.68 | Vemuri et al., 2002 |
| SBS550MG | ΔldhA, ΔadhE, ΔiclR, ΔackA-pta, over-expressed pyc gene of Lactococcus lactis | Rich medium, Aerobic-anaerobic two-step fermentation | 339 | 1.61 | Sanchez et al. 2005 |
| | | Strains with key genes modified | | | |
| XZ721 | pck*, ΔptsI, ΔpflB | Mineral salts medium, Batch fermentation in anaerobic, 5% glucose | 327 | 1.25 | Zhang et al., 2009a |
| Suc-T110 | ΔldhA, ΔpflB, ΔptsI, Ppck*-galP, Ppck*-pck | Mineral salts medium, Batch fermentation in anaerobic, 5% glucose | 280 | 1.12 | This invention |
| ZT-253 | Suc-T110, M1-37-tktA, M1-37-sthA | Mineral salts medium, Batch fermentation in anaerobic, 5% glucose | 307 | 1.33 | This invention |
| ZT-273 | ZT-253, M1-93-aceEF, ackA::M1-93-lpdA* | Mineral salts medium, Batch fermentation in anaerobic, 5% glucose | 346 | 1.50 | This invention |
| ZT-253 | Suc-T110, M1-37-tktA, M1-37-sthA | Mineral salts medium, Batch fermentation in anaerobic, 7% glucose | 506 | 1.36 | This invention |
| ZT-273 | ZT-253, M1-93-aceEF, ackA::M1-93-lpdA* | Mineral salts medium, Batch fermentation in anaerobic, 7% glucose | 566 | 1.48 | This invention |

Example 16: Construction of Recombinant E. coli NZ-512, NZ-513, NZ-514 and NZ-517

(1) Construction of Recombinant E. coli NZ-512 (Table 1) Included the Following Two Steps:

Deletion of alcohol dehydrogenase gene adhE: the adhE gene (GenbankNo: ACA78022.1) from the strain Suc-T110 was deleted to obtain recombinant strain NZ-511 (Table 1), using the method as described in section (1) of Example 1. The plasmids constructed are listed in Table 3, and the primers used are listed in Table 2. The primers were named in same manner as those used for deleting ldhA gene, while only ldhA was replaced with adhE.

Recovery of pyruvate formate-lyase gene pflB: ΔpflB gene from NZ-511 (Table 1) was recovered to the pflB gene (GenBank No: ACA78322.1) of the wild type E. coli ATCC 8739, using the method as described in section (1) of Example 1. DNA fragment of 2260 bp for the second homologous recombination was amplified from the DNA of wild type E. coli ATCC 8739 with a primer set XZ-pflB-up/XZ-pflB-down. The resulting strain was designated as NZ-512 (Table 1). The plasmids constructed are listed in Table 3, and the primers used are listed in Table 2. The primers were named in same manner as those used for deleting ldhA gene, while only ldhA was replaced with pflB.

(2) Construction of Recombinant E. coli NZ-513, NZ-517 and NZ-514 by Activation of TktA and SthA The native promoter of tktA gene (GenBank No:ACA76448.1) in the strain NZ-512 was replaced with the artificial regulatory part M1-37 (SEQ ID No:109) to obtain strain NZ-513 (Table 1), using the method as described in section (1) of Example 14. By the same manner, the native promoter of sthA gene (GenBank No: ACA79653.1) in NZ-512 and NZ-513 was replaced with the artificial regulatory part M1-37 to obtain strains NZ-517 and NZ-514, respectively (Table 1). The primers used are listed in Table 2. The primers were named in same manner as those used for modulating tktA gene, while only tktA was replaced with sthA.

Example 17: Fermentation of Recombinant E. coli NZ-512, NZ-513, NZ-514 and NZ-517

Following the method described in Example 2, the fermentation of the strains was carried out.

The results of fermentation are shown in Table 12. The strain NZ512, with recovered pflB gene and inactivated adhE gene, produced 289 mM of succinate with a yield of 1.18 mol/mol, which showed no significant difference with Suc-T110.

The succinate titer and yield of strain NZ-513, generated by activating tktA gene alone in NZ-512, were 4% and 6% higher than those of NZ-512, respectively. The succinate titer and yield of strain NZ-517, generated by activating sthA gene alone in NZ-512, were 7% and 5% higher than those of NZ-512, respectively. The succinate titer and yield of strain NZ-514, generated by activating both tktA and sthA genes in NZ-512, were 9% and 12% higher than those of NZ-512, respectively. These results showed that tktA and sthA genes had a synergistic effect and could convert NADPH generated in pentose phosphate pathway into NADH for succinate production.

artificial regulatory libraries, was amplified with a primer set zwf-P-up and zwf-RBSL-down. The primers used are listed in Table 2.

The DNA fragment RBSL-zwf of 189 bp was electrotransformed into the intermediate recombination bacteria into which the DNA fragment I was integrated to obtain recombinant bacteria. The methods of electrotransformation and screening were the same as those described in the sixth step for deleting ldhA gene.

The recombinant bacteria were verified by PCR with primer set zwf-YZ-up/zwf-YZ-down, and 10 correct positive colonies verified by sequencing were randomly selected for the subsequent assay of Zwf enzyme activity.

TABLE 12

Succinate production by recombinant E. coli NZ-512, NZ-513, NZ-514 and NZ-517

| Strain[a] | Genetic modification | Cell mass (g/L) | Succinate production (g/g) | Succinate yield (mol/mol) | Fermentation product (mM) | | |
|---|---|---|---|---|---|---|---|
| | | | | | succinate | acetate | formate |
| Suc-T110 | ATCC 8739, ΔldhA, ΔpflB, ΔptsI, Ppck*-galP, Ppck*-pck | 1.53 | 0.73 ± 0.02 | 1.12 ± 0.03 | 280 ± 10 | 96 ± 10 | 0 |
| NZ-512 | ATCC 8739, ΔldhA, ΔptsI, Ppck*-galP, Ppck*-pck, ΔadhE | 1.5 | 0.77 ± 0.01 | 1.18 ± 0.02 | 289 ± 6 | 89 ± 10 | 58 ± 2 |
| NZ-513 | ATCC 8739, ΔldhA, ΔptsI, Ppck*-galP, Ppck*-pck, ΔadhE, M1-37-tktA | 1.54 | 0.82 ± 0.01 | 1.25 ± 0.01 | 300 ± 2 | 60 ± 4 | 60 ± 4 |
| NZ-517 | ATCC 8739, ΔldhA, ΔptsI, ΔadhE, Ppck*-galP, Ppck*-pck, M1-37-sthA | 1.6 | 0.8 ± 0.01 | 1.24 ± 0.01 | 310 ± 3 | 84 ± 2 | 68 ± 2 |
| NZ-514 | ATCC 8739, ΔldhA, ΔptsI, Ppck*-galP, Ppck*-pck, ΔadhE, M1-37-tktA, M1-37-sthA | 1.59 | 0.86 ± 0.02 | 1.31 ± 0.02 | 315 ± 2 | 52 ± 4 | 52 ± 4 |

[a]500-ml fermentation vessel, 250 ml fermentation medium. The fermentation medium contains 100 mM KHCO$_3$. The used neutralizer was 2.4M K$_2$CO$_3$ and 1.2M KOH. The initial glucose concentration was 5%.

Example 18: Activation of Zwf in Suc-T110 for Improvement of Succinate Production (1) Construction of Recombinant E. coli with Zwf Gene Regulation The native promoter of 6-phosphoglucose dehydrogenase gene zwf (GenBank No: ACA77430.1) in the strain Suc-T110 was replaced with artificial regulatory libraries, according to the following process:

First homologous recombination: taking plasmid pXZ-CS as template, the DNA fragment I for the first homologous recombination was amplified using a primer set zwf-cat-sacB-up and zwf-cat-sacB-down. The primers are listed in Table 2. The resultant DNA fragment I of 2717 bp was electrotransformed into E. coli Suc-T108 harboring the plasmid pKD46. The ampicillin- and chloramphenicol-resistant colonies were screened out to obtain the intermediate recombination bacteria.

Second homologous recombination: using genomic DNA of the recombinant E. coli M1-93 (Lu et al. 2012, Appl Microbiol Biotechnol 93: 2455-2462; SEQ ID No:110) as template, the DNA fragment RBSL-zwf of 189 bp, comprising flanking homologous arms of zwf promoter and the (2) Assay of Zwf Activity in the Recombinant Bacteria 30 ml of fermentation broth in median and post exponential phase was centrifuged in a 50 ml centrifuge tube at 4° C., 10,000 rpm for 5 min. The supernatant was discarded, and pellets were collected and washed in 15 ml of 100 mM Tris-HCl buffer two times, suspended in 3 ml of 100 mM Tris-HCl, sonicated in ice-bath (power: 25 W; On: 1 s; Off: 3 s) for 3-5 min until clarified, and centrifuged at 4° C., 10,000 rpm for 20 min. The supernatant was collected for enzyme activity assay.

Zwf enzyme activity assay system: 990 μl of reaction buffer (100 mM Tris, 10 mM MgCl$_2$, 1 mM DTT, 0.5 mM NADP$^+$, 2 mM glucose-6-phosphate; pH 7.5) was added into 10 μl of the above sonicated supernatant, mixed and transferred into a cuvette to read at A340 (Lamed et al. 1980, J Bacteriol 141:1251-1257; Kabir and Shimizu, 2003, J Bacteriol 105:11-31). The blank control was reaction buffer with 10 μl of ddH$_2$O. The coefficient of NAD(P)H at 340 nm is 6.22 cm$^{-1}$ mM$^{-1}$. One unit of enzyme activity was defined as the production of 1 μmol NADPH min$^{-1}$ mg protein$^{-1}$ (3) Fermentation of Recombinant E. coli to Produce Succinate The recombinant strains ZT-311, ZT-312, ZT-313 and ZT-314 with different Zwf activity were screened out through Zwf activity assay from above step (2). In the strain ZT-311, the native promoter of zwf gene in the strain Suc-T110 was replaced with an artificial regulatory part RBSL1-zwf (SEQ ID NO: 142); in the strain ZT-312, the native promoter of zwf gene in the strain Suc-T110 was replaced with an artificial regulatory part RBSL2-zwf (SEQ ID NO: 143); in the strain ZT-313, the native promoter of zwf gene in the strain Suc-T110 was replaced with an artificial regulatory part RBSL3-zwf (SEQ ID NO: 144); and in the strain ZT-314, the native promoter of zwf gene in the strain Suc-T110 was replaced with an artificial regulatory part RBSL4-zwf (SEQ ID NO: 145).

Following the method of Example 2, the anaerobic fermentation of the strains Suc-T110 and ZT-311, ZT-312, ZT-313 and ZT-314 was carried out. The results are shown in Table 13. The results showed that within a certain range, as Zwf activity increased, the succinate titer and yield were increased significantly (FIG. 9), wherein the optimal result occurred when Zwf activity had a moderate value (1.50 U/mg) where the succinate titer and yield of the strain ZT-312 were respectively 338 mM and 1.44 mol/mol, increased by 29% and 29% respectively compared to the strain Suc-T110. This indicated that the increased Zwf activity favors the activation of PPP and provides more reducing equivalent for succinate production.

Figure 9:
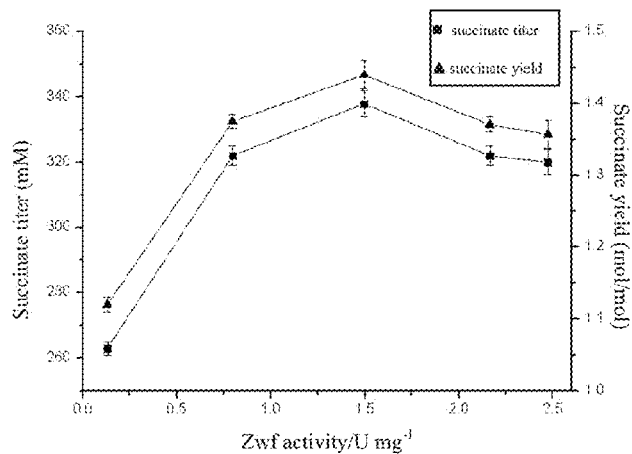
FIG. 9: The relationship between Zwf enzyme activity and succinate yield and titer.

However, on this basis, further increasing Zwf activity, the succinate titer and yield were decreased to a certain extent (FIG. 9). The succinate titer and yield of the strain ZT-313 with higher Zwf activity (Zwf: 2.16 U/mg) were respectively 322 mM and 1.37 mol/mol, reduced by 5% and 5% compared to ZT-312.

(2) Assay of Pgl Activity in the Recombinant Bacteria

The preparation of the crude enzyme solution of the recombinant bacteria was the same as described in Example 18.

Pgl enzyme activity assay system: 990 µl of reaction buffer (25 mM HEPES, 2 mM $MgCl_2$, 1 mM $NADP^+$, 0.5 mM glucose-6-phosphate, 1 U 6-phosphoglucose dehydrogenase; pH 7.1), placed at room temperature for 8 min, and then added with 1.5 U 6-phosphogluconate dehydrogenase and 10 µl of the sonicated supernatant, mixed and transferred into a cuvette to read at A340 (Stanford et al. 2004, Genetics 168:117-127). The blank control was reaction buffer with 10 µl of $ddH_2O$. The coefficient of NAD(P)H at 340 nm is 6.22 $cm^{-1}$ $mM^{-1}$. One unit of enzyme activity was defined as the production of 1 NADPH $min^{-1}$ mg $protein^{-1}$.

(3) Fermentation of Recombinant *E. coli* to Produce Succinate

The recombinant strains ZT-321, ZT-322, ZT-323 and ZT-324 with different Pgl activity were screened out through Pgl activity assay from above step (2), wherein in the strain ZT-321, the native promoter of pgl gene in the strain Suc-T110 was replaced with an artificial regulatory part RBSL1-pgl (SEQ ID NO: 146); in the strain ZT-322, the native promoter of pgl gene in the strain Suc-T110 was replaced with an artificial regulatory part RBSL2-pgl (SEQ ID NO: 147); in the strain ZT-323, the native promoter of pgl gene in the strain Suc-T110 was replaced with an artificial regulatory part RBSL3-pgl (SEQ ID NO: 148); and in the strain ZT-324, the native promoter of pgl gene in the strain Suc-T110 was replaced with an artificial regulatory part RBSL4-pgl (SEQ ID NO: 149).

TABLE 13

Effect of increased Zwf activity in Suc-T110 on succinate production

| Strain[a] | Genetic modification | cell mass (g/L) | succinate production (g/g) | Succinate yield (mol/mol) | Zwf enzyme activity (U/mg) | Fermentation product (mM) | |
|---|---|---|---|---|---|---|---|
| | | | | | | succinate | acetate |
| Suc-T110 | | 1.53 | 0.73 ± 0.02 | 1.12 ± 0.03 | 0.13 ± 0.01 | 263 ± 2 | 90 ± 6 |
| ZT-311 | Suc-T110, RBSL1-zwf | 1.21 | 0.90 ± 0.01 | 1.37 ± 0.01 | 0.80 ± 0.02 | 322 ± 3 | 85 ± 3 |
| ZT-312 | Suc-T110, RBSL2-zwf | 1.47 | 0.94 ± 0.02 | 1.44 ± 0.02 | 1.50 ± 0.03 | 338 ± 4 | 79 ± 3 |
| ZT-313 | Suc-T110, RBSL3-zwf | 1.36 | 0.90 ± 0.01 | 1.37 ± 0.01 | 2.16 ± 0.01 | 322 ± 3 | 76 ± 4 |
| ZT-314 | Suc-T110, RBSL4-zwf | 1.38 | 0.89 ± 0.01 | 1.36 ± 0.02 | 2.47 ± 0.03 | 320 ± 4 | 84 ± 5 |

[a] 500-ml fermentation vessel, 250 ml fermentation medium. The fermentation medium contains 100 mM $KHCO_3$. The used neutralizer was 2.4M $K_2CO_3$ and 1.2M KOH. The initial glucose concentration was 235 mM.

Example 19: The Effect of the Enhanced Pgl Activity in Strain Suc-T110 on Succinate Production (1) Construction of Recombinant *E. coli* with Pgl Gene Regulation The native promoter of 6-phosphogluconolactonase gene pgl (GenBank No: ACA78522.1) in the strain Suc-T110 was replaced with artificial regulatory libraries. The construction method of the recombinant strains was the same as described in Example 18. The primers used are listed in Table 2. The primers were named in same manner as those used for regulating zwf gene, where only zwf was replaced by pgl. 10 correct positive colonies verified by sequencing were randomly selected for the subsequent assay of Pgl activity.

Following the method of Example 2, the anaerobic fermentation of the strains Suc-T110 and ZT-321, ZT-322, ZT-323 and ZT-324 was carried out. The results are shown in Table 14. The results showed that within a certain range, as Pgl activity increased, the succinate titer and yield were increased significantly (FIG. 10), wherein the optimal result occurred when Pgl activity had a moderate value (Pgl: 2.44 U/mg) where the succinate titer and yield of the strain ZT-321 were respectively 321 mM and 1.33 mol/mol, increased by 19% and 19% respectively compared to the strain Suc-T110. This indicated that the increased Pgl activity favors the activation of PPP and provides more reducing equivalent for succinate production.

Figure 10:
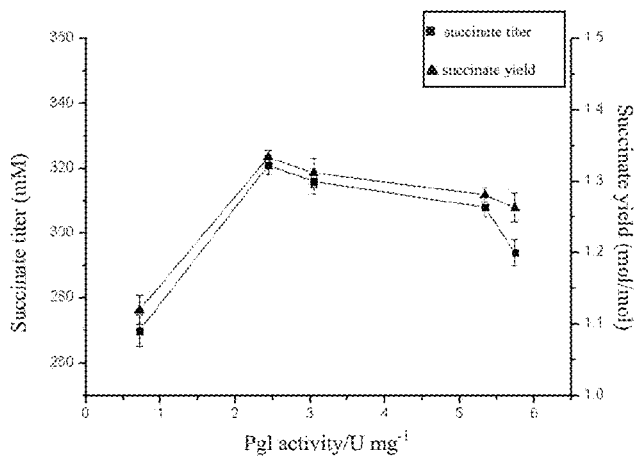
FIG. 10: The relationship between Pgl enzyme activity and succinate yield and titer.

However, on this basis, further increasing Pgl activity, the succinate titer and yield were decreased to a certain extent (FIG. 10). The succinate titer and yield of the strain ZT-323 with higher Pgl activity (Pgl: 5.34 U/mg) were respectively 308 mM and 1.28 mol/mol, reduced by 4% and 4% compared to ZT-321.

(P)H at 340 nm is 6.22 cm$^{-1}$ mM$^{-1}$. One unit of enzyme activity was defined as the production of 1 μmol NADPH min$^{-1}$ mg protein$^{-1}$.

TABLE 14

The effect of enhanced Pgl activity in strain Suc-T110 on succinate production

| Strain[a] | Genetic modification | Cell mass (g/L) | Succinate yield (g/g) | Succinate yield (mol/mol) | Pgl enzyme activity (U/mg) | Fermentation product (mM) | |
|---|---|---|---|---|---|---|---|
| | | | | | | succinate | acetate |
| Suc-T110 | | 1.53 | 0.73 ± 0.02 | 1.12 ± 0.03 | 0.71 ± 0.02 | 270 ± 5 | 89 ± 5 |
| ZT-321 | Suc-T110, RBSL1-pgl | 1.39 | 0.87 ± 0.01 | 1.33 ± 0.01 | 2.44 ± 0.05 | 321 ± 3 | 69 ± 4 |
| ZT-322 | Suc-T110, RBSL2-pgl | 1.68 | 0.86 ± 0.01 | 1.31 ± 0.02 | 3.05 ± 0.03 | 316 ± 4 | 63 ± 4 |
| ZT-323 | Suc-T110, RBSL3-pgl | 1.57 | 0.84 ± 0.01 | 1.28 ± 0.01 | 5.34 ± 0.09 | 308 ± 3 | 69 ± 5 |
| ZT-324 | Suc-T110, RBSL4-pgl | 1.87 | 0.83 ± 0.01 | 1.26 ± 0.02 | 5.74 ± 0.11 | 294 ± 4 | 75 ± 7 |

[a] 500-ml fermentation vessel, 250 ml fermentation medium. The fermentation medium contains 100 mM KHCO$_3$. The used neutralizer was 2.4M K$_2$CO$_3$ and 1.2M KOH. The initial glucose concentration was 241 mM.

Example 20: Effect of Enhanced Gnd Activity in Strain Suc-T110 on Succinate Production (1) Construction of Recombinant *E. coli* with Gnd Gene Regulation The native promoter of 6-phosphogluconate dehydrogenase gene gnd (GenBank No: ACA76645.1) in the strain Suc-T110 was replaced with artificial regulatory libraries. The construction method of the recombinant strains was the same as described in Example 18. The primers used are listed in Table 2. The primers were named in same manner as those used for regulating zwf gene, where only zwf was replaced by gnd. 10 correct positive colonies verified by sequencing were randomly selected for the subsequent assay of Gnd activity.

(2) Assay of Gnd Activity in the Recombinant Bacteria

The preparation of the crude enzyme solution of the recombinant bacteria was the same as described in Example 18.

Gnd enzyme activity assay system: 990 μl of reaction buffer (100 mM Tris, 10 mM MgCl$_2$, 1 mM DTT, 0.5 mM NADP$^+$, 2 mM 6-phosphogluconate; pH 7.5) was added into 10 μl of the sonicated supernatant, mixed and transferred into a cuvette to read at A340 (Padilla et al. 2004, Appl Environ Microbiol 70:370-376). The blank control was reaction buffer with 10 of ddH$_2$O. The coefficient of NAD (3) Fermentation of Recombinant *E. coli* to Produce Succinate The recombinant strains ZT-331, ZT-332, ZT-333 and ZT-334 with different Gnd activity were screened out through Gnd activity assay from above step (2), wherein in the strain ZT-331, the native promoter of gnd gene in the strain Suc-T110 was replaced with an artificial regulatory part RBSL1-gnd (SEQ ID NO: 150); in the strain ZT-332, the native promoter of gnd gene in the strain Suc-T110 was replaced with an artificial regulatory part RBSL2-gnd (SEQ ID NO: 151); in the strain ZT-333, the native promoter of gnd gene in the strain Suc-T110 was replaced with an artificial regulatory part RBSL3-gnd (SEQ ID NO: 152); and in the strain ZT-334, the native promoter of gnd gene in the strain Suc-T110 was replaced with an artificial regulatory part RBSL4-gnd (SEQ ID NO: 153).

Following the method of Example 2, the anaerobic fermentation of the strains Suc-T110 and ZT-331, ZT-332, ZT-333 and ZT-334 was carried out. The results are shown in Table 15. The results showed that within a certain range, as Gnd activity increased, the succinate titer and yield were increased significantly (FIG. 11), wherein the optimal result occurred when Gnd activity had a moderate value (Gnd: 5.71 U/mg) where the succinate titer and yield of the strain ZT-333 were respectively 320 mM and 1.31 mol/mol, increased by 17% and 17% respectively compared to the strain Suc-T110. This indicated that the increased Gnd activity favors the activation of PPP and provides more reducing equivalent for succinate production.

Figure 11:
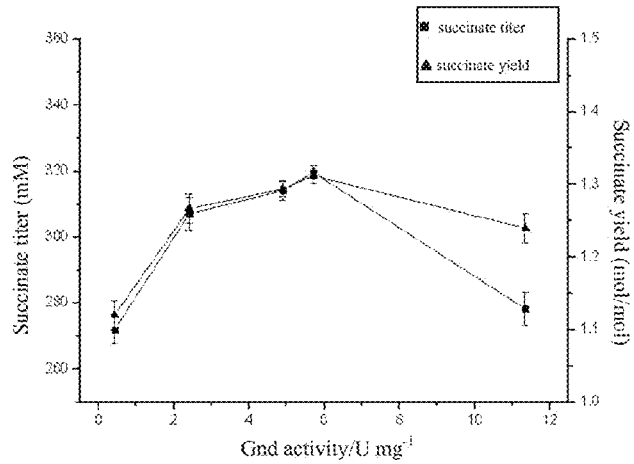
FIG. 11: The relationship between Gnd enzyme activity and succinate yield and titer.

However, on this basis, further increasing Gnd activity, the succinate titer and yield were decreased to a certain extent (FIG. 11). The succinate titer and yield of the strain ZT-334 with higher Gnd activity (Gnd: 11.3 U/mg) were respectively 278 mM and 1.24 mol/mol, reduced by 13% and 5% compared to ZT-333, respectively.

(3) Fermentation of Recombinant *E. coli* to Produce Succinate

The recombinant strains ZT-361, ZT-362 and ZT-363 with different Tkt activity were screened out through Tkt activity

TABLE 15

The effect of enhanced Gnd activity in strain Suc-T110 on succinate production

| Strain [a] | Genetic modification | Cell mass (g/L) | Succinate yield (g/g) | Succinate yield (mol/mol) | Gnd enzyme activity (U/mg) | Fermentation product (mM) succinate | acetate |
|---|---|---|---|---|---|---|---|
| Suc-T110 | | 1.53 | 0.73 ± 0.02 | 1.12 ± 0.02 | 0.42 ± 0.02 | 273 ± 4 | 93 ± 4 |
| ZT-331 | RBSL1-gnd Suc-T110, | 1.46 | 0.83 ± 0.01 | 1.27 ± 0.02 | 2.41 ± 0.06 | 308 ± 5 | 62 ± 5 |
| ZT-332 | RBSL2-gnd Suc-T110, | 1.39 | 0.85 ± 0.01 | 1.29 ± 0.01 | 4.90 ± 0.10 | 314 ± 3 | 80 ± 7 |
| ZT-333 | RBSL3-gnd Suc-T110, | 1.75 | 0.86 ± 0.01 | 1.31 ± 0.01 | 5.71 ± 0.16 | 320 ± 2 | 78 ± 6 |
| ZT-334 | RBSL4-gnd | 1.16 | 0.81 ± 0.01 | 1.24 ± 0.02 | 11.3 ± 0.23 | 278 ± 5 | 82 ± 10 |

[a] 500-ml fermentation vessel, 250 ml fermentation medium. The fermentation medium contains 100 mM KHCO$_3$. The used neutralizer was 2.4M K$_2$CO$_3$ and 1.2M KOH. The initial glucose concentration was 244 mM.

Example 21: Effect of Enhanced Tkt Activity in Strain Suc-T110 on Succinate Production (1) Construction of Recombinant *E. coli* with tktA Gene Regulation The native promoter of transketolase gene tktA (GenBank No:ACA76448.1) in the strain Suc-T110 was replaced with artificial regulatory libraries. The construction method of the recombinant strains was the same as described in Example 18. The primers used are listed in Table 2. The primers were named in same manner as those used for regulating zwf gene, where only zwf was replaced by tktA. 10 correct positive colonies verified by sequencing were randomly selected for the subsequent assay of Tkt activity.

(2) Assay of Tkt Activity in the Recombinant Bacteria

The preparation of the crude enzyme solution of the recombinant bacteria was the same as described in Example 18.

Tkt enzyme activity assay system: 10 μl of crude enzyme was added into 990 μl of reaction buffer (50 mM Tris, 0.24 mM MgCl$_2$, 0.01 mM TPP, 0.25 mM NADH, 3 U glycerol-3-phosphatedehydrogenase, 10 U acetone phosphateisomerase, 0.5 mM D-xylulose 5-phosphate, 0.5 mM Ribose 5-phosphate; pH 7.5), mixed and transferred into a cuvette to read at A340. The blank control was reaction buffer with 10 μl of ddH$_2$O. The coefficient of NAD(P)H at 340 nm is 6.22 cm$^{-1}$ mM$^{-1}$. One unit of enzyme activity was defined as the production of 1 μmol NADPH min$^{-1}$ mg protein$^{-1}$.

assay from above step (2), wherein in the strain ZT-361, the native promoter of tktA gene in the strain Suc-T110 was replaced with the artificial regulatory part RBSL1-tktA (SEQ ID NO: 154); in the strain ZT-362, the native promoter of tktA gene in the strain Suc-T110 was replaced with the artificial regulatory part RBSL2-tktA (SEQ ID NO: 155); in the strain ZT-363, the native promoter of tktA gene in the strain Suc-T110 was replaced with the artificial regulatory part RBSL3-tktA (SEQ ID NO: 156), and in the strain ZT-251, the native promoter of tktA gene in the strain Suc-T110 was replaced with the artificial regulatory part M1-37-tktA (SEQ ID NO: 157).

Following the method of Example 2, the anaerobic fermentation of the strains Suc-T110 and ZT-361, ZT-362, ZT-363 and ZT-251 was carried out. The results are shown in Table 16. The results showed that within a certain range, as Tkt activity increased, the succinate titer and yield were increased significantly (FIG. 12), wherein the optimal result occurred when Tkt activity had a moderate value (Tkt: 0.61 U/mg) where the succinate titer and yield of the strain ZT-361 were respectively 326 mM and 1.37 mol/mol, increased by 22% and 22% respectively compared to the strain Suc-T110. This indicated that the increased Tkt activity favors the activation of PPP and provides more reducing equivalent for succinate production.

Figure 12:
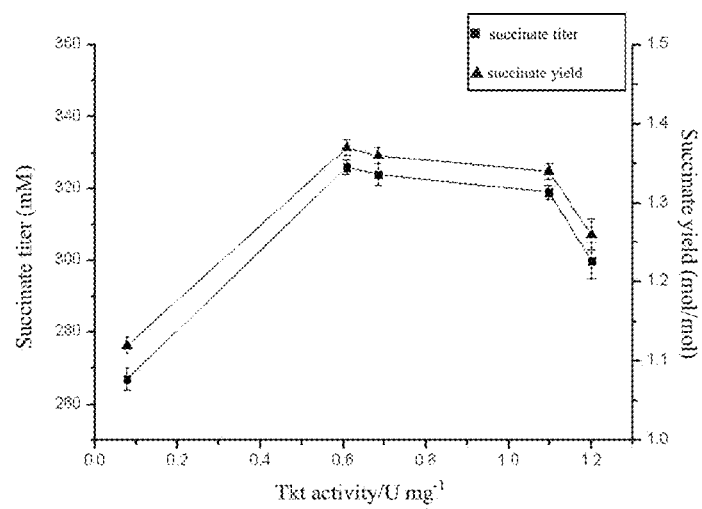
FIG. 12: The relationship between Tkt enzyme activity and succinate yield and titer.

However, on this basis, further increasing Tkt activity, the succinate titer and yield were decreased to a certain extent (FIG. 12). The succinate titer and yield of the strain ZT-251 with higher Tkt activity (Tkt: 1.20 U/mg) were respectively 300 mM and 1.26 mol/mol, reduced by 8% and 8% compared to ZT-361, respectively.

TABLE 16

Effect of enhanced Tkt activity in strain Suc-T110 on succinate production

| Strain [a] | Genetic modification | cell mass (g/L) | succinate production (g/g) | Succinate yield (mol/mol) | Tkt enzyme activity (U/mg) | Fermentation product (mM) | |
|---|---|---|---|---|---|---|---|
| | | | | | | succinate | acetate |
| Suc-T110 | | 1.53 | 0.73 ± 0.01 | 1.12 ± 0.01 | 0.07 ± 0.02 | 267 ± 3 | 91 ± 4 |
| ZT-361 | Suc-T110, RBSL1-tktA | 1.43 | 0.90 ± 0.01 | 1.37 ± 0.01 | 0.61 ± 0.01 | 326 ± 2 | 60 ± 5 |
| ZT-362 | Suc-T110, RBSL2-tktA | 1.39 | 0.90 ± 0.01 | 1.36 ± 0.01 | 0.68 ± 0.02 | 324 ± 3 | 61 ± 4 |
| ZT-363 | Suc-T110, RBSL3-tktA | 1.57 | 0.88 ± 0.01 | 1.34 ± 0.01 | 1.10 ± 0.05 | 319 ± 2 | 62 ± 6 |
| ZT-251 | Suc-T110, M1-37-tktA | 1.36 | 0.83 ± 0.01 | 1.26 ± 0.02 | 1.20 ± 0.07 | 300 ± 5 | 77 ± 6 |

[a] 500-ml fermentation vessel, 250 ml fermentation medium. The fermentation medium contains 100 mM KHCO$_3$. The used neutralizer was 2.4M K$_2$CO$_3$ and 1.2M KOH. The initial glucose concentration was 238 mM.

Example 22: Effect of Enhanced TalB Activity in Strain Suc-T110 on Succinate Production (1) Construction of Recombinant *E. coli* with talB Regulation The native promoter of transaldolase gene talB (GenBank No: ACA79258.1) in the strain Suc-T110 was replaced with artificial regulatory libraries. The construction method of the recombinant strains was the same as described in Example 18. The primers used are listed in Table 2. The primers were named in same manner as those used for regulating zwf gene, while only zwf was replaced by talB. 10 correct positive colonies verified by sequencing were randomly selected for the subsequent assay of Tal activity.

(2) Assay of Tal Activity in the Recombinant Bacteria

The preparation of the crude enzyme solution of the recombinant bacteria was the same as described in Example 18, except for using 50 mM HEPES buffer (pH 8.5).

Tal activity assay: 10 μl of crude enzyme was added into 990 μl of reaction buffer (50 mM HEPES, 0.24 mM MgCl$_2$, 0.5 mM NADP$^+$, 10 U glucose-6-phosphate isomerase, 3 U glucose 6-phosphatedehydrogenase, 0.5 mM D-7-sedoheptulose, 0.5 mM 3-Phosphoglyceraldehyde; pH 8.5), mixed and transferred into a cuvette to read at A340 (Sprenger et al. 1995, J Bacteriol 177:5930-5936). The blank control was reaction buffer with 10 μl of ddH$_2$O. The coefficient of NAD(P)H at 340 nm is 6.22 cm$^{-1}$ mM$^{-1}$. One unit of enzyme activity was defined as the production of 1 μmol NADPH min$^{-1}$ mg protein$^{-1}$.

(3) Fermentation of Recombinant *E. coli* to Produce Succinate

The recombinant strains ZT-371, ZT-372, ZT-373 and ZT-374 with different Tal activity were screened out through Tal activity assay from above step (2), wherein in the strain ZT-371, the native promoter of talB gene in the strain Suc-T110 was replaced with the artificial regulatory part RBSL1-talB (SEQ ID NO: 158); in the strain ZT-372, the native promoter of talB gene in the strain Suc-T110 was replaced with the artificial regulatory part RBSL2-talB (SEQ ID NO: 159); in the strain ZT-373, the native promoter of talB gene in the strain Suc-T110 was replaced with the artificial regulatory part RBSL3-talB (SEQ ID NO: 160); and in the strain ZT-374, the native promoter of talB gene in the strain Suc-T110 was replaced with the artificial regulatory part RBSL4-talB (SEQ ID NO: 161).

Following the method of Example 2, the anaerobic fermentation of the strains Suc-T110 and ZT-371, ZT-372, ZT-373 and ZT-374 were carried out. The results are shown in Table 17. The results showed that within a certain range, as Tal activity increased, the succinate titer and yield were increased significantly (FIG. 13), wherein the optimal result occurred when Tal activity had a moderate value (Tal: 0.20 U/mg) where the succinate titer and yield of the strain ZT-372 were respectively 338 mM and 1.42 mol/mol, increased by 27% and 27% respectively compared to the strain Suc-T110. This indicated that the increased Tal activity favors the activation of PPP and provides more reducing equivalent for succinate production.

Figure 13:
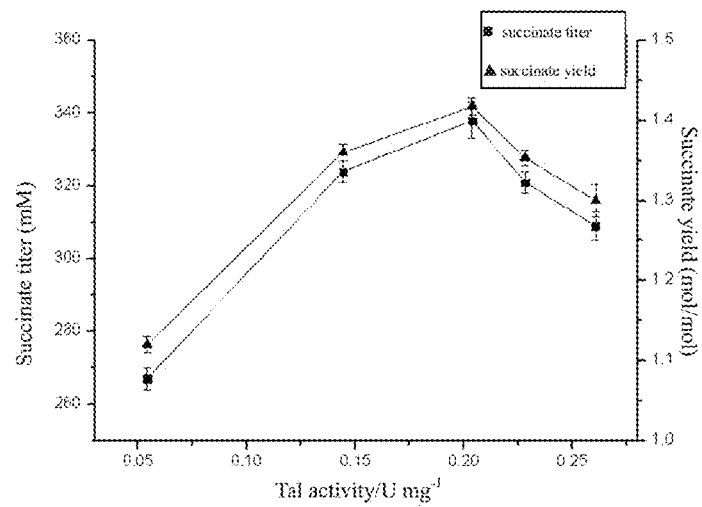
FIG. 13: The relationship between Tal enzyme activity and succinate yield and titer.

However, on this basis, further increasing Tal activity, the succinate titer and yield were decreased to a certain extent (FIG. 13). The succinate titer and yield of the strain ZT-374 with higher Tal activity (Tal: 0.26 U/mg) were respectively 309 mM and 1.30 mol/mol, reduced by 8% and 8% compared to ZT-372, respectively.

TABLE 17

Effect of enhanced TalB activity in strain Suc-T110 on succinate production

| Strain [a] | Genetic modification | Cell mass (g/L) | Succinate yield (g/g) | Succinate yield (mol/mol) | Tal enzyme activity (U/mg) | Fermentation product (mM) | |
|---|---|---|---|---|---|---|---|
| | | | | | | succinate | acetate |
| Suc-T110 | | 1.53 | 0.73 ± 0.01 | 1.12 ± 0.01 | 0.054 ± 0.001 | 267 ± 3 | 90 ± 4 |
| ZT-371 | Suc-T110, RBSL1-talB | 1.46 | 0.90 ± 0.01 | 1.36 ± 0.01 | 0.14 ± 0.02 | 324 ± 3 | 68 ± 7 |
| ZT-372 | Suc-T110, RBSL2-talB | 1.40 | 0.90 ± 0.01 | 1.42 ± 0.01 | 0.20 ± 0.03 | 338 ± 5 | 62 ± 9 |
| ZT-373 | Suc-T110, RBSL3-talB | 1.55 | 0.88 ± 0.01 | 1.35 ± 0.01 | 0.23 ± 0.01 | 321 ± 3 | 55 ± 4 |

TABLE 17-continued

Effect of enhanced TalB activity in strain Suc-T110 on succinate production

| Strain[a] | Genetic modification | Cell mass (g/L) | Succinate yield (g/g) | Succinate yield (mol/mol) | Tal enzyme activity (U/mg) | Fermentation product (mM) | |
|---|---|---|---|---|---|---|---|
| | | | | | | succinate | acetate |
| ZT-374 | Suc-T110, RBSL4-talB | 1.54 | 0.83 ± 0.01 | 1.30 ± 0.02 | 0.26 ± 0.03 | 309 ± 4 | 75 ± 7 |

[a] 500-ml fermentation vessel, 250 ml fermentation medium. The fermentation medium contains 100 mM $KHCO_3$. The neutralizer used was 2.4M $K_2CO_3$ and 1.2M KOH. The initial glucose concentration was 238 mM.

REFERENCES

Amann E, Ochs B, Abel K J (1988) Tightly regulated tac promoter vectors useful for the expression of unfused and fused proteins in *Escherichia coli*. Gene 69:301-315.

Chatterjee R, Millard C S, Champion K, Clark D P, Donnelly M I (2001) Mutation of the ptsG gene results in increased production of succinate in fermentation of glucose by *Escherichia coli*. Appl Environ Microbiol 67:148-154.

Cheng K K, Wang G Y, Zeng J, Zhang J A (2013) Improved succinate production by metabolic engineering. BioMed Res Int 2013:538790.

Datsenko K A, Wanner B L (2000) One-step inactivation of chromosomal genes in *Escherichia coli* K-12 using PCR products. Proc Natl Acad Sci USA 97(12):6640-6645.

Donnelly M I, Millard C S, Clark D P, Chen M J, Rathke J W (1998) A novel fermentation pathway in an *Escherichia coli* mutant producing succinic acid, acetic acid, and ethanol. Appl Biochem Biotechnol 70-72:187-198.

Dower W J, Miller J F, Ragsdale C W (1988) High efficiency transformation of *E. coli* by high voltage electroporation. Nucleic Acids Res 16:6127-6145.

Glassner D, Datta R (1992) Process for the production and purification of succinic acid. U.S. Pat. No. 5,143,834.

Guettler M, Jain M, Soni B (1996) Process for making succinic acid, microorganisms for use in the process and methods of obtaining the microorganisms. U.S. Pat. No. 5,504,004.

Gunsalus I C, Hand D B (1941) The use of bacteria in the chemical determination of total vitamin C. J Biol Chem 141:853-858.

Jantama K, Haupt M J, Zhang X, Moore J C, Shanmugam K T, Ingram L O (2008) Materials and methods for efficient succinate and malate production. PCT/US2008/057439.

Jantama K, Haupt M J, Svoronos S A, Zhang X, Moore J C, Shanmugam K T, Ingram L O (2008a) Combining metabolic engineering and metabolic evolution to develop nonrecombinant strains of *Escherichia coli* C that produce succinate and malate. Biotechnol Bioeng 99:1140-1153.

Jantama K, Zhang X, Moore J C, Shanmugam K T, Svoronos S A, Ingram L O (2008b) Eliminating side products and increasing succinate yields in engineered strains of *Escherichia coli* C. Biotechnol Bioeng 101:881-893.

Kabir m M, Shimizu K (2003) Gene expression patterns for metabolic pathway in pgi knockout *Escherichia coli* with and without phb genes based on RT-PCR. J Bacteriol 105:11-31.

Kim P, Laivenieks M, Vieille C, Zeikus J G (2004) Effect of overexpression of *Actinobacillus succinogenes* phosphoenolpyruvate carboxykinase on succinate production in *Escherichia coli*. Appl Environ Microbiol 70:1238-1241.

Kim Y M, Cho H S, Jung G Y, Park J M (2011) Engineering the pentose phosphate pathway to improve hydrogen yield in recombinant *Escherichia coli*. Biotechnol Bioeng 108:2941-2946.

Kwon Y D, Lee S Y, Kim P (2006) Influence of gluconeogenic phosphoenolpyruvate carboxykinase (PCK) expression on succinic acid fermentation in *Escherichia coli* under high bicarbonate condition. J Microbiol Biotechnol 16:1448-1452.

Lamed R, Zeikus J G (1980) Glucose Fermentation Pathway of *Thermoanaerobium-Brockii*. J Bacteriol 141:1251-1257.

Lee P C, Lee S Y, Hong S H, Chang H N (2002) Isolation and characterization of a new succinic acid-producing bacterium, *Mannheimia succiniciproducens* MBEL55E, from bovine rumen. Appl Microbiol Biotechnol 58:663-668.

Lee W H, Park J B, Park K, Kim M D, Seo J H (2007) Enhanced production of epsilon-caprolactone by overexpression of NADPH-regenerating glucose 6-phosphate dehydrogenase in recombinant *Escherichia coli* harboring cyclohexanone monooxygenase gene. Appl Microbiol Biotechnol 76:329-338.

Lee W H, Kim M D, Jin Y S, Seo J H (2013) Engineering of NADPH regenerators in *Escherichia coli* for enhanced biotransformation. Appl Microbiol Biotechnol 97:2761-2772.

Lu J, Tang J, Liu Y, Zhu X, Zhang T, Zhang X (2012) Combinatorial modulation of galP and glk gene expression for improved alternative glucose utilization. Appl Microbiol Biotechnol 93:2455-2426.

McKinlay J B, Vieille C, Zeikus J G (2007) Prospects for a bio-based succinate industry. Appl Microbiol Biotechnol 76:727-740.

Millard C S, Chao Y P, Liao J C, Donnelly M I (1996) Enhanced production of succinic acid by overexpression of phosphoenolpyruvate carboxylase in *Escherichia coli*. Appl Environ Microbiol 62:1808-1810.

Mok Y K, Clark D R, Kam K M, Shaw P C, Bsi Y I, (1991) A novel thermophilic restriction endonuclease that recognizes 5' CCNNNNNNNGG 3' and the discovery of a wrongly sequenced site in pACYC177. Nucleic Acids Res 19:2321-2323.

Padilla L, Kramer R, Stephanopoulos G, Agosin E (2004) Overproduction of trehalose: Heterologous expression of *Escherichia coli* trehalose-6-phosphate synthase and trehalose-6-phosphate phosphatase in *Corynebacterium glutamicum*. Appl Environ Microbiol 70:370-376.

Papagianni M (2012) Recent advances in engineering the central carbon metabolism of industrially important bacteria. Microb Cell Fact 11:50.

Sánchez A M, Bennett G N, San K Y (2005) Novel pathway engineering design of the anaerobic central metabolic pathway in *Escherichia coli* to increase succinate yield and productivity. Metab Eng 7:229-239.

Scholten E, Renz T, Thomas J (2009) Continuous cultivation approach for fermentative succinic acid production from crude glycerol by *Basfia succiniciproducens* DD1. Biotechnol Lett 31:1947-1951.

Siedler S, Bringer S, Blank L M, Bott M (2012) Engineering yield and rate of reductive biotransformation in *Escherichia coli* by partial cyclization of the pentose phosphate pathway and PTS-independent glucose transport. Appl Microbiol Biotechnol 93:1459-1467.

Sobota J M, Imlay J A (2011) Iron enzyme ribulose-5-phosphate 3-epimerase in *Escherichia coli* is rapidly damaged by hydrogen peroxide but can be protected by manganese. Proc Natl Acad Sci USA 108:5402-5407.

Sprenger G A (1995) Genetics of pentose-phosphate pathway enzymes of *Escherichia coli* K-12. Arch Microbiol 164:324-330.

Sprenger G A, Schorken U, Sprenger G, Sahm H (1995) Transaldolase B of *Escherichia coli* K-12: cloning of its gene, talB, and characterization of the enzyme from recombinant strains. J Bacteriol 177:5930-5936.

Stanford D R, Whitney M L, Hurto R L, Eisaman D M, Shen W C, Hopper A K (2004) Division of labor among the yeast sol proteins implicated in tRNA nuclear export and carbohydrate metabolism. Genetics 168:117-127.

Vemuri G N, Eiteman M A, Altman E (2002) Succinate production in dual-phase *Escherichia coli* fermentations depends on the time of transition from aerobic to anaerobic conditions. J Ind Microbiol Biotechnol 28:325-332.

Zhang X, Jantama K, Moore J C, Jarboe L R, Shanmugam K T, Ingram L O (2010) Engineering the pathway for succinate production. PCT/US2010/029728.

Zhang X, Jantama K, Moore J C, Jarboe L R, Shanmugam K T, Ingram L O (2009a) Metabolic evolution of energy-conserving pathways for succinate production in *Escherichia coli*. Proc Natl Acad Sci USA 106:20180-20185.

Zhang X, Jantama K, Shanmugam K T, Ingram L O (2009b) Reengineering *Escherichia coli* for succinate production in mineral salts medium. Appl Environ Microbiol 75:7807-7813.

Zhao J, Li Q, Sun T, Zhu X, Xu H, Tang J, Zhang X, Ma Y (2013) Engineering central metabolic modules of *Escherichia coli* for improving β-carotene production. Metab Eng 17:42-50.

The invention claimed is:

1. A recombinant E. coli, comprising the modifications of:
   (1) inhibited expression of the gene(s) involved in phosphoenolpyruvate:sugar phosphotransferase system (PTS), and/or inhibited activities of the protein(s) encoded by the gene(s) involved in phosphoenolpyruvate:sugar phosphotransferase system (PTS),
   (2) inhibited expression of pflB and/or adhE genes, and/or inhibited activities of the proteins encoded by pflB and/or adhE genes,
   (3) inhibited expression of IdhA gene, and/or inhibited activity of the protein encoded by IdhA gene, and
   (4) enhanced expression of galP gene and/or exogenous glf gene, and/or enhanced activities of the proteins encoded by galP gene and/or exogenous glf gene;
   wherein said E. coli further comprises one or more of the modifications of
   (a) enhanced expression of one or more of the genes tktA, talB and pgl, and/or enhanced activities of one or more of the proteins encoded by the genes tktA, talB and pgl;
   wherein said E. coli further comprises a mutant lpdA gene, the polypeptide encoded by which comprises modifications at positions corresponding to the positions T81, P275 and A358 of the amino acid sequence shown in SEQ ID No.: 1, wherein the corresponding positions are determined by aligning the sequence of the polypeptide with SEQ ID No.: 1, and optionally at the position corresponding to T81, T is replaced with I; at the position corresponding to P275, P is replaced with S and at the position corresponding to A358, A is replaced with V,
   optionally, in said E. coli, the expression of the mutant lpdA gene is enhanced, and/or the activity of the protein encoded by said mutant lpdA gene is enhanced,
   wherein pflB gene encodes pyruvate formate lyase (EC No: 2.3.1.54); adhE gene encodes ethanol/acetaldehyde dehydrogenase (EC No: 1.1.1.1, EC No: 1.2.1.10); IdhA gene encodes lactate dehydrogenase A (EC No: 1.1.1.28); galP gene encodes galactose MFS transporter; glf gene encodes glucose transporter Glf; tktA gene encodes transketolase (EC No: 2.2.1.1); talB gene encodes transaldolase (EC No: 2.2.1.2); pgl gene encodes 6-Phosphogluconolactonase (EC No: 3.1.1.31), lpdA gene encodes lipoamide dehydrogenase (EC No: 1.8.1.4).

2. The E. coli of claim 1, wherein said genes involved in phosphoenolpyruvate:sugar phosphotransferase system (PTS) are one or more genes selected from the group consisting of genes ptsI encoding PTS system enzyme I, ptsH encoding PTS system enzyme Hpr, crr encoding PTS system enzyme IIA$^{Glc}$ and ptsG encoding PTS system enzyme IICB$^{Glc}$.

3. The E. coli of claim 1, wherein in said E. coli, the expression of sthA and tktA genes is enhanced, and/or the activities of the proteins encoded by sthA and tktA genes are enhanced, wherein the sthA gene encodes a soluble transhydrogenase (EC No: 1.6.1.1).

4. The E. coli of claim 1, wherein said E. coli further comprises the modifications of
   (5) inhibited expressions of ackA and pta genes, and/or inhibited activities of the proteins encoded by ackA and pta genes;
   (6) enhanced expression of aceBA gene cluster, and/or enhanced activities of the protein(s) encoded by aceBA gene cluster;
   (7) enhanced expression of dcuC gene, and/or enhanced activity of the protein encoded by dcuC gene; and
   (8) inhibited expression of mgsA gene, and/or inhibited activity of the protein encoded by mgsA gene,
   wherein ackA gene encodes acetokinase (EC No: 2.7.2.1); pta gene encodes acetyl transferase (EC No: 2.3.1.8); aceBA gene cluster comprises aceB gene (GenBank No: ACA79615.1) encoding malate synthetase (EC No: 2.3.3.9) and aceA gene (GenBank No: ACA79614.1) encoding isocitrate lyase (EC No: 4.1.3.1); dcuC gene encodes C4 dicarboxylate transporter DcuC; and mgsA gene encodes methyl-glyoxal synthetase (EC No: 4.2.3.3).

5. The E. coli of claim 1, wherein said mutant lpdA gene is in a plasmid or in a chromosome.

6. The E. coli of claim 1, wherein said E. coli is deposited in CGMCC under the deposition No. of CGMCC 7260.

7. The E. coli of claim 1, wherein said E. coli further comprises the modifications of (9) enhanced expression of pck gene, and/or enhanced activity of the protein encoded by pck gene, wherein pck gene encodes phosphoenolpyruvate carboxykinase (EC No: 4.1.1.49).

8. The E. coli of claim 7, wherein said E. coli is deposited in CGMCC under the deposition No. of CGMCC 7259.

9. The E. coli of claim 7, wherein said E. coli further comprises the modifications of
   (10) inhibited expression of adhE gene, and/or inhibited activity of the protein encoded by adhE gene; and
   (11) inhibited expression of tdcDE gene cluster, and/or inhibited activities of the protein(s) encoded by tdcDE gene cluster, wherein adhE gene encodes ethanol/acetaldehyde dehydrogenase (EC No: 1.1.1.1, EC No: 1.2.1.10); and tdcDE gene cluster comprises tdcD gene encoding propionate kinase (EC No: 2.7.2.15) and tdcE gene encoding 2-keto methyl butyrate lyase/methyl propionate lyase (EC No: 2.3.1.54).

10. The *E. coli* of claim 9, wherein said *E. coli* is deposited in CGMCC under the deposition No. of CGMCC 7550.

11. The *E. coli* of claim 7, wherein said *E. coli* also contains the genetic modification(s) of: enhanced expression of aceEF gene cluster, and/or enhanced activities of the protein(s) encoded by aceEF gene cluster, wherein aceEF gene cluster encodes pyruvate complex E1/E2(EC No: 1.2.4.1), comprising aceE gene encoding pyruvate dehydrogenase complex E1 and aceF gene encoding pyruvate dehydrogenase complex E2.

12. A method for producing succinate, comprising culturing the *E. coli* of claim 1.

13. The *E. coli* of claim 1, further comprising the modification of enhanced expression of sthA gene, and/or enhanced activity of the protein encoded by sthA gene.

* * * * *

SEQUENCE LISTING

```
<160> NUMBER OF SEQ ID NOS: 161

<210> SEQ ID NO 1
<211> LENGTH: 474
<212> TYPE: PRT
<213> ORGANISM: Escherichia coli
<220> FEATURE:
<221> NAME/KEY: PEPTIDE
<222> LOCATION: (1)..(474)

<400> SEQUENCE: 1

Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
                20                  25                  30

Val Ile Val Glu Arg Tyr Asn Thr Leu Gly Gly Val Cys Leu Asn Val
            35                  40                  45

Gly Cys Ile Pro Ser Lys Ala Leu Leu His Val Ala Lys Val Ile Glu
        50                  55                  60

Glu Ala Lys Ala Leu Ala Glu His Gly Ile Val Phe Gly Glu Pro Lys
65                  70                  75                  80

Thr Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
                100                 105                 110

Val Asn Gly Leu Gly Lys Phe Thr Gly Ala Asn Thr Leu Glu Val Glu
            115                 120                 125

Gly Glu Asn Gly Lys Thr Val Ile Asn Phe Asp Asn Ala Ile Ile Ala
        130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
                180                 185                 190

Val Tyr His Ala Leu Gly Ser Gln Ile Asp Val Val Glu Met Phe Asp
```

```
                195                 200                 205
Gln Val Ile Pro Ala Ala Asp Lys Asp Ile Val Lys Val Phe Thr Lys
    210                 215                 220
Arg Ile Ser Lys Lys Phe Asn Leu Met Leu Glu Thr Lys Val Thr Ala
225                 230                 235                 240
Val Glu Ala Lys Glu Asp Gly Ile Tyr Val Thr Met Glu Gly Lys Lys
                245                 250                 255
Ala Pro Ala Glu Pro Gln Arg Tyr Asp Ala Val Leu Val Ala Ile Gly
            260                 265                 270
Arg Val Pro Asn Gly Lys Asn Leu Asp Ala Gly Lys Ala Gly Val Glu
        275                 280                 285
Val Asp Asp Arg Gly Phe Ile Arg Val Asp Lys Gln Leu Arg Thr Asn
    290                 295                 300
Val Pro His Ile Phe Ala Ile Gly Asp Ile Val Gly Gln Pro Met Leu
305                 310                 315                 320
Ala His Lys Gly Val His Glu Gly His Val Ala Ala Glu Val Ile Ala
                325                 330                 335
Gly Lys Lys His Tyr Phe Asp Pro Lys Val Ile Pro Ser Ile Ala Tyr
            340                 345                 350
Thr Glu Pro Glu Val Ala Trp Val Gly Leu Thr Glu Lys Glu Ala Lys
        355                 360                 365
Glu Lys Gly Ile Ser Phe Glu Thr Ala Thr Phe Pro Trp Ala Ala Ser
    370                 375                 380
Gly Arg Ala Ile Ala Ser Asp Cys Ala Asp Gly Met Thr Lys Leu Ile
385                 390                 395                 400
Phe Asp Lys Glu Ser His Arg Val Ile Gly Gly Ala Ile Val Gly Thr
                405                 410                 415
Asn Gly Gly Glu Leu Leu Gly Glu Ile Gly Leu Ala Ile Glu Met Gly
            420                 425                 430
Cys Asp Ala Glu Asp Ile Ala Leu Thr Ile His Ala His Pro Thr Leu
        435                 440                 445
His Glu Ser Val Gly Leu Ala Ala Glu Val Phe Glu Gly Ser Ile Thr
    450                 455                 460
Asp Leu Pro Asn Pro Lys Ala Lys Lys Lys
465                 470

<210> SEQ ID NO 2
<211> LENGTH: 1425
<212> TYPE: DNA
<213> ORGANISM: Escherichia coli
<220> FEATURE:
<221> NAME/KEY: gene
<222> LOCATION: (1)..(1425)

<400> SEQUENCE: 2
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atcccttcta agcactgct gcacgtagca      180 aaagttatcg aagaagccaa agcgctggct gaacacggta tcgtcttcgg cgaaccgaaa     240
accgatatcg acaagattcg tacctggaaa gagaaagtga tcaatcagct gaccggtggt     300
ctggctggta tggcgaaagg ccgcaaagtc aaagtggtca acggtctggg taaattcacc     360
ggggctaaca ccctgaagt tgaaggtgag aacggcaaaa ccgtgatcaa cttcgacaac     420
gcgatcattg cagcgggttc tcgcccgatc caactgccgt ttattccgca tgaagatccg     480
```

-continued

```
cgtatctggg actccactga cgcgctggaa ctgaaagaag taccagaacg cctgctggta    540
atgggtggcg gtatcatcgg tctggaaatg ggcaccgttt accacgcgct gggttcacag    600
attgacgtgg ttgaaatgtt cgaccaggtt atcccggcag ctgacaaaga catcgttaaa    660
gtcttcacca agcgtatcag caagaaattc aacctgatgc tggaaaccaa agttaccgcc    720
gttgaagcga aagaagacgg catttatgtg acgatggaag gcaaaaaagc acccgctgaa    780
ccgcagcgtt acgacgccgt gctggtagcg attggtcgtg tgccgaacgg taaaaacctc    840
gacgcaggca aagcaggcgt ggaagttgac gaccgtggtt tcatccgcgt tgacaaacag    900
ctgcgtacca acgtaccgca catctttgct atcggcgata tcgtcggtca accgatgctg    960
gcacacaaag gtgttcacga aggtcacgtt gccgctgaag ttatcgccgg taagaaacac   1020
tacttcgatc cgaaagttat cccgtccatc gcctataccg aaccagaagt tgcatgggtg   1080
ggtctgactg agaaagaagc gaaagagaaa ggcatcagct atgaaaccgc caccttcccg   1140
tgggctgctt ctggtcgtgc tatcgcttcc gactgcgcag acggtatgac caagctgatt   1200
ttcgacaaag aatctcaccg tgtgatcggt ggtgcgattg tcggtactaa cggcggcgag   1260
ctgctgggtg aaatcggcct ggcaatcgaa atgggttgtg atgctgaaga catcgcactg   1320
accatccacg cgcacccgac tctgcacgag tctgtgggcc tggcggcaga agtgttcgaa   1380
ggtagcatta ccgacctgcc gaacccgaaa gcgaagaaga agtaa               1425
```

<210> SEQ ID NO 3
<211> LENGTH: 474
<212> TYPE: PRT
<213> ORGANISM: Escherichia coli
<220> FEATURE:
<221> NAME/KEY: PEPTIDE
<222> LOCATION: (1)..(474)

<400> SEQUENCE: 3

Met Ser Thr Glu Ile Lys Thr Gln Val Val Leu Gly Ala Gly Pro
1               5                   10                  15

Ala Gly Tyr Ser Ala Ala Phe Arg Cys Ala Asp Leu Gly Leu Glu Thr
            20                  25                  30

Val Ile Val Glu Arg Tyr Asn Thr Leu Gly Gly Val Cys Leu Asn Val
        35                  40                  45

Gly Cys Ile Pro Ser Lys Ala Leu Leu His Val Ala Lys Val Ile Glu
    50                  55                  60

Glu Ala Lys Ala Leu Ala Glu His Gly Ile Val Phe Gly Glu Pro Lys
65                  70                  75                  80

Ile Asp Ile Asp Lys Ile Arg Thr Trp Lys Glu Lys Val Ile Asn Gln
                85                  90                  95

Leu Thr Gly Gly Leu Ala Gly Met Ala Lys Gly Arg Lys Val Lys Val
            100                 105                 110

Val Asn Gly Leu Gly Lys Phe Thr Gly Ala Asn Thr Leu Glu Val Glu
        115                 120                 125

Gly Glu Asn Gly Lys Thr Val Ile Asn Phe Asp Asn Ala Ile Ile Ala
    130                 135                 140

Ala Gly Ser Arg Pro Ile Gln Leu Pro Phe Ile Pro His Glu Asp Pro
145                 150                 155                 160

Arg Ile Trp Asp Ser Thr Asp Ala Leu Glu Leu Lys Glu Val Pro Glu
                165                 170                 175

Arg Leu Leu Val Met Gly Gly Gly Ile Ile Gly Leu Glu Met Gly Thr
            180                 185                 190

Val Tyr His Ala Leu Gly Ser Gln Ile Asp Val Val Glu Met Phe Asp
    195                 200                 205

Gln Val Ile Pro Ala Ala Asp Lys Asp Ile Val Lys Val Phe Thr Lys
210                 215                 220

Arg Ile Ser Lys Lys Phe Asn Leu Met Leu Glu Thr Lys Val Thr Ala
225                 230                 235                 240

Val Glu Ala Lys Glu Asp Gly Ile Tyr Val Thr Met Glu Gly Lys Lys
                245                 250                 255

Ala Pro Ala Glu Pro Gln Arg Tyr Asp Ala Val Leu Val Ala Ile Gly
            260                 265                 270

Arg Val Ser Asn Gly Lys Asn Leu Asp Ala Gly Lys Ala Gly Val Glu
        275                 280                 285

Val Asp Asp Arg Gly Phe Ile Arg Val Asp Lys Gln Leu Arg Thr Asn
    290                 295                 300

Val Pro His Ile Phe Ala Ile Gly Asp Ile Val Gly Gln Pro Met Leu
305                 310                 315                 320

Ala His Lys Gly Val His Glu Gly His Val Ala Ala Glu Val Ile Ala
                325                 330                 335

Gly Lys Lys His Tyr Phe Asp Pro Lys Val Ile Pro Ser Ile Ala Tyr
            340                 345                 350

Thr Glu Pro Glu Val Val Trp Val Gly Leu Thr Glu Lys Glu Ala Lys
        355                 360                 365

Glu Lys Gly Ile Ser Phe Glu Thr Ala Thr Phe Pro Trp Ala Ala Ser
    370                 375                 380

Gly Arg Ala Ile Ala Ser Asp Cys Ala Asp Gly Met Thr Lys Leu Ile
385                 390                 395                 400

Phe Asp Lys Glu Ser His Arg Val Ile Gly Gly Ala Ile Val Gly Thr
                405                 410                 415

Asn Gly Gly Glu Leu Leu Gly Glu Ile Gly Leu Ala Ile Glu Met Gly
            420                 425                 430

Cys Asp Ala Glu Asp Ile Ala Leu Thr Ile His Ala His Pro Thr Leu
        435                 440                 445

His Glu Ser Val Gly Leu Ala Ala Glu Val Phe Glu Gly Ser Ile Thr
    450                 455                 460

Asp Leu Pro Asn Pro Lys Ala Lys Lys Lys
465                 470

<210> SEQ ID NO 4
<211> LENGTH: 1425
<212> TYPE: DNA
<213> ORGANISM: Escherichia coli
<220> FEATURE:
<221> NAME/KEY: gene
<222> LOCATION: (1)..(1425)

<400> SEQUENCE: 4
atgagtactg aaatcaaaac tcaggtcgtg gtacttgggg caggccccgc aggttactcc      60
gctgccttcc gttgcgctga tttaggtctg gaaaccgtaa tcgtagaacg ttacaacacc     120
cttggcggtg tttgcctgaa cgtcggctgt atcccttcta aagcactgct gcacgtagca     180
aaagttatcg aagaagccaa agcgctggct gaacacggta tcgtcttcgg cgaaccgaaa     240
atcgatatcg acaagattcg tacctggaaa gagaaagtga tcaatcagct gaccggtggt     300
ctggctggta tggcgaaagg ccgcaaagtc aaagtggtca acggtctggg taaattcacc     360
ggggctaaca ccctggaagt tgaaggtgag aacggcaaaa ccgtgatcaa cttcgacaac     420

```
gcgatcattg cagcgggttc tcgcccgatc caactgccgt ttattccgca tgaagatccg      480
cgtatctggg actccactga cgcgctggaa ctgaaagaag taccagaacg cctgctggta      540
atgggtggcg gtatcatcgg tctggaaatg ggcaccgttt accacgcgct gggttcacag      600
attgacgtgg ttgaaatgtt cgaccaggtt atcccggcag ctgacaaaga catcgttaaa      660
gtcttcacca agcgtatcag caagaaattc aacctgatgc tggaaaccaa agttaccgcc      720
gttgaagcga agaagacgg catttatgtg acgatgaag gcaaaaaagc acccgctgaa      780
ccgcagcgtt acgacgccgt gctggtagcg attggtcgtg tgtcgaacgg taaaaacctc      840
gacgcaggca aagcaggcgt ggaagttgac gaccgtggtt catccgcgt tgacaaacag      900 ctgcgtacca acgtaccgca catctttgct atcggcgata tcgtcggtca accgatgctg      960
gcacacaaag gtgttcacga aggtcacgtt gccgctgaag ttatcgccgg taagaaacac     1020
tacttcgatc cgaaagttat cccgtccatc gcctataccg aaccagaagt tgtatgggtg     1080
ggtctgactg agaagaagc gaaagagaaa ggcatcagct atgaaaccgc caccttcccg     1140
tgggctgctt ctggtcgtgc tatcgcttcc gactgcgcag acggtatgac caagctgatt     1200
ttcgacaaag aatctcaccg tgtgatcggt ggtgcgattg tcggtactaa cggcggcgag     1260
ctgctgggtg aaatcggcct ggcaatcgaa atgggttgtg atgctgaaga catcgcactg     1320
accatccacg cgcaccccgac tctgcacgag tctgtgggcc tggcggcaga agtgttcgaa     1380
ggtagcatta ccgacctgcc gaacccgaaa gcgaagaaga agtaa                      1425

<210> SEQ ID NO 5
<211> LENGTH: 1401
<212> TYPE: DNA
<213> ORGANISM: Escherichia coli
<220> FEATURE:
<221> NAME/KEY: gene
<222> LOCATION: (1)..(1401)

<400> SEQUENCE: 5
atgccacatt cctacgatta cgatgccata gtaataggtt ccggccccgg cggcgaaggc       60
gctgcaatgg gcctggttaa gcaaggtgcg cgcgtcgcag ttatcgagcg ttatcaaaat      120
gttggcggcg gttgcaccca ctggggcacc atcccgtcga agctctccg tcacgccgtc       180 agccgcatta tagaattcaa tcaaaaccca ctatacagcg accattcccg gctgctccgc      240
tcttcttttg ccgatatcct taaccatgcc gataacgtga ttaatcaaca aacgcgcatg      300
cgtcagggat tttacgaacg taatcactgt gaaatattgc aggggaacgc tcgctttgtt      360
gatgagcata cgttggcgct ggattgcccg gacggcagcg ttgaaacact aaccgctgaa      420
aaatttatta ttgcctgcgg ctctcgtcca tatcatccaa cagatgttga tttcacccat      480
ccacgcattt acgacagcga ctcaattctt agcatgcacc acgaaccgcg ccatgtactt      540
atctatggtg ctggagtgat cggctgtgaa atgcgtcga tcttccgcgg tatggatgta      600
aaagtggatc tgatcaacac ccgcgatcgg ctgctggcat ttctcgatca agagatgtca      660
gattctctct cctatcactt ctggaacagt ggcgtagtga ttcgccacaa cgaagagtac      720
gagaagatcg aaggctgtga cgacggtgtg atcatgcatc tgaagtcggg taaaaaactg      780
aaagctgact gcctgctcta tgccaacggt cgcaccggta atactgattc gctggcgtta      840
cagaacattg gctggaaaac tgacagtcgc ggacagctga aggtcaacag catgtatcag      900
accgcacagc cgcacgttta cgcggtgggc gacgtgattg gttatccgag cctggcgtcg      960
gcggcctatg accagggggcg cattgccgcg caggcgctgg tgaaaggtga agccaccgca     1020
```

```
catctgattg aagatatccc taccggcatt tacaccatcc cggaaatcag ctctgtgggc    1080
aaaaccgaac agcagctgac cgcgatgaaa gtgccatatg aagtgggccg cgcccagttc    1140
aaacatctgg cacgtgcaca atcgtcggc atgaacgtgg gcacgctgaa aattttgttc     1200
catcgggaaa caaaagagat tctgggcatt cactgctttg cgagcgcgc tgccgaaatt     1260 attcatatcg gtcaggcgat tatggaacag aaaggtggcg gcaacactat tgagtacttc    1320
gtcaacacca cctttaacta cccgacgatg gcggaagcct atcgggtagc tgcgctaaat    1380
ggcttaaacc gcctgtttta a                                              1401
```

<210> SEQ ID NO 6
<211> LENGTH: 1992
<212> TYPE: DNA
<213> ORGANISM: Escherichia coli
<220> FEATURE:
<221> NAME/KEY: gene
<222> LOCATION: (1)..(1992)

<400> SEQUENCE: 6

```
atgtcctcac gtaaagagct tgccaatgct attcgtgcgc tgagcatgga cgcagtacag     60
aaagccaaat ccggtcaccc gggtgcccct atgggtatgg ctgacattgc cgaagtcctg    120
tggcgtgatt tcctgaaaca caacccgcag aatccgtcct gggctgaccg tgaccgcttc    180
gtgctgtcca acgccacgg ctccatgctg atctacagcc tgctgcacct caccggttac     240
gatctgccga tggaagaact gaaaaacttc cgtcagctgc actctaaaac tccgggccac    300
ccggaagtag ttataccgc tggtgtggaa accaccaccg gtccgctggg tcagggtatt     360
gccaacgcag tcggtatggc gattgcagaa aaaacgctgg cggcgcagtt taaccgtcca    420
ggtcacgaca ttgtcgacca ctacacctac gccttcatgg gcgacggctg catgatggaa    480
ggcatctccc acgaagtttg ctctctggcg gtacgctga agctgggtaa actgattgcg     540
ttctacgatg acaacggtat ctcaatcgat ggtcacgttg aaggctggtt cactgacgac    600
accgcaatgc gtttcgaagc ttacggctgg cacgttattc gcgacatcga cggtcatgac    660
gcggcatcca tcaaacgcgc agtagaagaa gcgcgcgcag tgactgacaa accgtccctg    720
ctgatgtgca aaccatcat cggtttcggt tccccgaaca agccggtac ccacgactcc      780 cacggtgcgc cgctgggcga cgctgaaatt gccctgaccc gcaacagct gggctggaaa    840 tacgcgccgt tcgaaatccc gtctgaaatc tatgctcagt gggatgcgaa agaagcaggc    900
caggcgaaag aatctgcatg gaatgagaag tttgcggctt acgcgaaagc ttatccgcag    960
gaagcggctg aatttacccg ccgtatgaaa ggcgaaatgc cgtctgactt cgacgccaaa   1020
gcgaaagagt ttatcgctaa actgcaggct aatccggcga aaatcgccag ccgtaaagcg    1080
tcgcagaatg ctatcgaagc gttcggcccg ctgttgcctg aattcctcgg cggctctgct   1140
gacctggcac cgtctaacct gaccctgtgg tctggttcta aagcaatcaa cgaagatgct   1200
gcaggtaact acatccacta cggtgttcgc gagttcggta tgaccgcgat tgctaacggt    1260 atctcccctgc acggtggttt cctgccgtac acctccacct tcctgatgtt cgtggaatac    1320
gcacgtaacg ccgtacgtat ggctgcgctg atgaaacagc gtcaggtgat ggtttacacc    1380
cacgactcca tcggtctggg cgaagatggc ccgactcacc agccggttga gcaggtcgct    1440
tctctgcgcg tgacccgaa catgtctaca tggcgtccgt gtgaccaggt tgaatccgcg     1500
gtcgcgtgga atacggcgt tgagcgtcag gacggcccga ctgcgcttat cctctcccgt     1560
cagaacctgg cgcagcagga acgaactgaa gagcaactgg caaacatcgc gcgcggtggt    1620
```

```
tatgtgctga aagactgcgc cggtcagccg gaactgattt tcatcgctac cggttcagaa    1680
gttgaactgg ctgttgctgc ctacgaaaaa ctgactgccg aaggcgtgaa agcgcgcgtg    1740
gtgtccatgc cgtctaccga cgcatttgac aagcaggatg ctgcttaccg tgaatccgta    1800
ctgccgaaag cggttactgc acgcgttgct gtagaagcgg gtattgctga ctactggtac    1860
aagtatgttg gcctgaacgg tgctatcgtc ggtatgacca ccttcggtga atctgctccg    1920
gcagagctgc tgtttgaaga gttcggcttc actgttgata cgttgttgc gaaagcaaaa    1980 gaactgctgt aa                                                       1992
```

<210> SEQ ID NO 7
<211> LENGTH: 30
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(30)

<400> SEQUENCE: 7

```
gctaggtacc tgtgacggaa gatcacttcg                                      30
```

<210> SEQ ID NO 8
<211> LENGTH: 29
<212> TYPE: DNA
<213> ORGANISM: Artificial
<220> FEATURE:
<223> OTHER INFORMATION: Primer
<220> FEATURE:
<221> NAME/KEY: primer_bind
<222> LOCATION: (1)..(29)

<400> SEQUENCE: 8

```
gctagagctc gcggctattt aacgaccct                                       29
```

<210> SEQ ID NO 9
<211> LENGTH: 29
<212> TYPE: DNA
<213> ORGANISM: Artificial
<220> FEATURE:
<223> OTHER INFORMATION: Primer
<220> FEATURE:
<221> NAME/KEY: primer_bind
<222> LOCATION: (1)..(29)

<400> SEQUENCE: 9

```
gctagagctc aagtaaatcg cgcgggttt                                       29
```

<210> SEQ ID NO 10
<211> LENGTH: 33
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(30)

<400> SEQUENCE: 10

```
gctaggatcc ttatttgtta actgttaatt gtc                                  33
```

<210> SEQ ID NO 11
<211> LENGTH: 17
<212> TYPE: DNA

```
<213> ORGANISM: Artificial
<220> FEATURE:
<223> OTHER INFORMATION: primer
<220> FEATURE:
<221> NAME/KEY: primer_bind
<222> LOCATION: (1)..(17)

<400> SEQUENCE: 11
gtaaaacgac ggccagt                                                        17

<210> SEQ ID NO 12
<211> LENGTH: 17
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(17)

<400> SEQUENCE: 12
caggaaacag ctatgac                                                        17

<210> SEQ ID NO 13
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 13
gataacggag atcgggaatg                                                     20

<210> SEQ ID NO 14
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 14
ctttggctgt cagttcacca                                                     20

<210> SEQ ID NO 15
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 15
tctggaaaaa ggcgaaacct                                                     20

<210> SEQ ID NO 16
<211> LENGTH: 21
<212> TYPE: DNA
<213> ORGANISM: Artificial
<220> FEATURE:
<223> OTHER INFORMATION: primer
<220> FEATURE:
```

<221> NAME/KEY: primer_bind
<222> LOCATION: (1)..(21)

<400> SEQUENCE: 16
tttgtgctat aaacggcgag t                                              21

<210> SEQ ID NO 17
<211> LENGTH: 22
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(22)

<400> SEQUENCE: 17
tgtgacggaa gatcacttcg ca                                             22

<210> SEQ ID NO 18
<211> LENGTH: 25
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(25)

<400> SEQUENCE: 18
ttatttgtta actgttaatt gtcct                                          25

<210> SEQ ID NO 19
<211> LENGTH: 22
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(22)

<400> SEQUENCE: 19
tgtccgagct taatgaaaag tt                                             22

<210> SEQ ID NO 20
<211> LENGTH: 22
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(22)

<400> SEQUENCE: 20
cgagtaataa cgtcctgctg ct                                             22

<210> SEQ ID NO 21
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 21
aaacgggtaa caccccagac                                          20

<210> SEQ ID NO 22
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 22
cggagtgtaa acgtcgaaca                                          20

<210> SEQ ID NO 23
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 23
cgcattatgt tcccgatgat                                          20

<210> SEQ ID NO 24
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 24
gcctttcagt tcaacggtgt                                          20

<210> SEQ ID NO 25
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 25
cggcccaatt tactgcttag                                          20

<210> SEQ ID NO 26
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 26
atccccagca acagaagtgt                                          20

```
<210> SEQ ID NO 27
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 27
atctgctgca cccgatctac                                                    20

<210> SEQ ID NO 28
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 28
gaaccggcaa caaacaaaat                                                    20

<210> SEQ ID NO 29
<211> LENGTH: 23
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(23)

<400> SEQUENCE: 29
atgcctgacg ctaaaaaaca ggg                                                23

<210> SEQ ID NO 30
<211> LENGTH: 22
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(22)

<400> SEQUENCE: 30
gattaaacgc tgttatctgc aa                                                 22

<210> SEQ ID NO 31
<211> LENGTH: 30
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(30)

<400> SEQUENCE: 31
gcatactagt gttggttatc cagaatcaaa                                         30

<210> SEQ ID NO 32
<211> LENGTH: 34
<212> TYPE: DNA
<213> ORGANISM: Artificial
```

```
<220> FEATURE:
<223> OTHER INFORMATION: primer
<220> FEATURE:
<221> NAME/KEY: primer_bind
<222> LOCATION: (1)..(34)

<400> SEQUENCE: 32
gcatggtacc agccaatatg tattgcctga atag                                      34

<210> SEQ ID NO 33
<211> LENGTH: 21
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(21)

<400> SEQUENCE: 33
acggttaaca cccccaaaaa g                                                    21

<210> SEQ ID NO 34
<211> LENGTH: 25
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(25)

<400> SEQUENCE: 34
gacaaggctc atagatttac gtatc                                                25

<210> SEQ ID NO 35
<211> LENGTH: 72
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(72)

<400> SEQUENCE: 35
cgccatataa accaagattt aaccttttga gaacattttc cacacctaag tgtgacggaa          60
gatcacttcg ca                                                              72

<210> SEQ ID NO 36
<211> LENGTH: 75
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(75)

<400> SEQUENCE: 36
ataccataag cctcgagttc ttgcggggtc aaaccattgt taacgcgcat ttatttgtta          60
actgttaatt gtcct                                                           75

<210> SEQ ID NO 37
<211> LENGTH: 18
<212> TYPE: DNA
<213> ORGANISM: Artificial
```

```
<220> FEATURE:
<223> OTHER INFORMATION: primer
<220> FEATURE:
<221> NAME/KEY: primer_bind
<222> LOCATION: (1)..(18)

<400> SEQUENCE: 37
acgccataaa caatccaa                                                    18

<210> SEQ ID NO 38
<211> LENGTH: 18
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(18)

<400> SEQUENCE: 38
cgcatttcac tgctcctt                                                    18

<210> SEQ ID NO 39
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 39
cgggacaacg ttcaaaacat                                                  20

<210> SEQ ID NO 40
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 40
attgcccatc ttcttgttgg                                                  20

<210> SEQ ID NO 41
<211> LENGTH: 21
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(21)

<400> SEQUENCE: 41
aactaccgca gttcagaacc a                                                21

<210> SEQ ID NO 42
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
```

<222> LOCATION: (1)..(20)

<400> SEQUENCE: 42
tctgaacacc ggtaacacca                                                    20

<210> SEQ ID NO 43
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 43
attctggcag agacggaaga                                                    20

<210> SEQ ID NO 44
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 44
tcgaaatcgg ccataaagac                                                    20

<210> SEQ ID NO 45
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 45
ttaatccagc gttggattca                                                    20

<210> SEQ ID NO 46
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 46
atgactgaac aggcaacaac                                                    20

<210> SEQ ID NO 47
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 47
tttcctgcga tgggaatagt                                          20

<210> SEQ ID NO 48
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 48
aagcctggct ggacggtaac                                          20

<210> SEQ ID NO 49
<211> LENGTH: 25
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(25)

<400> SEQUENCE: 49
atgctgacat tcattgagct cctta                                    25

<210> SEQ ID NO 50
<211> LENGTH: 25
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(25)

<400> SEQUENCE: 50
aatttttcct gtctccaggc cccaa                                    25

<210> SEQ ID NO 51
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 51
cagctcatca accaggtcaa                                          20

<210> SEQ ID NO 52
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 52
aaaagccgtc acgttattgg                                          20

<210> SEQ ID NO 53

```
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 53
agcgttatct cgcggaccgt                                                  20

<210> SEQ ID NO 54
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 54
aagtgcgagt cgtcagttcc                                                  20

<210> SEQ ID NO 55
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 55
cagctcatca accaggtcaa                                                  20

<210> SEQ ID NO 56
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 56
aaaagccgtc acgttattgg                                                  20

<210> SEQ ID NO 57
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 57
agcgttatct cgcggaccgt                                                  20

<210> SEQ ID NO 58
<211> LENGTH: 20
<212> TYPE: DNA
<213> ORGANISM: Artificial
<220> FEATURE:
```

```
<223> OTHER INFORMATION: primer
<220> FEATURE:
<221> NAME/KEY: primer_bind
<222> LOCATION: (1)..(20)

<400> SEQUENCE: 58
aagtgcgagt cgtcagttcc                                                 20

<210> SEQ ID NO 59
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 59
cagctcatca accaggtcaa                                                 20

<210> SEQ ID NO 60
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 60
aaaagccgtc acgttattgg                                                 20

<210> SEQ ID NO 61
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 61
agcgttatct cgcggaccgt                                                 20

<210> SEQ ID NO 62
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 62
aagtgcgagt cgtcagttcc                                                 20

<210> SEQ ID NO 63
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)
```

```
<400> SEQUENCE: 63
tccgggcagt agtatttgc                                           20

<210> SEQ ID NO 64
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 64
atggctggat caaagtcagc                                          20

<210> SEQ ID NO 65
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 65
cctggcgaaa ctgtttatcg                                          20

<210> SEQ ID NO 66
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 66
ttgttaacgc gcatttcact                                          20

<210> SEQ ID NO 67
<211> LENGTH: 18
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(18)

<400> SEQUENCE: 67
agcgtttcgt taccactg                                            18

<210> SEQ ID NO 68
<211> LENGTH: 18
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(18)

<400> SEQUENCE: 68
tacggcgatg ttgtccctt                                           18
```

```
<210> SEQ ID NO 69
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 69
attgacgata atttctggca                                               20

<210> SEQ ID NO 70
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 70
acgctgtttt tttgttttg                                                20

<210> SEQ ID NO 71
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 71
ttagcgtcat aatgccaatt                                               20

<210> SEQ ID NO 72
<211> LENGTH: 19
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(19)

<400> SEQUENCE: 72
cgaccacctg ttgttcctg                                                19

<210> SEQ ID NO 73
<211> LENGTH: 18
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(18)

<400> SEQUENCE: 73
atcggtgcgt cgtatcgt                                                 18

<210> SEQ ID NO 74
<211> LENGTH: 18
```

```
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(18)

<400> SEQUENCE: 74
aacctggatt ttccctgg                                                  18

<210> SEQ ID NO 75
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 75
gcgcatctta tccgacctac                                                20

<210> SEQ ID NO 76
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 76
gcctggactt ctgtggaatg                                                20

<210> SEQ ID NO 77
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 77
gtcactattg ccgggattgc                                                20

<210> SEQ ID NO 78
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 78
caatgcggaa tattgttcgt                                                20

<210> SEQ ID NO 79
<211> LENGTH: 70
<212> TYPE: DNA
<213> ORGANISM: Artificial
<220> FEATURE:
<223> OTHER INFORMATION: primer
```

```
<220> FEATURE:
<221> NAME/KEY: primer_bind
<222> LOCATION: (1)..(70)

<400> SEQUENCE: 79
aaatgcgccg tttgcaggtg aatcgacgct cagtctcagt ataaggaatg tgacggaaga    60
tcacttcgca                                                          70

<210> SEQ ID NO 80
<211> LENGTH: 75
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(75)

<400> SEQUENCE: 80
tccatgctca gcgcacgaat agcattggca agctctttac gtgaggacat ttatttgtta   60
actgttaatt gtcct                                                    75

<210> SEQ ID NO 81
<211> LENGTH: 68
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(68)

<400> SEQUENCE: 81
aaatgcgccg tttgcaggtg aatcgacgct cagtctcagt ataaggaatt atctctggcg   60
gtgttgac                                                            68

<210> SEQ ID NO 82
<211> LENGTH: 65
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(65)

<400> SEQUENCE: 82
tccatgctca gcgcacgaat agcattggca agctctttac gtgaggacat agctgtttcc   60
tggtt                                                               65

<210> SEQ ID NO 83
<211> LENGTH: 18
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(18)

<400> SEQUENCE: 83
tcaggaaatc acgccaca                                                 18

<210> SEQ ID NO 84
<211> LENGTH: 20
```

```
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 84
atccgtcatc atatccatca                                                    20

<210> SEQ ID NO 85
<211> LENGTH: 72
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(72)

<400> SEQUENCE: 85
ttacccgcga taaaatgtta ccattctgtt gcttttatgt ataagaacag tgtgacggaa        60
gatcacttcg ca                                                            72

<210> SEQ ID NO 86
<211> LENGTH: 75
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(75)

<400> SEQUENCE: 86
ccggggccgg aacctattac tatggcatcg taatcgtagg aatgtggcat ttatttgtta        60
actgttaatt gtcct                                                         75

<210> SEQ ID NO 87
<211> LENGTH: 70
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(70)

<400> SEQUENCE: 87
ttacccgcga taaaatgtta ccattctgtt gcttttatgt ataagaacag ttatctctgg        60
cggtgttgac                                                               70

<210> SEQ ID NO 88
<211> LENGTH: 65
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(65)

<400> SEQUENCE: 88
ccggggccgg aacctattac tatggcatcg taatcgtagg aatgtggcat agctgtttcc        60
tggtt                                                                    65
```

-continued

```
<210> SEQ ID NO 89
<211> LENGTH: 19
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(19)

<400> SEQUENCE: 89
ttttcagcgg ttagtgttt                                                   19

<210> SEQ ID NO 90
<211> LENGTH: 18
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(18)

<400> SEQUENCE: 90
aactcaggct ggcgaagc                                                    18

<210> SEQ ID NO 91
<211> LENGTH: 82
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(82)

<400> SEQUENCE: 91
agacttccgt cagatcaaga ataatggtat gcggcagcga atgcacccgc tttatgcatg      60
tgtgacggaa gatcacttcg ca                                               82

<210> SEQ ID NO 92
<211> LENGTH: 83
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(83)

<400> SEQUENCE: 92
cctggagcca gtcgcgagtt tcgatcggat ccacgtcatt tgggaaacgt tctgacattt      60
atttgttaac tgttaattgt cct                                              83

<210> SEQ ID NO 93
<211> LENGTH: 80
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(80)

<400> SEQUENCE: 93
agacttccgt cagatcaaga ataatggtat gcggcagcga atgcacccgc tttatgcatg      60
```

```
ttatctctgg cggtgttgac                                                       80

<210> SEQ ID NO 94
<211> LENGTH: 70
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(70)

<400> SEQUENCE: 94
cctggagcca gtcgcgagtt tcgatcggat ccacgtcatt tgggaaacgt tctgacatag         60
ctgtttcctg                                                                 70

<210> SEQ ID NO 95
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 95
ttatctctgg cggtgttgac                                                       20

<210> SEQ ID NO 96
<211> LENGTH: 24
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(24)

<400> SEQUENCE: 96
acggaagaag tggttaaagc acac                                                  24

<210> SEQ ID NO 97
<211> LENGTH: 30
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(30)

<400> SEQUENCE: 97
gcatttaatt aagtgtaggc tggagctgct                                            30

<210> SEQ ID NO 98
<211> LENGTH: 25
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(25)

<400> SEQUENCE: 98
gcatgaattc cagaatcgaa atctc                                                 25
```

```
<210> SEQ ID NO 99
<211> LENGTH: 19
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(19)

<400> SEQUENCE: 99
ccgtgatatt gctgaagag                                                  19

<210> SEQ ID NO 100
<211> LENGTH: 20
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(20)

<400> SEQUENCE: 100
ctgcgttctg atttaatctg                                                 20

<210> SEQ ID NO 101
<211> LENGTH: 22
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(22)

<400> SEQUENCE: 101
agcagtgctt tagaagggat ac                                              22

<210> SEQ ID NO 102
<211> LENGTH: 87
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(87)

<400> SEQUENCE: 102
tcatcatgcg ctacgctcta tggctccctg acgttttttt agccacgtat caattatagg     60
tacttccgtg taggctggag ctgcttc                                         87

<210> SEQ ID NO 103
<211> LENGTH: 83
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(83)

<400> SEQUENCE: 103
gttaagcaag ataatcagaa aggattaatg cagattaaga gaataaaaaa ccggaaatag     60
tgaaaaaggc catccgtcag gat                                             83
```

<210> SEQ ID NO 104
<211> LENGTH: 89
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(89)

<400> SEQUENCE: 104
tcatcatgcg ctacgctcta tggctccctg acgttttttt agccacgtat caattatagg    60
tacttcctgt gacggaagat cacttcgca                                      89

<210> SEQ ID NO 105
<211> LENGTH: 99
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(99)

<400> SEQUENCE: 105
cggaaggcag cggagtaacc tgcggggcct gccccaagta ccacgacctg agttttgatt    60
tcagtactca tcatttattt gttaactgtt aattgtcct                           99

<210> SEQ ID NO 106
<211> LENGTH: 87
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(87)

<400> SEQUENCE: 106
tcatcatgcg ctacgctcta tggctccctg acgttttttt agccacgtat caattatagg    60
tacttcctta tctctggcgg tgttgac                                        87

<210> SEQ ID NO 107
<211> LENGTH: 89
<212> TYPE: DNA
<213> ORGANISM: Artificial
<220> FEATURE:
<223> OTHER INFORMATION: primer
<220> FEATURE:
<221> NAME/KEY: primer_bind
<222> LOCATION: (1)..(89)

<400> SEQUENCE: 107
cggaaggcag cggagtaacc tgcggggcct gccccaagta ccacgacctg agttttgatt    60
tcagtactca tcatagctgt ttcctggtt                                      89

<210> SEQ ID NO 108
<211> LENGTH: 378
<212> TYPE: DNA
<213> ORGANISM: Artificial
<220> FEATURE:
<223> OTHER INFORMATION: promoter
<220> FEATURE:
<221> NAME/KEY: promoter
<222> LOCATION: (1)..(378)

<400> SEQUENCE: 108

```
gttggttatc cagaatcaaa aggtgggtta attatcgcat ccgggcagta gtattttgct      60
tttttcagaa aataatcaaa aaaagttagc gtggtgaatc gatactttac cggttgaatt    120
tgcatcaatt tcattcagga atgcgattcc actcacaata ttcccgccat ataaaccaag    180
atttaacctt ttgagaacat tttccacacc taaaatgcta tttctgcgat aatagcaacc    240
gtttcgtgac aggaatcacg gagttttttg tcaaatatga atttctccag atacgtaaat    300
ctatgagcct tgtcacggtt aacaccccca aaaagacttt actattcagg caatacatat    360
tggctaagga gcagtgaa                                                  378
```

<210> SEQ ID NO 109
<211> LENGTH: 88
<212> TYPE: DNA
<213> ORGANISM: Artificial
<220> FEATURE:
<223> OTHER INFORMATION: promoter
<220> FEATURE:
<221> NAME/KEY: promoter
<222> LOCATION: (1)..(88)

<400> SEQUENCE: 109

```
ttatctctgg cggtgttgac aagagataac aacgttgata taattgagcc actggctcgt     60
aatttattgt ttaaaccagg aaacagct                                        88
```

<210> SEQ ID NO 110
<211> LENGTH: 88
<212> TYPE: DNA
<213> ORGANISM: Artificial
<220> FEATURE:
<223> OTHER INFORMATION: promoter
<220> FEATURE:
<221> NAME/KEY: promoter
<222> LOCATION: (1)..(88)

<400> SEQUENCE: 110

```
ttatctctgg cggtgttgac aagagataac aacgttgata taattgagcc cgtattgtta     60
gcatgtacgt ttaaaccagg aaacagct                                        88
```

<210> SEQ ID NO 111
<211> LENGTH: 3749
<212> TYPE: DNA
<213> ORGANISM: Artificial
<220> FEATURE:
<223> OTHER INFORMATION: Plasmid

<400> SEQUENCE: 111

```
gtttgacagc ttatcatcga ctgcacggtg caccaatgct tctggcgtca ggcagccatc     60
ggaagctgtg gtatggctgt gcaggtcgta atcactgca taattcgtgt cgctcaaggc    120
gcactcccgt tctggataat gttttttgcg ccgacatcat aacggttctg gcaaatattc    180
tgaaatgagc tgttgacaat taatcatccg gctcgtataa tgtgtggaat tgtgagcgga    240
taacaatttc acacaggaaa cagaccatgg aattcgagct cggtaccgg ggatcctcta     300 gagtcgacct gcaggcatgc aagcttggct gttttggcgg atgagagaag attttcagcc    360
tgatacagat taaatcagaa cgcagaagcg gtctgataaa acagaatttg cctggcggca    420
gtagcgcggt ggtcccacct gacccccatgc cgaactcaga agtgaaacgc cgtagcgccg    480
atggtagtgt ggggtctccc catgcgagag tagggaactg ccaggcatca aataaaacga    540
```

```
aaggctcagt cgaaagactg ggcctttcgt tttatctgtt gtttgtcggt gaacgctctc      600
ctgagtagga caaatccgcc gggagcggat ttgaacgttg cgaagcaacg gcccggaggg      660
tggcgggcag gacgcccgcc ataaactgcc aggcatcaaa ttaagcagaa ggccatcctg      720
acggatggcc ttttttgcgtt tctttaatta aattcaaata tgtatccgct catgagacaa     780
taaccctgat aaatgcttca ataatattga aaaggaaga gtatgagtat tcaacatttc       840
cgtgtcgccc ttattccctt ttttgcggca ttttgccttc ctgttttgc tcacccagaa       900
acgctggtga agtaaaaga tgctgaagat cagttgggtg cacgagtggg ttacatcgaa       960
ctggatctca acagcggtaa gatccttgag agtttttcgcc ccgaagaacg ttttccaatg    1020
atgagcactt ttaaagttct gctatgtggc gcggtattat cccgtgttga cgccgggcaa    1080
gagcaactcg gtcgccgcat acactattct cagaatgact tggttgagta ctcaccagtc    1140
acagaaaagc atcttacgga tggcatgaca gtaagagaat tatgcagtgc tgccataacc    1200
atgagtgata acactgcggc caacttactt ctgacaacga tcggaggacc gaaggagcta    1260
accgcttttt tgcacaacat gggggatcat gtaactcgcc ttgatcgttg ggaaccggag    1320
ctgaatgaag ccataccaaa cgacgagcgt gacaccacga tgcctacagc aatggcaaca    1380
acgttgcgca aactattaac tggcgaacta cttactctag cttcccggca acaattaata    1440
gactggatgg aggcggataa agttgcagga ccacttctgc gctcggccct tccggctggc    1500
tggtttattg ctgataaatc tggagccggt gagcgtgggt ctcgcggtat cattgcagca    1560
ctggggccag atggtaagcc ctcccgtatc gtagttatct acacgacggg gagtcaggca    1620
actatggatg aacgaaatag acagatcgct gagataggtg cctcactgat taagcattgg    1680
taactgtcag accaagttta ctcatatata ctttagattg atttaaaact catttttaa     1740
tttaaaagga tctaggtgaa gatcctttt gataatctca tgaccaaaat cccttaacgt    1800
gagttttcgt tccactgagc gtcagacccc gtagaaaaga tcaaaggatc ttcttgagat    1860
cctttttttc tgcgcgtaat ctgctgcttg caaacaaaaa aaccaccgct accagcggtg    1920
gtttgtttgc cggatcaaga gctaccaact cttttttccga aggtaactgg cttcagcaga    1980
gcgcagatac caaatactgt ccttctagtg tagccgtagt taggccacca cttcaagaac    2040
tctgtagcac cgcctacata cctcgctctg ctaatcctgt taccagtggc tgctgccagt    2100
ggcgataagt cgtgtcttac cgggttggac tcaagacgat agttaccgga taaggcgcag    2160
cggtcgggct gaacgggggg ttcgtgcaca cagcccagct tggagcgaac gacctacacc    2220
gaactgagat acctacagcg tgagctatga gaaagcgcca cgcttcccga agggagaaag    2280
gcggacaggt atccggtaag cggcagggtc ggaacaggag agcgcacgag ggagcttcca    2340
gggggaaacg cctggtatct ttatagtcct gtcgggtttc gccacctctg acttgagcgt    2400
cgatttttgt gatgctcgtc aggggggcgg agcctatgga aaaacgccag caacgcggcc    2460
tttttacggt tcctggcctt ttgctggcct tttgctcaca tgttctttcc tgcgttaatt    2520
aactagtcat atgggcatgc atttacgttg acaccatcga atggtgcaaa acctttcgcg    2580
gtatggcatg atagcgcccg gaagagagtc aattcagggt ggtgaatgtg aaaccagtaa    2640
cgttatacga tgtcgcagag tatgccgtg tctcttatca gaccgtttcc cgcgtggtga    2700
accaggccag ccacgtttct gcgaaaacgc gggaaaaagt ggaagcggcg atggcggagc    2760
tgaattacat tcccaaccgc gtggcacaac aactggcggg caaacagtcg ttgctgattg    2820
gcgttgccac ctccagtctg gccctgcacg cgccgtcgca aattgtcgcg gcgattaaat    2880
ctcgcgccga tcaactgggt gccagcgtgg tggtgtcgat ggtagaacga agcggcgtcg    2940
```

-continued

```
aagcctgtaa agcggcggtg cacaatcttc tcgcgcaacg cgtcagtggg ctgatcatta      3000
actatccgct ggatgaccag gatgccattg ctgtggaagc tgcctgcact aatgttccgg      3060
cgttatttct tgatgtctct gaccagacac ccatcaacag tattattttc tcccatgaag      3120
acggtacgcg actgggcgtg gagcatctgg tcgcattggg tcaccagcaa atcgcgctgt      3180
tagcgggccc attaagttct gtctcggcgc gtctgcgtct ggctggctgg cataaatatc      3240
tcactcgcaa tcaaattcag ccgatagcgg aacgggaagg cgactggagt gccatgtccg      3300
gttttcaaca aaccatgcaa atgctgaatg agggcatcgt tcccactgcg atgctggttg      3360
ccaacgatca gatggcgctg ggcgcaatgc gcgccattac cgagtccggg ctgcgcgttg      3420
gtgcggatat ctcggtagtg ggatacgacg ataccgaaga cagctcatgt tatatcccgc      3480
cgttaaccac catcaaacag gattttcgcc tgctggggca aaccagcgtg gaccgcttgc      3540
tgcaactctc tcagggccag gcggtgaagg gcaatcagct gttgcccgtc tcactggtga      3600
aaagaaaaac caccctggcg cccaatacgc aaaccgcctc tccccgcgcg ttggccgatt      3660
cattaatgca gctggcacga caggtttccc gactggaaag cgggcagtga gcgcaacgca      3720
attaatgtga gttagcgcga attgatctg                                        3749

<210> SEQ ID NO 112
<211> LENGTH: 75
<212> TYPE: DNA
<213> ORGANISM: Artificial
<220> FEATURE:
<223> OTHER INFORMATION: primers

<400> SEQUENCE: 112
atcagttttg ccgcactttg cgcgcttttc ccgtaatcgc acgggtggat aagtgtgacg      60
gaagatcact tcgca                                                      75

<210> SEQ ID NO 113
<211> LENGTH: 79
<212> TYPE: DNA
<213> ORGANISM: Artificial
<220> FEATURE:
<223> OTHER INFORMATION: primers

<400> SEQUENCE: 113
ccagggtata cttgtaattt tcttacggtg cactgtactg cttttacgag cttgttattt      60
gttaactgtt aattgtcct                                                  79

<210> SEQ ID NO 114
<211> LENGTH: 73
<212> TYPE: DNA
<213> ORGANISM: Artificial
<220> FEATURE:
<223> OTHER INFORMATION: primers

<400> SEQUENCE: 114
atcagttttg ccgcactttg cgcgcttttc ccgtaatcgc acgggtggat aagttatctc      60
tggcggtgtt gac                                                        73

<210> SEQ ID NO 115
<211> LENGTH: 78
<212> TYPE: DNA
<213> ORGANISM: Artificial
<220> FEATURE:
<223> OTHER INFORMATION: primers
<220> FEATURE:
```

<221> NAME/KEY: misc_feature
<222> LOCATION: (51)..(56)
<223> OTHER INFORMATION: n is a, c, g, or t

<400> SEQUENCE: 115
gcgccgaaaa tgaccaggtc acaggcctgg gctgtttgcg ttaccgccat nnnnnnyctc    60
ctggtttaaa cgtacatg                                                  78

<210> SEQ ID NO 116
<211> LENGTH: 20
<212> TYPE: DNA
<213> ORGANISM: Artificial
<220> FEATURE:
<223> OTHER INFORMATION: primers

<400> SEQUENCE: 116
catggcaaag tagttaatgg                                                20

<210> SEQ ID NO 117
<211> LENGTH: 20
<212> TYPE: DNA
<213> ORGANISM: Artificial
<220> FEATURE:
<223> OTHER INFORMATION: primers

<400> SEQUENCE: 117
gactcacggg taatgacgat                                                20

<210> SEQ ID NO 118
<211> LENGTH: 68
<212> TYPE: DNA
<213> ORGANISM: Artificial
<220> FEATURE:
<223> OTHER INFORMATION: primers

<400> SEQUENCE: 118
ttcagcattc accgccaaaa gcgactaatt ttagctgtta cagtcagttg gcgttggccg    60
attcatta                                                             68

<210> SEQ ID NO 119
<211> LENGTH: 70
<212> TYPE: DNA
<213> ORGANISM: Artificial
<220> FEATURE:
<223> OTHER INFORMATION: primers

<400> SEQUENCE: 119
acgtgaattt gctggctctc agggctggcg atataaactg tttgcttcat ggagaaaata    60
ccgcatcagg                                                           70

<210> SEQ ID NO 120
<211> LENGTH: 70
<212> TYPE: DNA
<213> ORGANISM: Artificial
<220> FEATURE:
<223> OTHER INFORMATION: primers

<400> SEQUENCE: 120
ttcagcattc accgccaaaa gcgactaatt ttagctgtta cagtcagttg ttatctctgg    60
cggtgttgac                                                           70

<210> SEQ ID NO 121
<211> LENGTH: 78

```
<212> TYPE: DNA
<213> ORGANISM: Artificial
<220> FEATURE:
<223> OTHER INFORMATION: primers
<220> FEATURE:
<221> NAME/KEY: misc_feature
<222> LOCATION: (51)..(56)
<223> OTHER INFORMATION: n is a, c, g, or t

<400> SEQUENCE: 121
acgtgaattt gctggctctc agggctggcg atataaactg tttgcttcat nnnnnnyctc      60
ctggtttaaa cgtacatg                                                   78

<210> SEQ ID NO 122
<211> LENGTH: 20
<212> TYPE: DNA
<213> ORGANISM: Artificial
<220> FEATURE:
<223> OTHER INFORMATION: primers

<400> SEQUENCE: 122
gtgatggcga cctgtgacga                                                 20

<210> SEQ ID NO 123
<211> LENGTH: 20
<212> TYPE: DNA
<213> ORGANISM: Artificial
<220> FEATURE:
<223> OTHER INFORMATION: primers

<400> SEQUENCE: 123
gggcgaacac caacatagag                                                 20

<210> SEQ ID NO 124
<211> LENGTH: 68
<212> TYPE: DNA
<213> ORGANISM: Artificial
<220> FEATURE:
<223> OTHER INFORMATION: primers

<400> SEQUENCE: 124
cttactaatt taatgaatag aactcaattg tatgtccatt tgattcagtc gcgttggccg      60
attcatta                                                              68

<210> SEQ ID NO 125
<211> LENGTH: 70
<212> TYPE: DNA
<213> ORGANISM: Artificial
<220> FEATURE:
<223> OTHER INFORMATION: primers

<400> SEQUENCE: 125
ttgcgcccca tcactgccat accgactacg ccgatctgtt gctttgacat ggagaaaata      60
ccgcatcagg                                                            70

<210> SEQ ID NO 126
<211> LENGTH: 70
<212> TYPE: DNA
<213> ORGANISM: Artificial
<220> FEATURE:
<223> OTHER INFORMATION: primers

<400> SEQUENCE: 126
cttactaatt taatgaatag aactcaattg tatgtccatt tgattcagtc ttatctctgg      60
```
cggtgttgac                                                            70

<210> SEQ ID NO 127
<211> LENGTH: 78
<212> TYPE: DNA
<213> ORGANISM: Artificial
<220> FEATURE:
<223> OTHER INFORMATION: primers
<220> FEATURE:
<221> NAME/KEY: misc_feature
<222> LOCATION: (51)..(56)
<223> OTHER INFORMATION: n is a, c, g, or t

<400> SEQUENCE: 127
ttgcgtccca tcactgccat accgactacg ccgatctgtt gcttggacat nnnnnnyctc     60
ctggtttaaa cgtacatg                                                   78

<210> SEQ ID NO 128
<211> LENGTH: 20
<212> TYPE: DNA
<213> ORGANISM: Artificial
<220> FEATURE:
<223> OTHER INFORMATION: primers

<400> SEQUENCE: 128
ggtccttgct ataagagtga                                                 20

<210> SEQ ID NO 129
<211> LENGTH: 20
<212> TYPE: DNA
<213> ORGANISM: Artificial
<220> FEATURE:
<223> OTHER INFORMATION: primers

<400> SEQUENCE: 129
acggttacga cggatggtgt                                                 20

<210> SEQ ID NO 130
<211> LENGTH: 70
<212> TYPE: DNA
<213> ORGANISM: Artificial
<220> FEATURE:
<223> OTHER INFORMATION: primers

<400> SEQUENCE: 130
aaatgcgccg tttgcaggtg aatcgacgct cagtctcagt ataaggaatg tgacggaaga     60
tcacttcgca                                                            70

<210> SEQ ID NO 131
<211> LENGTH: 75
<212> TYPE: DNA
<213> ORGANISM: Artificial
<220> FEATURE:
<223> OTHER INFORMATION: primers

<400> SEQUENCE: 131
tccatgctca gcgcacgaat agcattggca agctctttac gtgaggacat ttatttgtta     60
actgttaatt gtcct                                                      75

<210> SEQ ID NO 132
<211> LENGTH: 68
<212> TYPE: DNA
<213> ORGANISM: Artificial
<220> FEATURE:
<223> OTHER INFORMATION: primers

<400> SEQUENCE: 132
aaatgcgccg tttgcaggtg aatcgacgct cagtctcagt ataaggaatt atctctggcg    60
gtgttgac                                                             68

<210> SEQ ID NO 133
<211> LENGTH: 78
<212> TYPE: DNA
<213> ORGANISM: Artificial
<220> FEATURE:
<223> OTHER INFORMATION: primers
<220> FEATURE:
<221> NAME/KEY: misc_feature
<222> LOCATION: (51)..(56)
<223> OTHER INFORMATION: n is a, c, g, or t

<400> SEQUENCE: 133
tccatgctca gcgcacgaat agcattggca agctctttac gtgaggacat nnnnnnyctc    60
ctggtttaaa cgtacatg                                                  78

<210> SEQ ID NO 134
<211> LENGTH: 18
<212> TYPE: DNA
<213> ORGANISM: Artificial
<220> FEATURE:
<223> OTHER INFORMATION: primers

<400> SEQUENCE: 134
tcaggaaatc acgccaca                                                  18

<210> SEQ ID NO 135
<211> LENGTH: 20
<212> TYPE: DNA
<213> ORGANISM: Artificial
<220> FEATURE:
<223> OTHER INFORMATION: primers

<400> SEQUENCE: 135
atccgtcatc atatccatca                                                20

<210> SEQ ID NO 136
<211> LENGTH: 76
<212> TYPE: DNA
<213> ORGANISM: Artificial
<220> FEATURE:
<223> OTHER INFORMATION: primers

<400> SEQUENCE: 136
agtctcgcct ggcgataacc gtcttgtcgg cggttgcgct gacgttgcgt cgtgtgtgac    60
ggaagatcac ttcgca                                                    76

<210> SEQ ID NO 137
<211> LENGTH: 78
<212> TYPE: DNA
<213> ORGANISM: Artificial
<220> FEATURE:
<223> OTHER INFORMATION: primers

<400> SEQUENCE: 137
tcatgatagt atttctcttt aaacagcttg ttaggggat gtaaccggtc tgcttatttg     60
ttaactgtta attgtcct                                                  78

<210> SEQ ID NO 138

<211> LENGTH: 74
<212> TYPE: DNA
<213> ORGANISM: Artificial
<220> FEATURE:
<223> OTHER INFORMATION: primers

<400> SEQUENCE: 138
agtctcgcct ggcgataacc gtcttgtcgg cggttgcgct gacgttgcgt cgtgttatct    60
ctggcggtgt tgac                                                     74

<210> SEQ ID NO 139
<211> LENGTH: 78
<212> TYPE: DNA
<213> ORGANISM: Artificial
<220> FEATURE:
<223> OTHER INFORMATION: primers
<220> FEATURE:
<221> NAME/KEY: misc_feature
<222> LOCATION: (51)..(56)
<223> OTHER INFORMATION: n is a, c, g, or t

<400> SEQUENCE: 139
tcggccacta cggtggtgta ctgacgaagg gaggtcaatt tgtccgtcat nnnnnnyctc    60
ctggtttaaa cgtacatg                                                 78

<210> SEQ ID NO 140
<211> LENGTH: 20
<212> TYPE: DNA
<213> ORGANISM: Artificial
<220> FEATURE:
<223> OTHER INFORMATION: primers

<400> SEQUENCE: 140
ccgaagagca ggtaaatcat                                               20

<210> SEQ ID NO 141
<211> LENGTH: 20
<212> TYPE: DNA
<213> ORGANISM: Artificial
<220> FEATURE:
<223> OTHER INFORMATION: primers

<400> SEQUENCE: 141
taccagcatc gttgtagagt                                               20

<210> SEQ ID NO 142
<211> LENGTH: 189
<212> TYPE: DNA
<213> ORGANISM: Artificial
<220> FEATURE:
<223> OTHER INFORMATION: promoter

<400> SEQUENCE: 142
gaaaacgatg atttttttat cagttttgcc gcactttgcg cgcttttccc ttatctctgg    60
cggtgttgac aagagataac aacgttgata taattgagcc cgtattgtta gcatgtacgt   120
ttaaaccagg agagacagaa tggcggtaac gcaaacagcc caggcctgtg acctggtcat   180
tttcggcgc                                                          189

<210> SEQ ID NO 143
<211> LENGTH: 189
<212> TYPE: DNA
<213> ORGANISM: Artificial
<220> FEATURE:
<223> OTHER INFORMATION: promoter

```
<400> SEQUENCE: 143
gaaaacgatg attttttat  cagttttgcc gcactttgcg cgcttttccc ttatctctgg    60
cggtgttgac aagagataac aacgttgata taattgagcc cgtattgtta gcatgtacgt   120
ttaaaccagg agagagctaa tggcggtaac gcaaacagcc caggcctgtg acctggtcat   180
tttcggcgc                                                           189

<210> SEQ ID NO 144
<211> LENGTH: 189
<212> TYPE: DNA
<213> ORGANISM: Artificial
<220> FEATURE:
<223> OTHER INFORMATION: promoter

<400> SEQUENCE: 144
gaaaacgatg attttttat  cagttttgcc gcactttgcg cgcttttccc ttatctctgg    60
cggtgttgac aagagataac aacgttgata taattgagcc cgtattgtta gcatgtacgt   120
ttaaaccagg agaagtaaaa tggcggtaac gcaaacagcc caggcctgtg acctggtcat   180
tttcggcgc                                                           189

<210> SEQ ID NO 145
<211> LENGTH: 189
<212> TYPE: DNA
<213> ORGANISM: Artificial
<220> FEATURE:
<223> OTHER INFORMATION: promoter

<400> SEQUENCE: 145
gaaaacgatg attttttat  cagttttgcc gcactttgcg cgcttttccc ttatctctgg    60
cggtgttgac aagagataac aacgttgata taattgagcc cgtattgtta gcatgtacgt   120
ttaaaccagg agatgtatca tggcggtaac gcaaacagcc caggcctgtg acctggtcat   180
tttcggcgc                                                           189

<210> SEQ ID NO 146
<211> LENGTH: 189
<212> TYPE: DNA
<213> ORGANISM: Artificial
<220> FEATURE:
<223> OTHER INFORMATION: promoter

<400> SEQUENCE: 146
ttcagcattc accgccaaaa gcgactaatt ttagctgtta cagtcagttg ttatctctgg    60
cggtgttgac aagagataac aacgttgata taattgagcc cgtattgtta gcatgtacgt   120
ttaaaccagg aggcggaaca tgaagcaaac agtttatatc gccagccctg agagccagca   180
aattcacgt                                                           189

<210> SEQ ID NO 147
<211> LENGTH: 189
<212> TYPE: DNA
<213> ORGANISM: Artificial
<220> FEATURE:
<223> OTHER INFORMATION: promoter

<400> SEQUENCE: 147
ttcagcattc accgccaaaa gcgactaatt ttagctgtta cagtcagttg ttatctctgg    60
cggtgttgac aagagataac aacgttgata taattgagcc cgtattgtta gcatgtacgt   120
```

```
ttaaaccagg aggcaccaaa tgaagcaaac agtttatatc gccagccctg agagccagca    180
aattcacgt                                                            189

<210> SEQ ID NO 148
<211> LENGTH: 189
<212> TYPE: DNA
<213> ORGANISM: Artificial
<220> FEATURE:
<223> OTHER INFORMATION: promoter

<400> SEQUENCE: 148
ttcagcattc accgccaaaa gcgactaatt ttagctgtta cagtcagttg ttatctctgg     60
cggtgttgac aagagataac aacgttgata taattgagcc cgtattgtta gcatgtacgt   120
ttaaaccagg agacgcccaa tgaagcaaac agtttatatc gccagccctg agagccagca   180
aattcacgt                                                            189

<210> SEQ ID NO 149
<211> LENGTH: 189
<212> TYPE: DNA
<213> ORGANISM: Artificial
<220> FEATURE:
<223> OTHER INFORMATION: promoter

<400> SEQUENCE: 149
ttcagcattc accgccaaaa gcgactaatt ttagctgtta cagtcagttg ttatctctgg     60
cggtgttgac aagagataac aacgttgata taattgagcc cgtattgtta gcatgtacgt   120
ttaaaccagg agaggagcta tgaagcaaac agtttatatc gccagccctg agagccagca   180
aattcacgt                                                            189

<210> SEQ ID NO 150
<211> LENGTH: 189
<212> TYPE: DNA
<213> ORGANISM: Artificial
<220> FEATURE:
<223> OTHER INFORMATION: promoter

<400> SEQUENCE: 150
cttactaatt taatgaatag aactcaattg tatgtccatt tgattcagtc ttatctctgg     60
cggtgttgac aagagataac aacgttgata taattgagcc cgtattgtta gcatgtacgt   120
ttaaaccagg aggaccagga tgtcaaagca acagatcggc gtagtcggta tggcagtgat   180
ggggcgcaa                                                            189

<210> SEQ ID NO 151
<211> LENGTH: 189
<212> TYPE: DNA
<213> ORGANISM: Artificial
<220> FEATURE:
<223> OTHER INFORMATION: promoter

<400> SEQUENCE: 151
cttactaatt taatgaatag aactcaattg tatgtccatt tgattcagtc ttatctctgg     60
cggtgttgac aagagataac aacgttgata taattgagcc cgtattgtta gcatgtacgt   120
ttaaaccagg agacaacgaa tgtcaaagca acagatcggc gtagtcggta tggcagtgat   180
ggggcgcaa                                                            189

<210> SEQ ID NO 152
<211> LENGTH: 189
```

<212> TYPE: DNA
<213> ORGANISM: Artificial
<220> FEATURE:
<223> OTHER INFORMATION: promoter

<400> SEQUENCE: 152

```
cttactaatt taatgaatag aactcaattg tatgtccatt tgattcagtc ttatctctgg    60
cggtgttgac aagagataac aacgttgata taattgagcc cgtattgtta gcatgtacgt   120
ttaaaccagg aggcgactaa tgtcaaagca acagatcggc gtagtcggta tggcagtgat   180
ggggcgcaa                                                           189
```

<210> SEQ ID NO 153
<211> LENGTH: 189
<212> TYPE: DNA
<213> ORGANISM: Artificial
<220> FEATURE:
<223> OTHER INFORMATION: promoter

<400> SEQUENCE: 153

```
cttactaatt taatgaatag aactcaattg tatgtccatt tgattcagtc ttatctctgg    60
cggtgttgac aagagataac aacgttgata taattgagcc cgtattgtta gcatgtacgt   120
ttaaaccagg agaagtcaaa tgtcaaagca acagatcggc gtagtcggta tggcagtgat   180
ggggcgcaa                                                           189
```

<210> SEQ ID NO 154
<211> LENGTH: 187
<212> TYPE: DNA
<213> ORGANISM: Artificial
<220> FEATURE:
<223> OTHER INFORMATION: promoter

<400> SEQUENCE: 154

```
aaatgcgccg tttgcaggtg aatcgacgct cagtctcagt ataaggaatt atctctggcg    60
gtgttgacaa gagataacaa cgttgatata attgagcccg tattgttagc atgtacgttt   120
aaaccaggag agacaagatg tcctcacgta aagagcttgc caatgctatt cgtgcgctga   180
gcatgga                                                             187
```

<210> SEQ ID NO 155
<211> LENGTH: 187
<212> TYPE: DNA
<213> ORGANISM: Artificial
<220> FEATURE:
<223> OTHER INFORMATION: promoter

<400> SEQUENCE: 155

```
aaatgcgccg tttgcaggtg aatcgacgct cagtctcagt ataaggaatt atctctggcg    60
gtgttgacaa gagataacaa cgttgatata attgagcccg tattgttagc atgtacgttt   120
aaaccaggag gtaccctatg tcctcacgta aagagcttgc caatgctatt cgtgcgctga   180
gcatgga                                                             187
```

<210> SEQ ID NO 156
<211> LENGTH: 187
<212> TYPE: DNA
<213> ORGANISM: Artificial
<220> FEATURE:
<223> OTHER INFORMATION: promoter

<400> SEQUENCE: 156

```
aaatgcgccg tttgcaggtg aatcgacgct cagtctcagt ataaggaatt atctctggcg    60
gtgttgacaa gagataacaa cgttgatata attgagcccg tattgttagc atgtacgttt   120
aaaccaggag aaaatcaatg tcctcacgta aagagcttgc caatgctatt cgtgcgctga   180
gcatgga                                                             187
```

<210> SEQ ID NO 157
<211> LENGTH: 187
<212> TYPE: DNA
<213> ORGANISM: Artificial
<220> FEATURE:
<223> OTHER INFORMATION: promoter

<400> SEQUENCE: 157

```
aaatgcgccg tttgcaggtg aatcgacgct cagtctcagt ataaggaatt atctctggcg    60
gtgttgacaa gagataacaa cgttgatata attgagcccg tattgttagc atgtacgttt   120
aaaccaggaa acagctaatg tcctcacgta aagagcttgc caatgctatt cgtgcgctga   180
gcatgga                                                             187
```

<210> SEQ ID NO 158
<211> LENGTH: 189
<212> TYPE: DNA
<213> ORGANISM: Artificial
<220> FEATURE:
<223> OTHER INFORMATION: promoter

<400> SEQUENCE: 158

```
tcgcctggcg ataaccgtct tgtcggcggt tgcgctgacg ttgcgtcgtg ttatctctgg    60
cggtgttgac aagagataac aacgttgata taattgagcc cgtattgtta gcatgtacgt   120
ttaaaccagg agatctaaga tgacggacaa attgacctcc cttcgtcagt acaccaccgt   180
agtggccga                                                           189
```

<210> SEQ ID NO 159
<211> LENGTH: 189
<212> TYPE: DNA
<213> ORGANISM: Artificial
<220> FEATURE:
<223> OTHER INFORMATION: promoter

<400> SEQUENCE: 159

```
tcgcctggcg ataaccgtct tgtcggcggt tgcgctgacg ttgcgtcgtg ttatctctgg    60
cggtgttgac aagagataac aacgttgata taattgagcc cgtattgtta gcatgtacgt   120
ttaaaccagg agaagagtaa tgacggacaa attgacctcc cttcgtcagt acaccaccgt   180
agtggccga                                                           189
```

<210> SEQ ID NO 160
<211> LENGTH: 189
<212> TYPE: DNA
<213> ORGANISM: Artificial
<220> FEATURE:
<223> OTHER INFORMATION: promoter

<400> SEQUENCE: 160

```
tcgcctggcg ataaccgtct tgtcggcggt tgcgctgacg ttgcgtcgtg ttatctctgg    60
cggtgttgac aagagataac aacgttgata taattgagcc cgtattgtta gcatgtacgt   120
ttaaaccagg aggtgcgaga tgacggacaa attgacctcc cttcgtcagt acaccaccgt   180
agtggccga                                                           189
```

```
<210> SEQ ID NO 161
<211> LENGTH: 189
<212> TYPE: DNA
<213> ORGANISM: Artificial
<220> FEATURE:
<223> OTHER INFORMATION: promoter

<400> SEQUENCE: 161
tcgcctggcg ataaccgtct tgtcggcggt tgcgctgacg ttgcgtcgtg ttatctctgg     60
cggtgttgac aagagataac aacgttgata taattgagcc cgtattgtta gcatgtacgt    120
ttaaaccagg agggccgtaa tgacggacaa attgacctcc cttcgtcagt acaccaccgt    180
agtggccga                                                            189
```